US008399459B2

(12) United States Patent
Andreini et al.

(10) Patent No.: US 8,399,459 B2
(45) Date of Patent: Mar. 19, 2013

(54) 1,4 OXAZINES AS BACE1 AND/OR BACE2 INHIBITORS

(75) Inventors: Matteo Andreini, Siena (IT); Emanuele Gabellieri, Siena (IT); Robert Narquizian, Zaessingue (FR); Massimiliano Travagli, Siena (IT); Wolfgang Wostl, Grenzach-Wyhlen (DE)

(73) Assignees: Hoffmann-La Roche Inc., Nutley, NJ (US); Siena Biotech SpA, Siena (IT)

( * ) Notice: Subject to any disclaimer, the term of this patent is extended or adjusted under 35 U.S.C. 154(b) by 0 days.

(21) Appl. No.: 13/357,640

(22) Filed: Jan. 25, 2012

(65) Prior Publication Data

US 2012/0196863 A1     Aug. 2, 2012

(30) Foreign Application Priority Data

Feb. 2, 2011   (EP) ..................................... 11153095

(51) Int. Cl.
*A61K 31/535*     (2006.01)
*C07D 265/28*     (2006.01)
(52) U.S. Cl. ...................................... 514/228.8; 544/98
(58) Field of Classification Search .................... 544/98; 514/228.8
See application file for complete search history.

(56) References Cited

FOREIGN PATENT DOCUMENTS

| EP | 1942105 | 7/2008 |
|---|---|---|
| WO | 2009/103626 | 8/2009 |
| WO | 2011/009943 | 1/2011 |
| WO | 2011/154431 | 12/2011 |

OTHER PUBLICATIONS

Selkoe et al., "Annual Review in Cell Biology" 10:373-403 ( 1994).
McConlogue et al., "J. Biol. Chem." 282(36):26326-26334 ( 2007).
Vassar et al., "Science" 286 (5440):735-741 ( 1999).
Hodges et al., "Human Molecular Genetics" 15(6):965-977 ( 2006).
Baggio et al., "Annual Review of Medicine" 57:265-281 ( 2006).
Hoffmeister et al., "Journal of the Pancreas" 10(5):501-506 ( 2009).
Basset et al., "Scandanavian Journal of Immunology" 51(3):307-311 ( 2000).
Merten et al., "Zeitschrift fur Kardiologie" (with English language Summary attached), 93(11):855-863 ( 2004).
Woodard-Grice et al., "Journal of Biological Chemistry" 283(39):26364-26373 ( 2008).
Gatchel et al., "Proceedings of the National Academy of Sciences of the USA" 105(4):1291-1296 ( 2008).
Fukui et al., "Cell Metabolism" 2:373-384 ( 2005).
Talantov et al., "Clinical Cancer Research" 11(20):7234-7242 ( 2005).
Roberds et al., "Human Molecular Genetics" 10(12):1317-1324 ( 2001).
Prentki et al., "J. Clin. Investig." 116(7):1802-1812 ( 2006).

Maugeri et al., "Srpski Arhivza Celokupno Lekarstuo" ((Suppl 1)), 138:50-52 ( 2010).
Kihara et al., "Proceedings of National Academy of Sciences of the USA" 106(51):21807-21812 ( 2009).
Barbiero et al., "Experimental Neurology" 182(2):335-345 ( 2003).
Luo et al., "Nature Neuroscience" 4(3):231-232 ( 2001).
Akpinar et al., "Cell Metabolism" 2:385-397 ( 2005).
Kiljanski et al., "Thyroid" 15(7):645-652 ( 2005).
Kim et al., "Neurobiology of Disease" 22(2):346-356 ( 2006).
Sugimoto et al., "Journal of Biological Chemistry" 282(48):34896-34903 ( 2007).
Desnues et al., "Clinical Vaccine Immunology" 13(2):170-178 ( 2006).
Koistinen et al., "Muscle & Nerve" 34(4):444-450 ( 2006).
Li et al., "Aging Cell" 5(2):153-165 ( 2006).
Finzi et al., "Ultrastructure of Pathology" 32(6):246-251 ( 2008).
Toegel et al., "Osteoarthritis & Cartilage" 18(2):240-248 ( 2010).
Hedlund et al., "Cancer Rsearch" 68(2):388-394 ( 2008).
Lichtenthaler et al., "Journal of Biological Chemistry" 278(49):48713-48719 ( 2003).
Kuhn et al., "Journal of Biological Chemistry" 282(16):11982-11995 ( 2007).
Lagos et al., "Blood" 109(4):1550-1558 ( 2007).
Zimmit et al., "Nature" 414:782-787 ( 2001).
Hardy et al., "Science" 297 (5580):353-356 ( 2002).
Vattemi et al., "Lancet" 358 (9297):1962-1964 ( 2001).
Wild et al., "Diabetes Care" 27(5):1047-1053 ( 2004).
Hussain et al., "Molecular and Cellular Neurosciences" 16:609-619 ( 2000).
Greenberg et al., "Annals of Neurology" 57(5):664-678 ( 2005).
Kondoh et al., "Breast Cancer & Research Treatment" 78(1):37-44 ( 2003).
Grewal et al., "Molecular & Cellular Biology" 26(13):4970-4981 ( 2006).
(International Search Report for PCT/EP2012/051481 Aug. 10, 2012).

*Primary Examiner* — Rebecca Anderson
(74) *Attorney, Agent, or Firm* — George W. Johnston; Patricia S. Rocha-Tramaloni; Kimberly J. Prior

(57) ABSTRACT

The present invention provides 1,4 Oxazines of formula I

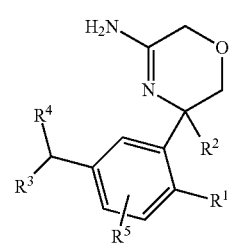

having BACE1 and/or BACE2 inhibitory activity, their manufacture, pharmaceutical compositions containing them and their use as therapeutically active substances. The active compounds of the present invention are useful in the therapeutic and/or prophylactic treatment of e.g. Alzheimer's disease and type 2 diabetes.

25 Claims, No Drawings

1,4 OXAZINES AS BACE1 AND/OR BACE2 INHIBITORS

PRIORITY TO RELATED APPLICATION(S)

This application claims the benefit of European Patent Application No. 11153095.2, filed Feb. 2, 2011, which is hereby incorporated by reference in its entirety.

FIELD OF THE INVENTION

The present invention provides 3-Amino-5-phenyl-5,6-dihydro-2H-[1,4]oxazines having BACE1 and/or BACE2 inhibitory properties, their manufacture, pharmaceutical compositions containing them and their use as therapeutically active substances.

BACKGROUND OF THE INVENTION

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science*. 2002 Jul. 19; 297(5580):353-6, Selkoe, Cell biology of the amyloid beta-protein precursor and the mechanism of Alzheimer's disease, *Annu Rev Cell Biol.* 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. AD-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science*. 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no AD-peptides are produced (Luo et al., Mice deficient in BACE1, the Alzheimer's beta-secretase, have normal phenotype and abolished beta-amyloid generation, *Nat Neurosci*. 2001 March; 4(3):231-2, Roberds et al., BACE knockout mice are healthy despite lacking the primary beta-secretase activity in brain: implications for Alzheimer's disease therapeutics, *Hum Mol Genet*. 2001 Jun. 1; 10(12):1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol Chem.* 2007 Sep. 7; 282(36):26326). It is thus presumed that inhibitors of BACE1 activity can be useful agents for therapeutic intervention in Alzheimer's disease (AD).

Type 2 diabetes (T2D) is caused by insulin resistance and inadequate insulin secretion from pancreatic β-cells leading to poor blood-glucose control and hyperglycemia (M Prentki & C J Nolan, "Islet beta-cell failure in type 2 diabetes." J. Clin. Investig. 2006, 116(7), 1802-1812). Patients with T2D have an increased risk of microvascular and macrovascular disease and a range of related complications including diabetic nephropathy, retinopathy and cardiovascular disease. In 2000, an estimated 171 million people had the condition with the expectation that this figure will double by 2030 (S Wild, G Roglic, A Green, R. Sicree & H King, "Global prevalence of diabetes", Diabetes Care 2004, 27(5), 1047-1053), making the disease a major healthcare problem. The rise in prevalence of T2D is associated with an increasingly sedentary lifestyle and high-energy food intake of the world's population (P Zimmet, K G M M Alberti & J Shaw, "Global and societal implications of the diabetes epidemic" Nature 2001, 414, 782-787).

β-Cell failure and consequent dramatic decline in insulin secretion and hyperglycemia marks the onset of T2D. Most current treatments do not prevent the loss of β-cell mass characterizing overt T2D. However, recent developments with GLP-1 analogues, gastrin and other agents show that preservation and proliferation of β-cells is possible to achieve, leading to an improved glucose tolerance and slower progression to overt T2D (L L Baggio & D J Drucker, "Therapeutic approaches to preserve islet mass in type 2 diabetes", Annu. Rev. Med. 2006, 57, 265-281).

Tmem27 has been identified as a protein promoting beta-cell proliferation (P Akpinar, S Kuwajima, J Krützfeldt, M Stoffel, "Tmem27: A cleaved and shed plasma membrane protein that stimulates pancreatic β cell proliferation", Cell Metab. 2005, 2, 385-397) and insulin secretion (K Fukui, Q Yang, Y Cao, N Takahashi et al., "The HNF-1 target Collectrin controls insulin exocytosis by SNARE complex formation", Cell Metab. 2005, 2, 373-384). Tmem27 is a 42 kDa membrane glycoprotein which is constitutively shed from the surface of β-cells, resulting from a degradation of the full-length cellular Tmem27. Overexpression of Tmem27 in a transgenic mouse increases β-cell mass and improves glucose tolerance in a diet-induced obesity DIO model of diabetes. Furthermore, siRNA knockout of Tmem27 in a rodent β-cell proliferation assay (e.g. using INS1e cells) reduces the proliferation rate, indicating a role for Tmem27 in control of β-cell mass.

In the same proliferation assay, BACE2 inhibitors also increase proliferation. However, BACE2 inhibition combined with Tmem27 siRNA knockdown results in low proliferation rates. Therefore, it is concluded that BACE2 is the protease responsible for the degradation of Tmem27. Furthermore, in vitro, BACE2 cleaves a peptide based on the sequence of Tmem27. The closely related protease BACE1 does not cleave this peptide and selective inhibition of BACE1 alone does not enhance proliferation of β-cells.

The close homolog BACE2 is a membrane-bound aspartyl protease and is co-localized with Tmem27 in human pancreatic β-cells (G Finzi, F Franzi, C Placidi, F Acquati et al., "BACE2 is stored in secretory granules of mouse and rat pancreatic beta cells", Ultrastruct Pathol. 2008, 32(6), 246-251). It is also known to be capable of degrading APP (I Hussain, D Powell, D Howlett, G Chapman et al., "ASP1 (BACE2) cleaves the amyloid precursor protein at the β-secretase site" Mol Cell Neurosci. 2000, 16, 609-619), IL-1R2 (P Kuhn, E Marjaux, A Imhof, B De Strooper et al., "Regulated intramembrane proteolysis of the interleukin-1 receptor II by alpha-, beta-, and gamma-secretase" J. Biol. Chem. 2007, 282(16), 11982-11995) and ACE2. The capability to degrade ACE2 indicates a possible role of BACE2 in the control of hypertension.

Inhibition of BACE2 is therefore proposed as a treatment for T2D with the potential to preserve and restore β-cell mass and stimulate insulin secretion in pre-diabetic and diabetic patients. It is therefore an object of the present invention to provide selective BACE2 inhibitors. Such compounds are useful as therapeutically active substances, particularly in the treatment and/or prevention of diseases which are associated with the inhibition of BACE2.

Furthermore, the formation, or formation and deposition, of β-amyloid peptides in, on or around neurological tissue (e.g., the brain) are inhibited by the present compounds, i.e. inhibition of the Aβ-production from APP or an APP fragment.

Inhibitors of BACE1 and/or BACE2 can in addition be used to treat the following diseases:
IBM (inclusion body myositis) (Vattemi G. et al., Lancet. 2001 Dec. 8; 358(9297):1962-4), Down's Syndrome (Barbiero L. et al, Exp Neurol. 2003 August; 182(2):335-45), Wilson's Disease (Sugimoto I. et al., J Biol. Chem. 2007 Nov. 30; 282(48):34896-903), Whipple's disease (Desnues B. et al., Clin Vaccine Immunol. 2006 February; 13(2):170-8), SpinoCerebellar Ataxia 1 and SpinoCerebellar Ataxia 7 (Gatchel J. R. et al., *Proc Natl Acad Sci USA* 2008 Jan. 29; 105(4):1291-6), Dermatomyositis (Greenberg S. A. et al., Ann Neurol. 2005 May; 57(5):664-78 and Greenberg S. A. et al., *Neurol* 2005 May; 57(5):664-78), Kaposi Sarcoma (Lagos D. et al, Blood, 2007 Feb. 15; 109(4):1550-8), Glioblastoma multiforme (E-MEXP-2576, http://www.ebi.ac.uk/microarray-as/aer/result?queryFor= PhysicalArray Design& aAccession=A-MEXP-258), Rheumatoid arthritis (Ungethuem U. et al, GSE2053), Amyotrophic lateral sclerosis (Koistinen H. et al., Muscle Nerve. 2006 October; 34(4):444-50 and Li Q. X. et al, Aging Cell. 2006 April; 5(2):153-65), Huntington's Disease (Kim Y. J. et al., Neurobiol Dis. 2006 May; 22(2):346-56. Epub 2006 Jan. 19 and Hodges A. et al., Hum Mol. Genet. 2006 Mar. 15; 15(6):965-77. Epub 2006 Feb. 8), Multiple Mieloma (Kihara Y. et al, Proc Natl Acad Sci USA. 2009 Dec. 22; 106(51):21807-12), Malignant melanoma (Talantov D. et al, Clin Cancer Res. 2005 Oct. 15; 11(20):7234-42), Sjogren syndrome (Basset C. et al., Scand J Immunol. 2000 March; 51(3):307-11), Lupus erythematosus (Grewal P. K. et al, Mol Cell Biol. 2006, July; 26(13):4970-81), Macrophagic myofasciitis, juvenile idiopathic arthritis, granulomatous arthritis, Breast cancer (Hedlund M. et al, Cancer Res. 2008 Jan. 15; 68(2):388-94 and Kondoh K. et al., Breast Cancer Res Treat. 2003 March; 78(1):37-44), Gastrointestinal diseases (Hoffmeister A. et al, JOP. 2009 Sep. 4; 10(5):501-6), Autoimmune/inflammatory diseases (Woodard-Grice A. V. et al., J Biol Chem. 2008 Sep. 26; 283(39): 26364-73. Epub 2008 Jul. 23), Rheumatoid Arthritis (Toegel S. et al, Osteoarthritis Cartilage. 2010 February; 18(2):240-8. Epub 2009 Sep. 22), Inflammatory reactions (Lichtenthaler S. F. et al., J Biol. Chem. 2003 Dec. 5; 278(49):48713-9. Epub 2003 Sep. 24), Arterial Thrombosis (Merten M. et al., Z Kardiol. 2004 November; 93(11):855-63), Cardiovascular diseases such as Myocardial infarction and stroke (Maugeri N. et al., Srp Arh Celok Lek. 2010 January; 138 Suppl 1:50-2) and Graves disease (Kiljański J. et al, Thyroid. 2005 July; 15(7):645-52).

SUMMARY OF THE INVENTION

The present invention provides novel compounds of formula I, their manufacture, pharmaceutical compositions containing them and their production, as well as the use of compounds of formula I in the control or prevention of illnesses such as Alzheimer's disease and type 2 diabetes. Furthermore the use of compounds of formula I in the treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease and Wilson's Disease. The novel compounds of formula I have improved pharmacological properties.

In particular, the present invention provides compounds of formula I,

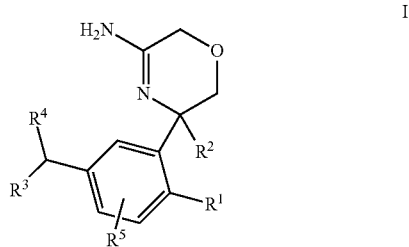

wherein the substituents and variables are as described below and in the claims, or a pharmaceutically acceptable salt thereof.

The present compounds have Asp2 (β-secretase, BACE1 or Memapsin-2) inhibitory activity and can therefore be used in the therapeutic and/or prophylactic treatment of diseases and disorders characterized by elevated β-amyloid levels and/or β-amyloid oligomers and/or β-amyloid plaques and further deposits, particularly Alzheimer's disease. The present compounds have BACE2 inhibitory activity and can therefore be used in the therapeutic and/or prophylactic treatment of diseases and disorders such as type 2 diabetes and other metabolic disorders.

DETAILED DESCRIPTION OF THE INVENTION

The present invention provides compounds of formula I and their pharmaceutically acceptable salts thereof, the preparation of these compounds, pharmaceutical compositions containing them and their manufacture, as well as the use of such compounds in the therapeutic and/or prophylactic treatment of diseases and disorders which are associated with inhibition of BACE1 and/or BACE2 activity, such as Alzheimer's disease and type 2 diabetes. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Optional" or "optionally" means that the subsequently described event or circumstance may, but need not, occur and that the description includes instances where the event or circumstance occurs and instances in which it does not.

The term "$C_{1-6}$-alkyl", alone or in combination with other groups, stands for a hydrocarbon radical which can be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. Particular "$C_{1-6}$-alkyl" are groups with 1 to 5 carbon atoms. Specific groups are methyl, ethyl and t-butyl, most specifically methyl.

The term "cyano-$C_{1-6}$-alkyl", alone or in combination with other groups, refers to $C_{1-6}$-alkyl as defined herein, which is substituted by one or multiple cyano, preferably 1-5 cyano, more preferably 1 cyano. Examples of such groups are cyanomethyl and the like.

The term "halogen-$C_{1-6}$-alkyl", alone or in combination with other groups, refers to $C_{1-6}$-alkyl as defined herein, which is substituted by one or multiple halogen atoms, preferably 1-5 halogen atoms, more preferably 1-3 halogen atoms, most preferably 1 halogen atom or 3 halogen atoms. A particular halogen is fluoro. A particular "halogen-$C_{1-6}$-alkyl" is fluoro-$C_{1-6}$-alkyl. Other examples are difluoromethyl, chloromethyl, fluoromethyl and the like. A specific example is trifluoromethyl.

The term "$C_{1-6}$-alkoxy-$C_{1-6}$-alkyl", alone or in combination with other groups, refers to $C_{1-6}$-alkyl, which is substituted by one or multiple $C_{1-6}$-alkoxy as defined herein. Examples are MeO-Me, 1MeO-Et, 2MeO-Et, 1MeO-2EtO-propyl and the like.

The term "cyano", alone or in combination with other groups, refers to N≡C—(NC—).

The term "acetonitrile", alone or in combination with other groups, refers to N≡C—CH$_2$—

The term "amido", alone or in combination with other groups, refers to —C(═O)—NH$_2$.

The term "amino", alone or in combination with other groups, refers to —NH$_2$.

The term "acetamidyl", alone or in combination with other groups, refers to —CH$_2$—C(═O)—NH$_2$.

The term "benzyl", alone or in combination with other groups, refers to phenyl-CH$_2$—.

The term "hydroxy", alone or in combination with other groups, refers to —OH.

The term "—C(O)-heterocyclyl", alone or in combination with other groups, refers to a heterocyclyl as defined herein linked via —C(═O)—.

The term "halogen", alone or in combination with other groups, denotes chloro (Cl), iodo (I), fluoro (F) and bromo (Br). Particular "halogens" are Cl and F. A specific halogen is F.

The term "aryl", alone or in combination with other groups, refers to an aromatic carbocyclic group containing 6 to 14, preferably 6 to 10, carbon atoms and having at least one aromatic ring or multiple condensed rings in which at least one ring is aromatic. Examples of "aryl" include benzyl, biphenyl, indanyl, naphthyl, phenyl (Ph) and the like. A particular "aryl" is phenyl.

The term "halogen-aryl", alone or in combination with other groups, refers to an "aryl" as defined herein substituted by 1, 2 or 3 "halogen" as defined herein. A particular "halogen-aryl" is halogen-phenyl. Specific examples are 2-chloro-phenyl, 3-chloro-phenyl, 2,5-dichloro-phenyl, 3,5-dichloro-phenyl, 3-chloro-4-fluoro-phenyl, 4-fluoro-phenyl, 2,4-difluoro-phenyl, 3,5-difluoro-phenyl and 2,3,5-trichloro-phenyl.

The term "$C_{1-6}$-alkyl-aryl", alone or in combination with other groups, refers to an "aryl" group as defined herein substituted by 1, 2 or 3 "$C_{1-6}$-alkyl" as defined herein. A particular "$C_{1-6}$-alkyl-aryl" is butyl-phenyl. A specific example is 4-tert-butyl-phenyl.

The term "$C_{1-6}$-alkoxy-aryl", alone or in combination with other groups, refers to an "aryl" group as defined herein substituted by 1, 2 or 3 "$C_{1-6}$-alkoxy" as defined herein. A particular "$C_{1-6}$-alkoxy-aryl" is ethoxy-phenyl. A specific example is 3-ethyoxy-phenyl.

The term "amino-aryl", alone or in combination with other groups, refers to an "aryl" group as defined herein substituted by 1, 2 or 3 "amino" groups as defined herein. A particular "amino-aryl" is amino-phenyl. A specific example is 3-amino-phenyl.

The term "heterocyclyl-C(═O)-halogen-aryl", alone or in combination with other groups, refers to an "aryl" group as defined herein substituted by "heterocyclyl-C(═O)-" as defined herein and "halogen" as defined herein. A particular "heterocyclyl-C(═O)-halogen-aryl" is (morpholinyl-ethanonyl)-chloro-phenyl. A specific example is (1-morpholin-4-yl-ethanonyl)-5-chloro-phenyl.

The term "$C_{1-6}$-alkyl-halogen-aryl", alone or in combination with other groups, refers to an "aryl" group as defined herein substituted by 1 or 2 "$C_{1-6}$-alkyl" as defined herein and 1 or 2 "halogen" atoms as defined herein, or by 1 or 2 "halogen-$C_{1-6}$-alkyl" as defined herein and 1 or 2 "halogen" atoms as defined herein. Particular "$C_{1-6}$-alkyl-halogen-aryl" groups are halogen-methyl-phenyl and chloro-trifluorom-ethyl-phenyl. Specific examples are 5-chloro-2-fluoro-3-methyl-phenyl, 3-chloro-5-methyl-phenyl, 4-chloro-3-methyl-phenyl and 5-chloro-3-trifluoromethyl-phenyl.

The term "acetonitrile-aryl", alone or in combination with other groups, refers to an "aryl" group as defined herein substituted by "acetonitrile" as defined herein. A particular "acetonitrile-aryl" group is acetonitrile-phenyl. A specific example is 3-acetonitril-phenyl.

The term "acetamidyl-halogen-aryl", alone or in combination with other groups, refers to an "aryl" group as defined herein substituted by "acetamidyl" as defined herein and 1 or 3 "halogen" atoms as defined herein. A particular "acetamidyl-halogen-aryl" is acetamidyl-chloro-phenyl. A specific example is 3-acetamidyl-5-chloro-phenyl.

The term "halogen-$C_{1-6}$-alkoxy-aryl", alone or in combination with other groups, refers to an "aryl" group as defined herein substituted by 1, 2 or 3 "halogen-$C_{1-6}$-alkoxy" as defined herein, or substituted by 1 or 2 "halogen" atoms as defined herein and 1 or 2 "$C_{1-6}$-alkoxy" as defined herein. Particular "halogen-$C_{1-6}$-alkoxy-aryl" are fluoromethoxy-phenyl and chloro-methoxy-phenyl. Specific examples are 3-difluoromethoxy-phenyl and 3-chloro-5-methoxy-phenyl.

The term "cyano-aryl", alone or in combination with other groups, refers to an "aryl" group as defined herein substituted by 1, 2 or 3 "cyano" as defined herein. A particular "cyano-aryl" group is cyano-phenyl. A specific example is 3-cyano-phenyl.

The term "$C_{1-6}$-alkyl-heteroaryl", alone or in combination with other groups, refers to a "heteroaryl" group as defined herein substituted by 1, 2 or 3 "$C_{1-6}$-alkyl" groups as defined herein. A particular "$C_{1-6}$-alkyl-heteroaryl" is methyl-1H-indazolyl. A specific example is 1-methyl-1H-indazol-4-yl.

The term "halogen-heteroaryl", alone or in combination with other groups, refers to a "heteroaryl" group as defined herein substituted by 1 or 2 "halogen" atoms as defined herein. Particular "halogen-heteroaryls" are chloro-pyridinyl, fluoro-pyridinyl, chloro-benzooxazolyl, chloro-1H-benzoimidazolyl, fluoro-benzo[1,3]dioxolyl and chloro-1H-indolyl. Specific examples are 2-chloro-pyridin-4-yl, 5-chloro-pyridin-2-yl, 5-chloro-pyridin-3-yl, 6-chloro-pyridin-3-yl, 2,5-dichloro-pyridin-3-yl, 2-fluoro-pyridin-3-yl, 2,6-difluoropyridin-3-yl, 6-chloro-benzooxazol-2-yl, 5-chloro-1H-benzoimidazol-2-yl, 2,2-difluoro-benzo[1,3]dioxol-5-yl and 6-chloro-1H-indol-2-yl.

The term "$C_{1-6}$-alkoxy-heteroaryl", alone or in combination with other groups, refers to a "heteroaryl" group as defined herein substituted by 1 or 2 "$C_{1-6}$-alkoxy" as defined herein. A particular is "$C_{1-6}$-alkoxy-heteroaryl" is methoxy-pyridinyl. A specific example is 5-methoxy-pyridin-3-yl.

The term "cyano-heteroaryl", alone or in combination with other groups, refers to a "heteroaryl" group as defined herein substituted by 1 or 2 "cyano" as defined herein. A particular "cyano-heteroaryl" is cyano-pyridinyl. A specific example is 5-cyano-pyridin-3-yl.

The term "heteroaryl", alone or in combination with other groups, refers to an aromatic group of having a single 4 to 8 membered ring or multiple condensed rings containing 6 to 14, in particular 6 to 10, ring atoms and containing 1, 2 or 3 heteroatoms individually selected from N, O and S, in particular N and O, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Particular "heteroaryl" are pyridinyl, benzooxazolyl, pyrimidinyl, benzo[1,3]dioxolyl, thiophenyl, 1H-benzoimidazolyl, 1H-indazolyl and 1H-Indolyl. Specific examples are pyridin-4-yl, pyridin-3-yl, pyridine-2-yl, benzooxazol-2-yl, pyrimidin-5-yl, benzo[1,3]dioxol-5-yl, thiophen-3-yl, 1H-indazol-4-yl, 1H-indol-5-yl and 1H-indol-2-yl.

The term "heterocyclyl", alone or in combination with other groups, denotes a monovalent saturated or partly unsaturated mono- or bicyclic ring system of 4 to 9 ring atoms, containing 1, 2, or 3 ring heteroatoms selected from N, O and S, the remaining ring atoms being carbon. Bicyclic means consisting of two rings having two ring atoms in common, i.e. the bridge separating the two rings is either a single bond or a chain of one or two ring atoms. Examples for monocyclic saturated heterocyclyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocyclyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, and 3-thia-9-aza-bicyclo[3.3.1]nonyl. Examples for partly unsaturated heterocyclyl are dihydrofuryl, imidazolinyl, dihydro-oxazolyl, tetrahydro-pyridinyl, and dihydropyranyl. Particular "heterocyclyl" are 2H-[1,4]oxazinyl and morpholinyl. Specific examples are morpholin-4-yl and 2H-[1,4]oxazin-3-yl.

The term "$C_{1-6}$-alkoxy", alone or in combination with other groups, stands for an —O—$C_{1-6}$-alkyl radical which can be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. Specific examples are methoxy and ethoxy.

The term "halogen-$C_{1-6}$-alkoxy", alone or in combination with other groups, refers to $C_{1-6}$-alkoxy as defined herein, which is substituted by one or multiple halogen atoms, in particular fluoro. A particular "halogen-$C_{1-6}$-alkoxy" is fluoro-$C_{1-6}$-alkoxy. Specific examples are difluoromethoxy and trifluoromethoxy.

The term "$C_{3-6}$-cycloalkyl", alone or in combination with other groups, denotes a monovalent saturated monocyclic or bicyclic hydrocarbon group of 3 to 6 ring carbon atoms, particularly a monovalent saturated monocyclic hydrocarbon group of 3 to 5 ring carbon atoms. Bicyclic means consisting of two saturated carbocyclic rings having two carbon atoms in common, i.e. the bridge separating the two rings is either a single bond or a chain of one or two carbon atoms. Particular $C_{3-6}$-cycloalkyl groups are monocyclic. Examples are cyclopropyl, cyclobutanyl, cyclopentyl, cyclohexyl or cycloheptyl. Examples for bicyclic cycloalkyl groups are bicyclo[2.2.1]heptanyl, bicyclo[2.2.2]octanyl and adamantanyl. A particular "$C_{3-6}$-cycloalkyl" is cyclohexyl.

The term "$C_{2-6}$-alkenyl", alone or in combination with other groups, denotes a monovalent linear or branched hydrocarbon group of 2 to 6 carbon atoms, in particular 2 to 4 carbon atoms, with at least one double bond. Examples of $C_{2-6}$-alkenyl include ethenyl, propenyl, prop-2-enyl, isopropenyl and butenyl.

The term "$C_{2-6}$-alkynyl", alone or in combination with other groups, denotes a monovalent linear or branched saturated hydrocarbon group of 2 to 6 carbon atoms, in particular from 2 to 4 carbon atoms, and containing one, two or three triple bonds. Examples of $C_{2-6}$-alkynyl include ethynyl, propynyl, prop-2-ynyl, isopropynyl and n-butynyl. Specific examples are ethynyl and propynyl.

The term "$C_{1-6}$-alkoxy-$C_{2-6}$-alkynyl", alone or in combination with other groups, refers to a "$C_{1-6}$-alkoxy" as defined herein linked via a "$C_{2-6}$-alkynyl" as defined herein. A specific example is 3-methoxy-prop-1-ynyl.

The term "halogen-heteroaryl-$C_{2-6}$-alkynyl", alone or in combination with other groups, refers to a "halogen-heteroaryl" group as defined herein linked via a "$C_{2-6}$-alkynyl" as defined herein. A specific example is 5-chloro-pyridin-2-ylethynyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Preferred are formic acid, trifluoroacetic acid and hydrochloric acid. Particular are hydrochloric acid, trifluoroacetic acid and fumaric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product containing specified ingredients in pre-determined amounts or proportions, as well as any product that results, directly or indirectly, from combining specified ingredients in specified amounts. Preferably it encompasses a product containing one or more active ingredients, and an optional carrier containing inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values ($-\log$ Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there can be one or more intermediates which are produced in the mixture which ultimately leads to the formation of the indicated and/or the desired product.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. The term "amino-protecting group" denotes groups intended to protect an amino group and includes benzyl, benzyloxycarbonyl (carbobenzyloxy, CBZ), 9-Fluorenylmethyloxycarbonyl (FMOC), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting groups. Particular amino-protecting groups are tert-butoxycarbonyl group, a bis(dimethoxyphenyl)-phenylmethyl and dimethoxytrityl.

The term "leaving group" denotes the group with the meaning conventionally associated with it in synthetic organic chemistry, i.e., an atom or group displaceable under substitution reaction conditions. Examples of leaving groups include halogen, in particular bromo, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, and acyloxy.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure.

The invention also provides pharmaceutical compositions, methods of using, and methods of preparing the aforementioned compounds.

All separate embodiments can be combined.

One embodiment of the invention is a compound of formula I,

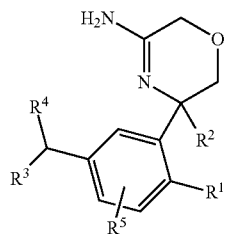

wherein
$R^1$ is selected from the group consisting of
i) hydrogen,
ii) halogen, and
iii) $C_{1-6}$-alkyl;
$R^2$ is selected from the group consisting of
i) hydrogen,
ii) $C_{1-6}$-alkyl,
iii) heteroaryl,
iv) heteroaryl substituted by 1-4 substituents individually selected from halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl,
v) aryl, and
vi) aryl substituted by 1-4 substituents individually selected from halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl;
$R^3$ and $R^4$ together with the C to which they are attached form a group selected from the group consisting of
i) aryl,
ii) aryl substituted by 1-4 substituents individually selected from acetamidyl, amino, amido, —C(O)-heterocyclyl, cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl,
iii) heteroaryl,
iv) heteroaryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl,
v) $C_{2-6}$-alkynyl,
vi) $C_{2-6}$-alkynyl substituted by 1-5 substituents individually selected from aryl, cyano, halogen-aryl, halogen, halogen-heteroaryl, heteroaryl, hydroxy, $C_{1-6}$-alkyl, $C_{1-6}$-alkyl-aryl, $C_{1-6}$-alkyl-heteroaryl and $C_{1-6}$-alkoxy,
vii) $C_{3-6}$-cycloalkyl,
viii) $C_{3-6}$-cycloalkyl substituted by 1-4 substituents individually selected from cyano, cyano-$C_{1-6}$-alkyl, halogen, halogen-$C_{1-6}$-alkoxy, halogen-$C_{1-6}$-alkyl, hydroxy, $C_{1-6}$-alkoxy, $C_{1-6}$-alkoxy-$C_{1-6}$-alkyl and $C_{1-6}$-alkyl,
ix) heterocyclyl, and
x) heterocyclyl substituted by 1-4 substituents individually selected from halogen, halogen-$C_{1-6}$-alkoxy, halogen-$C_{1-6}$-alkyl, hydroxy, $C_{1-6}$-alkoxy, $C_{1-6}$-alkoxy-$C_{1-6}$-alkyl and $C_{1-6}$-alkyl;
$R^5$ is selected from the group consisting of
i) hydrogen,
ii) halogen, and
iii) $C_{1-6}$-alkyl;
or pharmaceutically acceptable salts thereof.

A certain embodiment of the invention provides compound as described herein, wherein
$R^1$ is selected from the group consisting of
i) hydrogen and
ii) halogen;
$R^2$ is selected from the group consisting of
i) $C_{1-6}$-alkyl,
ii) heteroaryl substituted by halogen-$C_{1-6}$-alkoxy,
iii) aryl substituted by 1-2 substituents individually selected from halogen-$C_{1-6}$-alkoxy and $C_{1-6}$-alkyl,
$R^3$ and $R^4$ together with the C to which they are attached form a group selected from the group consisting of
i) aryl substituted by 1-3 substituents individually selected from acetamidyl, amino, —C(O)-heterocyclyl, cyano, cyano-$C_{1-6}$-alkyl, halogen, halogen-$C_{1-6}$-alkoxy, halogen-$C_{1-6}$-alkyl, $C_{1-6}$-alkoxy and $C_{1-6}$-alkyl,
ii) heteroaryl,
iii) heteroaryl substituted by 1-2 substituents individually selected from cyano, halogen, $C_{1-6}$-alkoxy and $C_{1-6}$-alkyl, and
iv) $C_{2-6}$-alkynyl substituted by 1 substituent selected from halogen-heteroaryl and $C_{1-6}$-alkoxy;
$R^5$ is selected from the group consisting of
i) hydrogen and
ii) halogen.

A certain embodiment of the invention provides compounds as described herein, wherein $R^1$ is halogen.

A certain embodiment of the invention provides compounds as described herein, wherein $R^1$ is F.

A certain embodiment of the invention provides compounds as described herein, wherein $R^1$ is hydrogen.

A certain embodiment of the invention provides compounds as described herein, wherein $R^2$ is selected from the group consisting of $C_{1-6}$-alkyl, heteroaryl substituted by halogen-$C_{1-6}$-alkoxy, and aryl substituted by 1-2 substituents individually selected from halogen-$C_{1-6}$-alkoxy and $C_{1-6}$-alkyl.

A certain embodiment of the invention provides compounds as described herein, wherein $R^2$ is $C_{1-6}$-alkyl.

A certain embodiment of the invention provides compounds as described herein, wherein $R^2$ is methyl.

A certain embodiment of the invention provides compounds as described herein, wherein $R^2$ is heteroaryl substituted by halogen-$C_{1-6}$-alkoxy.

A certain embodiment of the invention provides compounds as described herein, wherein $R^2$ is 6-difluoromethoxy-pyridin-3-yl.

A certain embodiment of the invention provides compounds as described herein, wherein $R^2$ is aryl substituted by halogen-$C_{1-6}$-alkoxy.

A certain embodiment of the invention provides compounds as described herein, wherein $R^2$ is aryl substituted by halogen-$C_{1-6}$-alkoxy or $C_{1-6}$-alkyl.

A certain embodiment of the invention provides compounds as described herein, wherein $R^2$ is 4-difluoromethoxy-3-methyl-phenyl.

A certain embodiment of the invention provides compounds as described herein, wherein $R^2$ is selected from the group consisting of 6-difluoromethoxy-pyridin-3-yl, 4-difluoromethoxy-3-methyl-phenyl and methyl.

A certain embodiment of the invention provides compounds as described herein, wherein $R^3$ and $R^4$ together with the C to which they are attached form a group selected from the group consisting of
i) aryl substituted by 1-3 substituents individually selected from acetamidyl, amino, —C(O)-heterocyclyl, cyano, cyano- $C_{1-6}$-alkyl, halogen, halogen-$C_{1-6}$-alkoxy, halogen-$C_{1-6}$-alkyl, $C_{1-6}$-alkoxy and $C_{1-6}$-alkyl, ii) heteroaryl, iii) heteroaryl substituted by 1-2 substituents individually selected from cyano, halogen, $C_{1-6}$-alkoxy and $C_{1-6}$-alkyl, and iv) $C_{2-6}$-alkynyl substituted by 1 substituent selected from halogen-heteroaryl and $C_{1-6}$-alkoxy.

A certain embodiment of the invention provides compounds as described herein, wherein $R^3$ and $R^4$ together with the C to which they are attached form an aryl substituted by 1-3 substituents individually selected from acetamidyl, amino, —C(O)-heterocyclyl, cyano, cyano-$C_{1-6}$-alkyl, halogen, halogen-$C_{1-6}$-alkoxy, halogen-$C_{1-6}$-alkyl, $C_{1-6}$-alkoxy and $C_{1-6}$-alkyl.

A certain embodiment of the invention provides compounds as described herein, wherein $R^3$ and $R^4$ together with the C to which they are attached form 3,5-dichloro-phenyl.

A certain embodiment of the invention provides compounds as described herein, wherein $R^3$ and $R^4$ together with the C to which they are attached form 7-methoxy-naphthalen-2-yl.

A certain embodiment of the invention provides compounds as described herein, wherein $R^3$ and $R^4$ together with the C to which they are attached form 4-fluoro-3-(2,2,2-trifluoro-ethoxy)-phenyl.

A certain embodiment of the invention provides compounds as described herein, wherein $R^3$ and $R^4$ together with the C to which they are attached form 3,5-bis-trifluoromethyl-phenyl.

A certain embodiment of the invention provides compounds as described herein, wherein $R^3$ and $R^4$ together with the C to which they are attached form 4,5-difluoro-3-methoxy-phenyl.

A certain embodiment of the invention provides compounds as described herein, wherein $R^3$ and $R^4$ together with the C to which they are attached form a group selected from the group consisting of 3-CN-phenyl, 3-chloro-phenyl, 3-difluoromethoxy-phenyl, 3,5-dichloro-phenyl, 3-chloro-4-fluoro-phenyl, 3,5-dichloro-phenyl, 2-chloro-phenyl, 3-acetonitril-phenyl, 2,4-difluoro-phenyl, 2,5-dichloro-phenyl, 3-acetamidyl-5-chloro-phenyl, 4-fluoro-phenyl, 3-chloro-5-methoxy-phenyl, 5-chloro-2-fluoro-3-methyl-phenyl, 3,5-dichloro-phenyl, 5-chloro-3-trifluoromethyl-phenyl, 3,5-difluoro-phenyl, 3-trifluoromethoxy-phenyl, 3-(1-morpholin-4-yl-ethanonyl)-5-chloro-phenyl, 3-chloro-5-methyl-phenyl, 3-amino-phenyl, 2,3,5-trichloro-phenyl, 4-tert-butyl-phenyl, 3-ethyoxy-phenyl, 4-chloro-3-methyl-phenyl, 4,5-difluoro-3-methoxy-phenyl, 3,5-bis-trifluoromethyl-phenyl, 4-fluoro-3-(2,2,2-trifluoro-ethoxy)-phenyl and 7-methoxy-naphthalen-2-yl.

A certain embodiment of the invention provides compounds as described herein, wherein $R^3$ and $R^4$ together with the C to which they are attached form a heteroaryl or a heteroaryl substituted by 1-2 substituents individually selected from cyano, halogen, $C_{1-6}$-alkoxy and $C_{1-6}$-alkyl.

A certain embodiment of the invention provides compounds as described herein, wherein $R^3$ and $R^4$ together with the C to which they are attached form a heteroaryl.

A certain embodiment of the invention provides compounds as described herein, wherein $R^3$ and $R^4$ together with the C to which they are attached form pyridin-3-yl.

A certain embodiment of the invention provides compounds as described herein, wherein $R^3$ and $R^4$ together with the C to which they are attached form pyrimidin-5-yl.

A certain embodiment of the invention provides compounds as described herein, wherein $R^3$ and $R^4$ together with the C to which they are attached form benzo[1,3]dioxol-5-yl.

A certain embodiment of the invention provides compounds as described herein, wherein $R^3$ and $R^4$ together with the C to which they are attached form thiophen-3-yl.

A certain embodiment of the invention provides compounds as described herein, wherein $R^3$ and $R^4$ together with the C to which they are attached form 1H-indol-5-yl.

A certain embodiment of the invention provides compounds as described herein, wherein $R^3$ and $R^4$ together with the C to which they are attached form a heteroaryl substituted by 1-2 substituents individually selected from cyano, halogen, $C_{1-6}$-alkoxy and $C_{1-6}$-alkyl.

A certain embodiment of the invention provides compounds as described herein, wherein $R^3$ and $R^4$ together with the C to which they are attached form 5-methoxy-pyridin-3-yl.

A certain embodiment of the invention provides compounds as described herein, wherein $R^3$ and $R^4$ together with the C to which they are attached form 2,6-difluoropyridin-3-yl.

A certain embodiment of the invention provides compounds as described herein, wherein $R^3$ and $R^4$ for together with the C to which they are attached form 2-fluoropyridin-3-yl.

A certain embodiment of the invention provides compounds as described herein, wherein $R^3$ and $R^4$ together with the C to which they are attached form 5-chloro-pyridin-2-yl.

A certain embodiment of the invention provides compounds as described herein, wherein $R^3$ and $R^4$ together with the C to which they are attached form 5-chloro-pyridin-3-yl.

A certain embodiment of the invention provides compounds as described herein, wherein $R^3$ and $R^4$ together with the C to which they are attached form 6-chloro-pyridin-3-yl.

A certain embodiment of the invention provides compounds as described herein, wherein $R^3$ and $R^4$ together with the C to which they are attached form 2,5-dichloro-pyridin-3-yl.

A certain embodiment of the invention provides compounds as described herein, wherein $R^3$ and $R^4$ together with the C to which they are attached form 5-cyano-pyridin-3-yl.

A certain embodiment of the invention provides compounds as described herein, wherein $R^3$ and $R^4$ together with the C to which they are attached form 2-chloro-pyridin-4-yl.

A certain embodiment of the invention provides compounds as described herein, wherein $R^3$ and $R^4$ together with the C to which they are attached 6-chloro-benzooxazol-2-yl.

A certain embodiment of the invention provides compounds as described herein, wherein $R^3$ and $R^4$ together with the C to which they are attached form 5-chloro-1H-benzoimidazol-2-yl.

A certain embodiment of the invention provides compounds as described herein, wherein $R^3$ and $R^4$ together with the C to which they are attached form 1-methyl-1H-indazol-4-yl.

A certain embodiment of the invention provides compounds as described herein, wherein $R^3$ and $R^4$ together with the C to which they are attached form 2,2-difluoro-benzo[1,3]dioxol-5-yl.

A certain embodiment of the invention provides compounds as described herein, wherein $R^3$ and $R^4$ together with the C to which they are attached form 6-chloro-1H-indol-2-yl.

A certain embodiment of the invention provides compounds as described herein, wherein $R^3$ and $R^4$ together with the C to which they are attached form 5-chloro-benzooxazol-2-yl.

A certain embodiment of the invention provides compounds as described herein, wherein $R^3$ and $R^4$ together with the C to which they are attached form a $C_{2-6}$-alkynyl substituted by 1 substituent selected from halogen-heteroaryl and $C_{1-6}$-alkoxy.

A certain embodiment of the invention provides compounds as described herein, wherein $R^3$ and $R^4$ together with the C to which they are attached form 5-chloro-pyridin-2-ylethynyl.

A certain embodiment of the invention provides compounds as described herein, wherein $R^3$ and $R^4$ together with the C to which they are attached form 3-methoxy-prop-1-ynyl.

A certain embodiment of the invention provides compounds as described herein, wherein $R^3$ and $R^4$ together with the C to which they are attached form phenylethynyl.

A certain embodiment of the invention provides compounds as described herein, wherein $R^3$ and $R^4$ together with the C to which they are attached form 3-thiophen-3-ylethynyl.

A certain embodiment of the invention provides compounds as described herein, wherein $R^3$ and $R^4$ together with the C to which they are attached form a group selected from the group consisting of 5-chloro-pyridin-2-ylethynyl, 3-methoxy-prop-1-ynyl, phenylethynyl and 3-thiophen-3-ylethynyl.

A certain embodiment of the invention provides compounds as described herein, wherein $R^3$ and $R^4$ together with the C to which they are attached form a group selected from the group consisting of 5-methoxy-pyridin-3-yl, 2,6-difluoropyridin-3-yl, 2-fluoropyridin-3-yl, 3,5-dichloro-phenyl, pyridin-3-yl, 5-chloro-pyridin-2-ylethynyl, 5-chloro-pyridin-3-yl, 5-cyano-pyridin-3-yl and 6-chloro-benzooxazol-2-yl.

A certain embodiment of the invention provides compounds as described herein, wherein $R^3$ and $R^4$ together with the C to which they are attached form a group selected from the group consisting of 1H-Indol-5-yl, 1-methyl-1H-indazol-4-yl, 2,2-difluoro-benzo[1,3]dioxol-5-yl, 2,3,5-trichloro-phenyl, 2,4-difluoro-phenyl, 2,5-dichloro-phenyl, 2,5-dichloro-pyridin-3-yl, 2,6-difluoropyridin-3-yl, 2-chloro-phenyl, 2-chloro-pyridin-4-yl, 2-fluoropyridin-3-yl, 3-(1-morpholin-4-yl-ethanonyl)-5-chloro-phenyl, 3,5-bis-trifluoromethyl-phenyl, 3,5-difluoro-phenyl, 3-acetamidyl-5-chloro-phenyl, 3-acetonitril-phenyl, 3-amino-phenyl, 3-chloro-4-fluoro-phenyl, 3-chloro-5-methoxy-phenyl, 3-chloro-5-methyl-phenyl, 3-chloro-phenyl, 3-CN-phenyl, 3-difluoromethoxy-phenyl, 3-ethyoxy-phenyl, 3-methoxy-prop-1-ynyl, 3-thiophen-3-ylethynyl, 3-trifluoromethoxy-phenyl, 4,5-difluoro-3-methoxy-phenyl, 4-chloro-3-methyl-phenyl, 4-fluoro-3-(2,2,2-trifluoro-ethoxy)-phenyl, 4-fluoro-phenyl, 4-tert-butyl-phenyl, 5-chloro-1H-benzoimidazol-2-yl, 5-chloro-2-fluoro-3-methyl-phenyl, 5-chloro-3-trifluoromethyl-phenyl, 5-chloro-benzooxazol-2-yl, 5-chloro-pyridin-2-yl, 5-chloro-pyridin-2-ylethynyl, 5-chloro-pyridin-3-yl, 5-CN-pyridin-3-yl, 5-methoxy-pyridin-3-yl, 6-chloro-1H-indol-2-yl, 6-chloro-benzooxazol-2-yl, 6-chloro-pyridin-3-yl, 7-methoxy-naphthalen-2-yl, benzo[1,3]dioxol-5-yl, phenylethynyl, pyridin-3-yl-, pyrimidin-5-yl- and thiophen-3-yl.

A certain embodiment of the invention provides compounds as described herein, wherein $R^3$ and $R^4$ together with the C to which they are attached form a group selected from the group consisting of 5-methoxy-pyridin-3-yl, 1H-indol-5-yl, 1-methyl-1H-indazol-4-yl, 1-morpholin-4-yl-ethanonyl-5-chloro-phenyl, 2,2-difluoro-benzo[1,3]dioxol-5-yl, 2,3,5-trichloro-phenyl, 2,4-difluoro-phenyl, 2,5-dichloro-phenyl, 2,5-dichloro-pyridin-3-yl, 2,6-difluoropyridin-3-yl, 2-chloro-phenyl, 2-chloro-pyridin-4-yl, 2-fluoro-pyridin-3-yl, 3,5-dichloro-phenyl, 3,5-difluoro-phenyl, 3-acetamidyl-5-chloro-phenyl, 3-acetonitril-phenyl, 3-amino-phenyl, 3-chloro-4-fluoro-phenyl, 3-chloro-5-methoxy-phenyl, 3-chloro-5-methyl-phenyl, 3-chloro-phenyl, 3-cyano-phenyl, 3-difluoromethoxy-phenyl, 3-ethyoxy-phenyl, 3-methoxy-prop-1-ynyl, 3-trifluoromethoxy-phenyl, 4-chloro-3-methyl-phenyl, 4-fluoro-phenyl, 4-tert-butyl-phenyl, 5-chloro-1H-benzoimidazol-2-yl, 5-chloro-2-fluoro-3-methyl-phenyl, 5-chloro-3-trifluoromethyl-phenyl, 5-chloro-pyridin-2-yl, 5-chloro-pyridin-2-ylethynyl, 5-chloro-pyridin-3-yl, 5-cyano-pyridin-3-yl, 5-methoxy-pyridin-3-yl, 6-chloro-1H-indol-2-yl, 6-chloro-benzooxazol-2-yl, 6-chloro-pyridin-3-yl, benzo[1,3]dioxol-5-yl, pyridin-3-yl, pyrimidin-5-yl and thiophen-3-yl.

A certain embodiment of the invention provides compounds as described herein, wherein $R^3$ and $R^4$ together with the C to which they are attached form a group selected from the group consisting of 5-methoxy-pyridin-3-yl, 5-chloro-pyridin-3-yl, pyridin-3-yl-, 5-methoxy-pyridin-3-yl, 5-chloro-pyridin-3-yl, 6-chloro-benzooxazol-2-yl, 2-fluoro-pyridin-3-yl, 5-CN-pyridin-3-yl, 6-chloro-pyridin-3-yl, 5-chloro-pyridin-3-yl, 2,5-dichloro-pyridin-3-yl, 2,6-difluoropyridin-3-yl, pyrimidin-5-yl-, pyrimidin-5-yl-, benzo[1,3]dioxol-5-yl, thiophen-3-yl, 2-chloro-pyridin-4-yl, 5-chloro-1H-benzoimidazol-2-yl, 1-methyl-1H-indazol-4-yl, 2,2-difluoro-benzo[1,3]dioxol-5-yl, 1H-indol-5-yl, 5-chloro-pyridin-2-yl, 6-chloro-1H-indol-2-yl, pyrimidin-5-yl-, 5-chloro-pyridin-3-yl and 5-chloro-benzooxazol-2-yl.

A certain embodiment of the invention provides compounds of formula Ic, wherein $R^1$, $R^2$, $R^3$, $R^4$ and $R^5$ are as described herein.

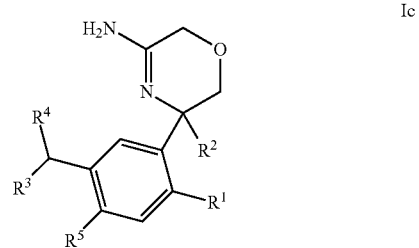

Ic

A certain embodiment of the invention provides compounds as described herein, wherein $R^5$ is halogen.

A certain embodiment of the invention provides compounds as described herein, wherein $R^5$ is F.

A certain embodiment of the invention provides compounds as described herein, wherein $R^5$ is hydrogen.

A certain embodiment of the invention provides compounds as described herein, selected from the group consisting of 5-(6-Difluoromethoxy-pyridin-3-yl)-5-[3-(5-methoxy-pyridin-3-yl)-phenyl]-5,6-dihydro-2H-[1,4]oxazin-3-ylamine, (R)-5-(3',5'-Dichloro-4-fluoro-biphenyl-3-yl)-5-methyl-5,6-dihydro-2H-[1,4]oxazin-3-ylamine,

[3'-(5-Amino-3-methyl-3,6-dihydro-2H-[1,4]oxazin-3-yl)-5-chloro-biphenyl-3-yl]-morpholin-4-yl-methanone,

[3'-(5-Amino-3-methyl-3,6-dihydro-2H-[1,4]oxazin-3-yl)-biphenyl-3-yl]-acetonitrile,
3'-(5-Amino-3-methyl-3,6-dihydro-2H-[1,4]oxazin-3-yl)-5-chloro-biphenyl-3-carboxylic acid amide,
3'-(5-Amino-3-methyl-3,6-dihydro-2H-[1,4]oxazin-3-yl)-biphenyl-3-carbonitrile,
5-(2',4'-Difluoro-biphenyl-3-yl)-5-methyl-5,6-dihydro-2H-[1,4]oxazin-3-ylamine,
5-(2',5'-Dichloro-biphenyl-3-yl)-5-methyl-5,6-dihydro-2H-[1,4]oxazin-3-ylamine,
5-(2'-Chloro-biphenyl-3-yl)-5-methyl-5,6-dihydro-2H-[1,4]oxazin-3-ylamine,
5-(2-Fluoro-5-pyrimidin-5-yl-phenyl)-5-methyl-5,6-dihydro-2H-[1,4]oxazin-3-ylamine,
5-(3-(2,6-difluoropyridin-3-yl)phenyl)-5-methyl-5,6-dihydro-2H-1,4-oxazin-3-amine,
5-(3-(2-fluoropyridin-3-yl)phenyl)-5-methyl-5,6-dihydro-2H-1,4-oxazin-3-amine,
5-(3-(5-amino-3-methyl-3,6-dihydro-2H-1,4-oxazin-3-yl)phenyl)nicotinonitrile,
5-(3',5'-Dichloro-6-fluoro-biphenyl-3-yl)-5-methyl-5,6-dihydro-2H-[1,4]oxazin-3-ylamine,
5-(3',5'-Dichloro-biphenyl-3-yl)-5-methyl-5,6-dihydro-2H-[1,4]oxazin-3-ylamine,
5-(3',5'-Difluoro-biphenyl-3-yl)-5-methyl-5,6-dihydro-2H-[1,4]oxazin-3-ylamine,
5-(3'-Amino-biphenyl-3-yl)-5-methyl-5,6-dihydro-2H-[1,4]oxazin-3-ylamine,
5-(3-Benzo[1,3]dioxol-5-yl-phenyl)-5-methyl-5,6-dihydro-2H-[1,4]oxazin-3-ylamine,
5-(3'-Chloro-4'-fluoro-biphenyl-3-yl)-5-methyl-5,6-dihydro-2H-[1,4]oxazin-3-ylamine,
5-(3'-Chloro-5'-methoxy-biphenyl-3-yl)-5-methyl-5,6-dihydro-2H-[1,4]oxazin-3-ylamine,
5-(3'-Chloro-5'-methyl-biphenyl-3-yl)-5-methyl-5,6-dihydro-2H-[1,4]oxazin-3-ylamine,
5-(3'-Chloro-biphenyl-3-yl)-5-methyl-5,6-dihydro-2H-[1,4]oxazin-3-ylamine,
5-(3'-Difluoromethoxy-biphenyl-3-yl)-5-methyl-5,6-dihydro-2H-[1,4]oxazin-3-ylamine,
5-(3'-Ethoxy-biphenyl-3-yl)-5-methyl-5,6-dihydro-2H-[1,4]oxazin-3-ylamine,
5-(4'-Chloro-3'-methyl-biphenyl-3-yl)-5-methyl-5,6-dihydro-2H-[1,4]oxazin-3-ylamine,
5-(4-Difluoromethoxy-3-methyl-phenyl)-5-(3-pyridin-3-yl-phenyl)-5,6-dihydro-2H-[1,4]oxazin-3-ylamine,
5-(4'-Fluoro-biphenyl-3-yl)-5-methyl-5,6-dihydro-2H-[1,4]oxazin-3-ylamine,
5-(4'-tert-Butyl-biphenyl-3-yl)-5-methyl-5,6-dihydro-2H-[1,4]oxazin-3-ylamine,
5-(5'-Chloro-2'-fluoro-3'-methyl-biphenyl-3-yl)-5-methyl-5,6-dihydro-2H-[1,4]oxazin-3-ylamine; compound with formic acid,
5-(5'-Chloro-3'-trifluoromethyl-biphenyl-3-yl)-5-methyl-5,6-dihydro-2H-[1,4]oxazin-3-ylamine,
5-[3-(1H-Indol-5-yl)-phenyl]-5-methyl-5,6-dihydro-2H-[1,4]oxazin-3-ylamine,
5-[3-(2,2-Difluoro-benzo[1,3]dioxol-5-yl)-phenyl]-5-methyl-5,6-dihydro-2H-[1,4]oxazin-3-ylamine,
5-[3-(2,5-Dichloro-pyridin-3-yl)-phenyl]-5-methyl-5,6-dihydro-2H-[1,4]oxazin-3-ylamine,
5-[3-(2-Chloro-pyridin-4-yl)-phenyl]-5-methyl-5,6-dihydro-2H-[1,4]oxazin-3-ylamine,
5-[3-(3-Methoxy-prop-1-ynyl)-phenyl]-5-methyl-5,6-dihydro-2H-[1,4]oxazin-3-ylamine,
5-[3-(5-Chloro-1H-benzoimidazol-2-yl)-phenyl]-5-methyl-5,6-dihydro-2H-[1,4]oxazin-3-ylamine,
5-[3-(5-Chloro-pyridin-2-yl)-phenyl]-5-methyl-5,6-dihydro-2H-[1,4]oxazin-3-ylamine,
5-[3-(5-Chloro-pyridin-2-ylethynyl)-phenyl]-5-methyl-5,6-dihydro-2H-[1,4]oxazin-3-ylamine,
5-[3-(5-Chloro-pyridin-3-yl)-phenyl]-5-(4-difluoromethoxy-3-methyl-phenyl)-5,6-dihydro-2H-[1,4]oxazin-3-ylamine,
5-[3-(5-Chloro-pyridin-3-yl)-phenyl]-5-(6-difluoromethoxy-pyridin-3-yl)-5,6-dihydro-2H-[1,4]oxazin-3-ylamine,
5-[3-(5-Chloro-pyridin-3-yl)-phenyl]-5-methyl-5,6-dihydro-2H-[1,4]oxazin-3-ylamine,
5-[3-(5-Methoxy-pyridin-3-yl)-phenyl]-5-methyl-5,6-dihydro-2H-[1,4]oxazin-3-ylamine,
5-[3-(6-Chloro-1H-indol-2-yl)-phenyl]-5-methyl-5,6-dihydro-2H-[1,4]oxazin-3-ylamine,
5-[3-(6-Chloro-benzooxazol-2-yl)-phenyl]-5-methyl-5,6-dihydro-2H-[1,4]oxazin-3-ylamine,
5-[3-(6-Chloro-pyridin-3-yl)-phenyl]-5-(4-difluoromethoxy-3-methyl-phenyl)-5,6-dihydro-2H-[1,4]oxazin-3-ylamine,
5-Methyl-5-(2',3',5'-trichloro-biphenyl-3-yl)-5,6-dihydro-2H-[1,4]oxazin-3-ylamine,
5-Methyl-5-(3-pyrimidin-5-yl-phenyl)-5,6-dihydro-2H-[1,4]oxazin-3-ylamine,
5-Methyl-5-(3-thiophen-3-yl-phenyl)-5,6-dihydro-2H-[1,4]oxazin-3-ylamine,
5-Methyl-5-(3'-trifluoromethoxy-biphenyl-3-yl)-5,6-dihydro-2H-[1,4]oxazin-3-ylamine, and
5-Methyl-5-[3-(1-methyl-1H-indazol-4-yl)-phenyl]-5,6-dihydro-2H-[1,4]oxazin-3-ylamine,
or a pharmaceutical acceptable salt thereof.

A certain embodiment of the invention provides compounds as described herein, selected from the group consisting of
5-(6-Difluoromethoxy-pyridin-3-yl)-5-[3-(5-methoxy-pyridin-3-yl)-phenyl]-5,6-dihydro-2H-[1,4]oxazin-3-ylamine,
(R)-5-(3',5'-Dichloro-4-fluoro-biphenyl-3-yl)-5-methyl-5,6-dihydro-2H-[1,4]oxazin-3-ylamine,
[3'-(5-Amino-3-methyl-3,6-dihydro-2H-[1,4]oxazin-3-yl)-5-chloro-biphenyl-3-yl]-morpholin-4-yl-methanone,
[3'-(5-Amino-3-methyl-3,6-dihydro-2H-[1,4]oxazin-3-yl)-biphenyl-3-yl]-acetonitrile,
3'-(5-Amino-3-methyl-3,6-dihydro-2H-[1,4]oxazin-3-yl)-5-chloro-biphenyl-3-carboxylic acid amide,
3'-(5-Amino-3-methyl-3,6-dihydro-2H-[1,4]oxazin-3-yl)-biphenyl-3-carbonitrile,
5-(2',4'-Difluoro-biphenyl-3-yl)-5-methyl-5,6-dihydro-2H-[1,4]oxazin-3-ylamine,
5-(2',5'-Dichloro-biphenyl-3-yl)-5-methyl-5,6-dihydro-2H-[1,4]oxazin-3-ylamine,
5-(2'-Chloro-biphenyl-3-yl)-5-methyl-5,6-dihydro-2H-[1,4]oxazin-3-ylamine,
5-(2-Fluoro-5-pyrimidin-5-yl-phenyl)-5-methyl-5,6-dihydro-2H-[1,4]oxazin-3-ylamine,
5-(3-(2,6-difluoropyridin-3-yl)phenyl)-5-methyl-5,6-dihydro-2H-1,4-oxazin-3-amine,
5-(3-(2-fluoropyridin-3-yl)phenyl)-5-methyl-5,6-dihydro-2H-1,4-oxazin-3-amine,
5-(3-(5-amino-3-methyl-3,6-dihydro-2H-1,4-oxazin-3-yl)phenyl)nicotinonitrile,
5-(3',5'-Dichloro-6-fluoro-biphenyl-3-yl)-5-methyl-5,6-dihydro-2H-[1,4]oxazin-3-ylamine,
5-(3',5'-Dichloro-biphenyl-3-yl)-5-methyl-5,6-dihydro-2H-[1,4]oxazin-3-ylamine, 5-(3',5'-Difluoro-biphenyl-3-yl)-5-methyl-5,6-dihydro-2H-[1,4]oxazin-3-ylamine,
5-(3'-Amino-biphenyl-3-yl)-5-methyl-5,6-dihydro-2H-[1,4]oxazin-3-ylamine,
5-(3-Benzo[1,3]dioxol-5-yl-phenyl)-5-methyl-5,6-dihydro-2H-[1,4]oxazin-3-ylamine,
5-(3'-Chloro-4'-fluoro-biphenyl-3-yl)-5-methyl-5,6-dihydro-2H-[1,4]oxazin-3-ylamine,
5-(3'-Chloro-5'-methoxy-biphenyl-3-yl)-5-methyl-5,6-dihydro-2H-[1,4]oxazin-3-ylamine,
5-(3'-Chloro-5'-methyl-biphenyl-3-yl)-5-methyl-5,6-dihydro-2H-[1,4]oxazin-3-ylamine,
5-(3'-Chloro-biphenyl-3-yl)-5-methyl-5,6-dihydro-2H-[1,4]oxazin-3-ylamine,
5-(3'-Difluoromethoxy-biphenyl-3-yl)-5-methyl-5,6-dihydro-2H-[1,4]oxazin-3-ylamine,
5-(3'-Ethoxy-biphenyl-3-yl)-5-methyl-5,6-dihydro-2H-[1,4]oxazin-3-ylamine,
5-(4'-Chloro-3'-methyl-biphenyl-3-yl)-5-methyl-5,6-dihydro-2H-[1,4]oxazin-3-ylamine,
5-(4-Difluoromethoxy-3-methyl-phenyl)-5-(3-pyridin-3-yl-phenyl)-5,6-dihydro-2H-[1,4]oxazin-3-ylamine,
5-(4'-Fluoro-biphenyl-3-yl)-5-methyl-5,6-dihydro-2H-[1,4]oxazin-3-ylamine,
5-(4'-tert-Butyl-biphenyl-3-yl)-5-methyl-5,6-dihydro-2H-[1,4]oxazin-3-ylamine,
5-(5'-Chloro-2'-fluoro-3'-methyl-biphenyl-3-yl)-5-methyl-5,6-dihydro-2H-[1,4]oxazin-3-ylamine; compound with formic acid,
5-(5'-Chloro-3'-trifluoromethyl-biphenyl-3-yl)-5-methyl-5,6-dihydro-2H-[1,4]oxazin-3-ylamine,
5-[3-(1H-Indol-5-yl)-phenyl]-5-methyl-5,6-dihydro-2H-[1,4]oxazin-3-ylamine,
5-[3-(2,2-Difluoro-benzo[1,3]dioxol-5-yl)-phenyl]-5-methyl-5,6-dihydro-2H-[1,4]oxazin-3-ylamine,
5-[3-(2,5-Dichloro-pyridin-3-yl)-phenyl]-5-methyl-5,6-dihydro-2H-[1,4]oxazin-3-ylamine,
5-[3-(2-Chloro-pyridin-4-yl)-phenyl]-5-methyl-5,6-dihydro-2H-[1,4]oxazin-3-ylamine,
5-[3-(3-Methoxy-prop-1-ynyl)-phenyl]-5-methyl-5,6-dihydro-2H-[1,4]oxazin-3-ylamine,
5-[3-(5-Chloro-1H-benzoimidazol-2-yl)-phenyl]-5-methyl-5,6-dihydro-2H-[1,4]oxazin-3-ylamine,
5-[3-(5-Chloro-pyridin-2-yl)-phenyl]-5-methyl-5,6-dihydro-2H-[1,4]oxazin-3-ylamine,
5-[3-(5-Chloro-pyridin-2-ylethynyl)-phenyl]-5-methyl-5,6-dihydro-2H-[1,4]oxazin-3-ylamine,
5-[3-(5-Chloro-pyridin-3-yl)-phenyl]-5-(4-difluoromethoxy-3-methyl-phenyl)-5,6-dihydro-2H-[1,4]oxazin-3-ylamine,
5-[3-(5-Chloro-pyridin-3-yl)-phenyl]-5-(6-difluoromethoxy-pyridin-3-yl)-5,6-dihydro-2H-[1,4]oxazin-3-ylamine,
5-[3-(5-Chloro-pyridin-3-yl)-phenyl]-5-methyl-5,6-dihydro-2H-[1,4]oxazin-3-ylamine,
5-[3-(5-Methoxy-pyridin-3-yl)-phenyl]-5-methyl-5,6-dihydro-2H-[1,4]oxazin-3-ylamine,
5-[3-(6-Chloro-1H-indol-2-yl)-phenyl]-5-methyl-5,6-dihydro-2H-[1,4]oxazin-3-ylamine,
5-[3-(6-Chloro-benzooxazol-2-yl)-phenyl]-5-methyl-5,6-dihydro-2H-[1,4]oxazin-3-ylamine,
5-[3-(6-Chloro-pyridin-3-yl)-phenyl]-5-(4-difluoromethoxy-3-methyl-phenyl)-5,6-dihydro-2H-[1,4]oxazin-3-ylamine,
5-Methyl-5-(2',3',5'-trichloro-biphenyl-3-yl)-5,6-dihydro-2H-[1,4]oxazin-3-ylamine,
5-Methyl-5-(3-pyrimidin-5-yl-phenyl)-5,6-dihydro-2H-[1,4]oxazin-3-ylamine,
5-Methyl-5-(3-thiophen-3-yl-phenyl)-5,6-dihydro-2H-[1,4]oxazin-3-ylamine,
5-Methyl-5-(3'-trifluoromethoxy-biphenyl-3-yl)-5,6-dihydro-2H-[1,4]oxazin-3-ylamine,
5-Methyl-5-[3-(1-methyl-1H-indazol-4-yl)-phenyl]-5,6-dihydro-2H-[1,4]oxazin-3-ylamine,
5-Difluoromethyl-5-(2-fluoro-5-pyrimidin-5-yl-phenyl)-5,6-dihydro-2H-[1,4]oxazin-3-ylamine,
5-[5-(5-Chloro-pyridin-3-yl)-2-fluoro-phenyl]-5-difluoromethyl-5,6-dihydro-2H-[1,4]oxazin-3-ylamine,
5-[3-(5-Chloro-benzooxazol-2-yl)-phenyl]-5-methyl-5,6-dihydro-2H-[1,4]oxazin-3-ylamine,
(RS)-5-[3-(5-Chloro-benzooxazol-2-yl)-phenyl]-5-methyl-5,6-dihydro-2H-[1,4]oxazin-3-ylamine hydrochloride,
5-Methyl-5-(3-phenylethynyl-phenyl)-5,6-dihydro-2H-[1,4]oxazin-3-ylamine,
5-Methyl-5-(3-thiophen-3-ylethynyl-phenyl)-5,6-dihydro-2H-[1,4]oxazin-3-ylamine,
5-(4',5'-Difluoro-3'-methoxy-biphenyl-3-yl)-5-methyl-5,6-dihydro-2H-[1,4]oxazin-3-ylamine formate,
5-(3',5'-Bis-trifluoromethyl-biphenyl-3-yl)-5-methyl-5,6-dihydro-2H-[1,4]oxazin-3-ylamine formate,
5-[4'-Fluoro-3'-(2,2,2-trifluoro-ethoxy)-biphenyl-3-yl]-5-methyl-5,6-dihydro-2H-[1,4]oxazin-3-ylamine formate, and
5-[3-(7-Methoxy-naphthalen-2-yl)-phenyl]-5-methyl-5,6-dihydro-2H-[1,4]oxazin-3-ylamine formate or a pharmaceutical acceptable salt thereof.

A certain embodiment of the invention provides compounds as described herein, selected from the group consisting of 5-(6-Difluoromethoxy-pyridin-3-yl)-5-[3-(5-methoxy-pyridin-3-yl)-phenyl]-5,6-dihydro-2H-[1,4]oxazin-3-ylamine,
(R)-5-(3',5'-Dichloro-4-fluoro-biphenyl-3-yl)-5-methyl-5,6-dihydro-2H-[1,4]oxazin-3-ylamine,
[3'-(5-Amino-3-methyl-3,6-dihydro-2H-[1,4]oxazin-3-yl)-5-chloro-biphenyl-3-yl]-morpholin-4-yl-methanone,
[3'-(5-Amino-3-methyl-3,6-dihydro-2H-[1,4]oxazin-3-yl)-biphenyl-3-yl]-acetonitrile,
3'-(5-Amino-3-methyl-3,6-dihydro-2H-[1,4]oxazin-3-yl)-5-chloro-biphenyl-3-carboxylic acid amide,
3'-(5-Amino-3-methyl-3,6-dihydro-2H-[1,4]oxazin-3-yl)-biphenyl-3-carbonitrile,
5-(2',4'-Difluoro-biphenyl-3-yl)-5-methyl-5,6-dihydro-2H-[1,4]oxazin-3-ylamine,
5-(2',5'-Dichloro-biphenyl-3-yl)-5-methyl-5,6-dihydro-2H-[1,4]oxazin-3-ylamine,
5-(2'-Chloro-biphenyl-3-yl)-5-methyl-5,6-dihydro-2H-[1,4]oxazin-3-ylamine,
5-(2-Fluoro-5-pyrimidin-5-yl-phenyl)-5-methyl-5,6-dihydro-2H-[1,4]oxazin-3-ylamine,
5-(3-(2,6-Difluoropyridin-3-yl)phenyl)-5-methyl-5,6-dihydro-2H-1,4-oxazin-3-amine,
5-(3-(2-Dluoropyridin-3-yl)phenyl)-5-methyl-5,6-dihydro-2H-1,4-oxazin-3-amine,
5-(3-(5-Amino-3-methyl-3,6-dihydro-2H-1,4-oxazin-3-yl)phenyl)nicotinonitrile,
5-(3',5'-Dichloro-6-fluoro-biphenyl-3-yl)-5-methyl-5,6-dihydro-2H-[1,4]oxazin-3-ylamine,
5-(3',5'-Dichloro-biphenyl-3-yl)-5-methyl-5,6-dihydro-2H-[1,4]oxazin-3-ylamine,
5-(3',5'-Difluoro-biphenyl-3-yl)-5-methyl-5,6-dihydro-2H-[1,4]oxazin-3-ylamine, 5-(3'-Amino-biphenyl-3-yl)-5-methyl-5,6-dihydro-2H-[1,4]
oxazin-3-ylamine,
5-(3-Benzo[1,3]dioxol-5-yl-phenyl)-5-methyl-5,6-dihydro-
2H-[1,4]oxazin-3-ylamine,
5-(3'-Chloro-4'-fluoro-biphenyl-3-yl)-5-methyl-5,6-dihydro-2H-[1,4]oxazin-3-ylamine,
5-(3'-Chloro-5'-methoxy-biphenyl-3-yl)-5-methyl-5,6-dihydro-2H-[1,4]oxazin-3-ylamine,
5-(3'-Chloro-5'-methyl-biphenyl-3-yl)-5-methyl-5,6-dihydro-2H-[1,4]oxazin-3-ylamine,
5-(3'-Chloro-biphenyl-3-yl)-5-methyl-5,6-dihydro-2H-[1,4]
oxazin-3-ylamine,
5-(3'-Difluoromethoxy-biphenyl-3-yl)-5-methyl-5,6-dihydro-2H-[1,4]oxazin-3-ylamine,
5-(3'-Ethoxy-biphenyl-3-yl)-5-methyl-5,6-dihydro-2H-[1,4]
oxazin-3-ylamine,
5-(4'-Chloro-3'-methyl-biphenyl-3-yl)-5-methyl-5,6-dihydro-2H-[1,4]oxazin-3-ylamine,
5-(4-Difluoromethoxy-3-methyl-phenyl)-5-(3-pyridin-3-yl-phenyl)-5,6-dihydro-2H-[1,4]oxazin-3-ylamine,
5-(4'-Fluoro-biphenyl-3-yl)-5-methyl-5,6-dihydro-2H-[1,4]
oxazin-3-ylamine,
5-(4'-tert-Butyl-biphenyl-3-yl)-5-methyl-5,6-dihydro-2H-
[1,4]oxazin-3-ylamine,
5-(5'-Chloro-2'-fluoro-3'-methyl-biphenyl-3-yl)-5-methyl-5,6-dihydro-2H-[1,4]oxazin-3-ylamine formate,
5-(5'-Chloro-3'-trifluoromethyl-biphenyl-3-yl)-5-methyl-5,6-dihydro-2H-[1,4]oxazin-3-ylamine,
5-[3-(1H-Indol-5-yl)-phenyl]-5-methyl-5,6-dihydro-2H-[1,4]oxazin-3-ylamine,
5-[3-(2,2-Difluoro-benzo[1,3]dioxol-5-yl)-phenyl]-5-methyl-5,6-dihydro-2H-[1,4]oxazin-3-ylamine,
5-[3-(2,5-Dichloro-pyridin-3-yl)-phenyl]-5-methyl-5,6-dihydro-2H-[1,4]oxazin-3-ylamine,
5-[3-(2-Chloro-pyridin-4-yl)-phenyl]-5-methyl-5,6-dihydro-2H-[1,4]oxazin-3-ylamine,
5-[3-(3-Methoxy-prop-1-ynyl)-phenyl]-5-methyl-5,6-dihydro-2H-[1,4]oxazin-3-ylamine,
5-[3-(5-Chloro-1H-benzoimidazol-2-yl)-phenyl]-5-methyl-5,6-dihydro-2H-[1,4]oxazin-3-ylamine,
5-[3-(5-Chloro-pyridin-2-yl)-phenyl]-5-methyl-5,6-dihydro-2H-[1,4]oxazin-3-ylamine,
5-[3-(5-Chloro-pyridin-2-ylethynyl)-phenyl]-5-methyl-5,6-dihydro-2H-[1,4]oxazin-3-ylamine,
5-[3-(5-Chloro-pyridin-3-yl)-phenyl]-5-(4-difluoromethoxy-3-methyl-phenyl)-5,6-dihydro-2H-[1,4]oxazin-3-ylamine,
5-[3-(5-Chloro-pyridin-3-yl)-phenyl]-5-(6-difluoromethoxy-pyridin-3-yl)-5,6-dihydro-2H-[1,4]oxazin-3-ylamine,
5-[3-(5-Chloro-pyridin-3-yl)-phenyl]-5-methyl-5,6-dihydro-2H-[1,4]oxazin-3-ylamine,
5-[3-(5-Methoxy-pyridin-3-yl)-phenyl]-5-methyl-5,6-dihydro-2H-[1,4]oxazin-3-ylamine,
5-[3-(6-Chloro-1H-indol-2-yl)-phenyl]-5-methyl-5,6-dihydro-2H-[1,4]oxazin-3-ylamine,
5-[3-(6-Chloro-benzooxazol-2-yl)-phenyl]-5-methyl-5,6-dihydro-2H-[1,4]oxazin-3-ylamine,
5-[3-(6-Chloro-pyridin-3-yl)-phenyl]-5-(4-difluoromethoxy-3-methyl-phenyl)-5,6-dihydro-2H-[1,4]oxazin-3-ylamine,
5-Methyl-5-(2',3',5'-trichloro-biphenyl-3-yl)-5,6-dihydro-2H-[1,4]oxazin-3-ylamine,
5-Methyl-5-(3-pyrimidin-5-yl-phenyl)-5,6-dihydro-2H-[1,4]oxazin-3-ylamine,
5-Methyl-5-(3-thiophen-3-yl-phenyl)-5,6-dihydro-2H-[1,4]oxazin-3-ylamine,
5-Methyl-5-(3'-trifluoromethoxy-biphenyl-3-yl)-5,6-dihydro-2H-[1,4]oxazin-3-ylamine, and
5-Methyl-5-[3-(1-methyl-1H-indazol-4-yl)-phenyl]-5,6-dihydro-2H-[1,4]oxazin-3-ylamine,
or a pharmaceutical acceptable salt thereof.

A certain embodiment of the invention provides compounds as described herein, selected from the group consisting of 5-(6-Difluoromethoxy-pyridin-3-yl)-5-[3-(5-methoxy-pyridin-3-yl)-phenyl]-5,6-dihydro-2H-[1,4]oxazin-3-ylamine hydrochloride,
(R)-5-(3',5'-Dichloro-4-fluoro-biphenyl-3-yl)-5-methyl-5,6-dihydro-2H-[1,4]oxazin-3-ylamine formate,
[3'-(5-Amino-3-methyl-3,6-dihydro-2H-[1,4]oxazin-3-yl)-5-chloro-biphenyl-3-yl]-morpholin-4-yl-methanone formate,
[3'-(5-Amino-3-methyl-3,6-dihydro-2H-[1,4]oxazin-3-yl)-biphenyl-3-yl]-acetonitrile formate,
3'-(5-Amino-3-methyl-3,6-dihydro-2H-[1,4]oxazin-3-yl)-5-chloro-biphenyl-3-carboxylic acid amide formate,
3'-(5-Amino-3-methyl-3,6-dihydro-2H-[1,4]oxazin-3-yl)-biphenyl-3-carbonitrile formate,
5-(2',4'-Difluoro-biphenyl-3-yl)-5-methyl-5,6-dihydro-2H-[1,4]oxazin-3-ylamine,
5-(2',5'-Dichloro-biphenyl-3-yl)-5-methyl-5,6-dihydro-2H-[1,4]oxazin-3-ylamine formate,
5-(2'-Chloro-biphenyl-3-yl)-5-methyl-5,6-dihydro-2H-[1,4]
oxazin-3-ylamine,
5-(2-Fluoro-5-pyrimidin-5-yl-phenyl)-5-methyl-5,6-dihydro-2H-[1,4]oxazin-3-ylamine,
5-(3-(2,6-difluoropyridin-3-yl)phenyl)-5-methyl-5,6-dihydro-2H-1,4-oxazin-3-amine trifluoroacetate,
5-(3-(2-fluoropyridin-3-yl)phenyl)-5-methyl-5,6-dihydro-2H-1,4-oxazin-3-amine trifluoroacetate,
5-(3-(5-amino-3-methyl-3,6-dihydro-2H-1,4-oxazin-3-yl)phenyl)nicotinonitrile trifluoroacetate,
5-(3',5'-Dichloro-6-fluoro-biphenyl-3-yl)-5-methyl-5,6-dihydro-2H-[1,4]oxazin-3-ylamine formate,
5-(3',5'-Dichloro-biphenyl-3-yl)-5-methyl-5,6-dihydro-2H-[1,4]oxazin-3-ylamine,
5-(3',5'-Difluoro-biphenyl-3-yl)-5-methyl-5,6-dihydro-2H-[1,4]oxazin-3-ylamine,
5-(3'-Amino-biphenyl-3-yl)-5-methyl-5,6-dihydro-2H-[1,4]
oxazin-3-ylamine,
5-(3-Benzo[1,3]dioxol-5-yl-phenyl)-5-methyl-5,6-dihydro-2H-[1,4]oxazin-3-ylamine formate,
5-(3'-Chloro-4'-fluoro-biphenyl-3-yl)-5-methyl-5,6-dihydro-2H-[1,4]oxazin-3-ylamine formate,
5-(3'-Chloro-5'-methoxy-biphenyl-3-yl)-5-methyl-5,6-dihydro-2H-[1,4]oxazin-3-ylamine formate,
5-(3'-Chloro-5'-methyl-biphenyl-3-yl)-5-methyl-5,6-dihydro-2H-[1,4]oxazin-3-ylamine formate,
5-(3'-Chloro-biphenyl-3-yl)-5-methyl-5,6-dihydro-2H-[1,4]
oxazin-3-ylamine formate,
5-(3'-Difluoromethoxy-biphenyl-3-yl)-5-methyl-5,6-dihydro-2H-[1,4]oxazin-3-ylamine formate,
5-(3'-Ethoxy-biphenyl-3-yl)-5-methyl-5,6-dihydro-2H-[1,4]
oxazin-3-ylamine,
5-(4'-Chloro-3'-methyl-biphenyl-3-yl)-5-methyl-5,6-dihydro-2H-[1,4]oxazin-3-ylamine formate,
5-(4-Difluoromethoxy-3-methyl-phenyl)-5-(3-pyridin-3-yl-phenyl)-5,6-dihydro-2H-[1,4]oxazin-3-ylamine hydrochloride,
5-(4'-Fluoro-biphenyl-3-yl)-5-methyl-5,6-dihydro-2H-[1,4]
oxazin-3-ylamine formate,
5-(4'-tert-Butyl-biphenyl-3-yl)-5-methyl-5,6-dihydro-2H-[1,4]oxazin-3-ylamine formate, 5-(5'-Chloro-2'-fluoro-3'-methyl-biphenyl-3-yl)-5-methyl-5,6-dihydro-2H-[1,4]oxazin-3-ylamine formate,
5-(5'-Chloro-3'-trifluoromethyl-biphenyl-3-yl)-5-methyl-5,6-dihydro-2H-[1,4]oxazin-3-ylamine formate,
5-[3-(1H-Indol-5-yl)-phenyl]-5-methyl-5,6-dihydro-2H-[1,4]oxazin-3-ylamine formate,
5-[3-(2,2-Difluoro-benzo[1,3]dioxol-5-yl)-phenyl]-5-methyl-5,6-dihydro-2H-[1,4]oxazin-3-ylamine formate,
5-[3-(2,5-Dichloro-pyridin-3-yl)-phenyl]-5-methyl-5,6-dihydro-2H-[1,4]oxazin-3-ylamine formate,
5-[3-(2-Chloro-pyridin-4-yl)-phenyl]-5-methyl-5,6-dihydro-2H-[1,4]oxazin-3-ylamine formate,
5-[3-(3-Methoxy-prop-1-ynyl)-phenyl]-5-methyl-5,6-dihydro-2H-[1,4]oxazin-3-ylamine,
5-[3-(5-Chloro-1H-benzoimidazol-2-yl)-phenyl]-5-methyl-5,6-dihydro-2H-[1,4]oxazin-3-ylamine,
5-[3-(5-Chloro-pyridin-2-yl)-phenyl]-5-methyl-5,6-dihydro-2H-[1,4]oxazin-3-ylamine,
5-[3-(5-Chloro-pyridin-2-ylethynyl)-phenyl]-5-methyl-5,6-dihydro-2H-[1,4]oxazin-3-ylamine,
5-[3-(5-Chloro-pyridin-3-yl)-phenyl]-5-(4-difluoromethoxy-3-methyl-phenyl)-5,6-dihydro-2H-[1,4]oxazin-3-ylamine hydrochloride,
5-[3-(5-Chloro-pyridin-3-yl)-phenyl]-5-(6-difluoromethoxy-pyridin-3-yl)-5,6-dihydro-2H-[1,4]oxazin-3-ylamine hydrochloride,
5-[3-(5-Chloro-pyridin-3-yl)-phenyl]-5-methyl-5,6-dihydro-2H-[1,4]oxazin-3-ylamine,
5-[3-(5-Methoxy-pyridin-3-yl)-phenyl]-5-methyl-5,6-dihydro-2H-[1,4]oxazin-3-ylamine,
5-[3-(6-Chloro-1H-indol-2-yl)-phenyl]-5-methyl-5,6-dihydro-2H-[1,4]oxazin-3-ylamine hydrochloride formate,
5-[3-(6-Chloro-benzooxazol-2-yl)-phenyl]-5-methyl-5,6-dihydro-2H-[1,4]oxazin-3-ylamine hydrochloride,
5-[3-(6-Chloro-pyridin-3-yl)-phenyl]-5-(4-difluoromethoxy-3-methyl-phenyl)-5,6-dihydro-2H-[1,4]oxazin-3-ylamine hydrochloride,
5-Methyl-5-(2',3',5'-trichloro-biphenyl-3-yl)-5,6-dihydro-2H-[1,4]oxazin-3-ylamine formate,
5-Methyl-5-(3-pyrimidin-5-yl-phenyl)-5,6-dihydro-2H-[1,4]oxazin-3-ylamine,
5-Methyl-5-(3-thiophen-3-yl-phenyl)-5,6-dihydro-2H-[1,4]oxazin-3-ylamine formate,
5-Methyl-5-(3'-trifluoromethoxy-biphenyl-3-yl)-5,6-dihydro-2H-[1,4]oxazin-3-ylamine formate, and
5-Methyl-5-[3-(1-methyl-1H-indazol-4-yl)-phenyl]-5,6-dihydro-2H-[1,4]oxazin-3-ylamine formate.

A certain embodiment of the invention provides compounds as described herein, selected from the group consisting of
5-(6-Difluoromethoxy-pyridin-3-yl)-5-[3-(5-methoxy-pyridin-3-yl)-phenyl]-5,6-dihydro-2H-[1,4]oxazin-3-ylamine hydrochloride,
(R)-5-(3',5'-Dichloro-4-fluoro-biphenyl-3-yl)-5-methyl-5,6-dihydro-2H-[1,4]oxazin-3-ylamine formate,
5-(3-(2,6-difluoropyridin-3-yl)phenyl)-5-methyl-5,6-dihydro-2H-1,4-oxazin-3-amine trifluoroacetate,
5-(3-(2-fluoropyridin-3-yl)phenyl)-5-methyl-5,6-dihydro-2H-1,4-oxazin-3-amine trifluoroacetate,
5-(3-(5-amino-3-methyl-3,6-dihydro-2H-1,4-oxazin-3-yl)phenyl)nicotinonitrile trifluoroacetate,
5-(4-Difluoromethoxy-3-methyl-phenyl)-5-(3-pyridin-3-yl-phenyl)-5,6-dihydro-2H-[1,4]oxazin-3-ylamine hydrochloride,
5-[3-(5-Chloro-pyridin-2-ylethynyl)-phenyl]-5-methyl-5,6-dihydro-2H-[1,4]oxazin-3-ylamine,
5-[3-(5-Chloro-pyridin-3-yl)-phenyl]-5-(4-difluoromethoxy-3-methyl-phenyl)-5,6-dihydro-2H-[1,4]oxazin-3-ylamine hydrochloride,
5-[3-(5-Chloro-pyridin-3-yl)-phenyl]-5-(6-difluoromethoxy-pyridin-3-yl)-5,6-dihydro-2H-[1,4]oxazin-3-ylamine hydrochloride,
5-[3-(5-Chloro-pyridin-3-yl)-phenyl]-5-methyl-5,6-dihydro-2H-[1,4]oxazin-3-ylamine, and
5-[3-(6-Chloro-benzooxazol-2-yl)-phenyl]-5-methyl-5,6-dihydro-2H-[1,4]oxazin-3-ylamine hydrochloride.

A certain embodiment of the invention provides a process to synthesize a compound of formula I as described herein, which process comprises reacting a compound of formula XII to a compound of formula I

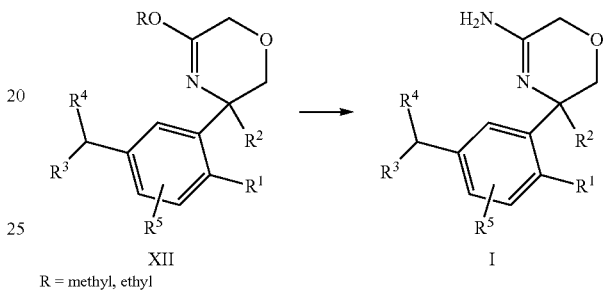

R = methyl, ethyl wherein $R^1$, $R^2$, $R^3$, $R^4$, $R^5$ are as defined herein.

A certain embodiment of the invention provides a compound of formula I as described herein, whenever prepared by a process as defined above.

A certain embodiment of the invention provides a compound of formula I as described herein for use as therapeutically active substance.

A certain embodiment of the invention provides a compound of formula I as described herein for the use as inhibitor of BACE1 and/or BACE2 activity.

A certain embodiment of the invention provides a compound of formula I as described herein for the use as inhibitor of BACE1 activity.

A certain embodiment of the invention provides a compound of formula I as described herein for the use as inhibitor of BACE2 activity.

A certain embodiment of the invention provides a compound of formula I as described herein for the use as inhibitor of BACE1 and BACE2 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a compound of formula I as described herein for the use as therapeutically active substance for the therapeutic and/or prophylactic treatment of diabetes, particularly type 2 diabetes.

A certain embodiment of the invention provides a compound of formula I as described herein for the use as therapeutically active substance for the therapeutic and/or prophylactic treatment of diabetes.

A certain embodiment of the invention provides a compound of formula I as described herein for the use as therapeutically active substance for the therapeutic and/or prophylactic treatment of Alzheimer's disease, diabetes or type 2 diabetes.

A certain embodiment of the invention provides a compound of formula I as described herein for the use as therapeutically active substance for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a pharmaceutical composition containing a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 and/or BACE2 activity.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the use in inhibition of BACE2 activity.

A certain embodiment of the invention provides the use of a compound of formula I as described herein for the manufacture of a medicament for the use in inhibition of BACE1 and BACE2 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of diabetes, particularly type 2 diabetes.

A certain embodiment of the invention provides the use of a compound of formula I as described herein for the manufacture of a medicament for the therapeutic and/or prophylactic treatment of diabetes.

A certain embodiment of the invention provides the use of a compound of formula I as described herein for the manufacture of a medicament for the therapeutic and/or prophylactic treatment of Alzheimer's disease, diabetes or type 2 diabetes.

A certain embodiment of the invention provides a compound of formula I as described herein for the use in inhibition of BACE1 and/or BACE2 activity.

A certain embodiment of the invention provides a compound of formula I as described herein for the use in inhibition of BACE1 activity.

A certain embodiment of the invention provides a compound of formula I as described herein for the use in inhibition of BACE2 activity.

A certain embodiment of the invention provides a compound of formula I as described herein for the use in inhibition of BACE1 and BACE2 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention provides a compound of formula I as described herein for the use in the therapeutic and/or prophylactic treatment of Alzheimer's disease.

A certain embodiment of the invention provides a compound of formula I as described herein for the use in the therapeutic and/or prophylactic treatment of diabetes, particularly type 2 diabetes.

A certain embodiment of the invention provides a compound of formula I as described herein for the use in the therapeutic and/or prophylactic treatment of diabetes.

A certain embodiment of the invention provides a compound of formula I as described herein for the use in the therapeutic and/or prophylactic treatment of Alzheimer's disease, diabetes or type 2 diabetes.

A certain embodiment of the invention provides a method for the use in inhibition of BACE1 and/or BACE2 activity, particularly for the therapeutic and/or prophylactic treatment of diseases and disorders characterized by elevated β-amyloid levels and/or β-amyloid oligomers and/or β-amyloid plaques and further deposits, Alzheimer's disease, diabetes or type 2 diabetes, which method comprises administering compound of formula I as described herein to a human being or animal.

A certain embodiment of the invention provides a method for the use in the therapeutic and/or prophylactic treatment of Alzheimer's disease, diabetes or type 2 diabetes, which method comprises administering a compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The skilled person in the art will recognize that the compounds of formula I can exist in tautomeric forms, e.g. in the following tautomeric form:

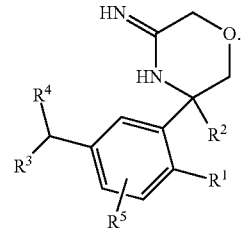

Id

All tautomeric forms are encompassed in the present invention.

The compounds of formula I can contain one or more asymmetric centers and can therefore occur as racemates, racemic mixtures, single enantiomers, diastereomeric mixtures and individual diastereomers. Additional asymmetric centers can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Preferred examples of isomers of a compound of formula I is a compound of formula Ia or a compound of formula Ib, in particular Ib, wherein the residues have the meaning as described in any of the embodiments.

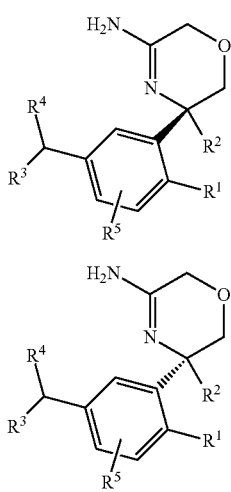

In the embodiments, where optically pure enantiomers are provided, optically pure enantiomer means that the compound contains >90% of the desired isomer by weight, preferably >95% of the desired isomer by weight, or more preferably >99% of the desired isomer by weight, said weight percent based upon the total weight of the isomer(s) of the compound. Chirally pure or chirally enriched compounds can be prepared by chirally selective synthesis or by separation of enantiomers. The separation of enantiomers can be carried out on the final product or alternatively on a suitable intermediate.

The compounds of formula I can be prepared in accordance with the following schemes. The starting material is commercially available or can be prepared in accordance with known methods. Any previously defined residues and variables will continue to have the previously defined meaning unless otherwise indicated.

The compounds of formula I can be prepared through a number of synthetic routes for example as illustrated in schemes 1-4. The preparation of compounds of formula I of the present invention can be carried out in sequential or convergent synthetic routes. Syntheses of the compounds of the invention are shown in the following schemes 1-4. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes described below, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The compounds of formula I described in the schemes 1-4 can be isolated and purified by methods known to those skilled in the art, such as but not limited to ion exchange chromatography, solid phase extraction, liquid-liquid extraction, silica chromatography, crystallization and preparative high performance liquid chromatography (HPLC).

According to scheme 1, ketones of general formula IV (wherein Y has the meaning of a leaving group like halo, e.g. bromide) can be reacted with cyanides, like potassium cyanide, together with ammonium carbonate in polar solvents such as alcohols, e.g. ethanol, water or tetrahydrofuran and mixtures thereof, to form hydantoins of formula V. The hydantoin can then be treated with water along with a base such as sodium hydroxide or a strong acid such as sulfuric acid at temperatures ranging from ambient temperature to reflux to yield the amino acid of formula VI. The amino alcohol of formula VIII is obtained by esterification of the acid of formula VI with a lower alcohol, such as methanol or ethanol, followed by reduction of the resulting amino ester of formula VII with lithium aluminum hydride or other suitable reagents both steps performed under conditions known to those skilled in the art. N-Acylation of the aminoalcohol of formula VIII can be effected by condensation with halogenated acetic acid derivatives, such as chloroacetic acid using condensation reagents like benzotriazole derivatives, e.g. O-(benzotriazol-1-yl)-N,N,N',N'-tetramethyluronium-hexafluorophosphate (HBTU) and the like in inert solvents, or with acid chloride derivatives such as chloroacetyl chloride in presence of a base such as triethylamine in an inert solvent both methods under conditions known to those skilled in the art and yielding acetyl derivatives of formula IX. Lactams of formula X can be prepared by cyclization of the alcohol of formula IX with base, such as potassium tert-butylate, in solvents such as tert-butanol at temperatures ranging from room temperature to reflux. The iminoether of formula XI can be synthesized by treatment of the lactam of formula X with alkyl oxonium salts, e.g. trimethyloxonium tetrafluoroborate or triethyloxonium tetrafluoroborate. Non commercial ketones of general formula IV can be synthesized by routes such as depicted in scheme 1 or by other routes known to those skilled in the art. Weinreb amides of formula III can be obtained by standard condensation reactions of the acids of formula II with N,O-dimethylhydroxylamine or by the intermediate formation of the acyl chloride of acids of formula II using an agent such as oxalyl chloride or thionyl chloride using standard conditions such as triethylamine/dichloromethane. The amides of formula III can be reacted with organometallics such as methylmagnesium chloride in inert aprotic solvents such as tetrahydrofuran or diethyl ether to yield the desired ketones of formula IV.

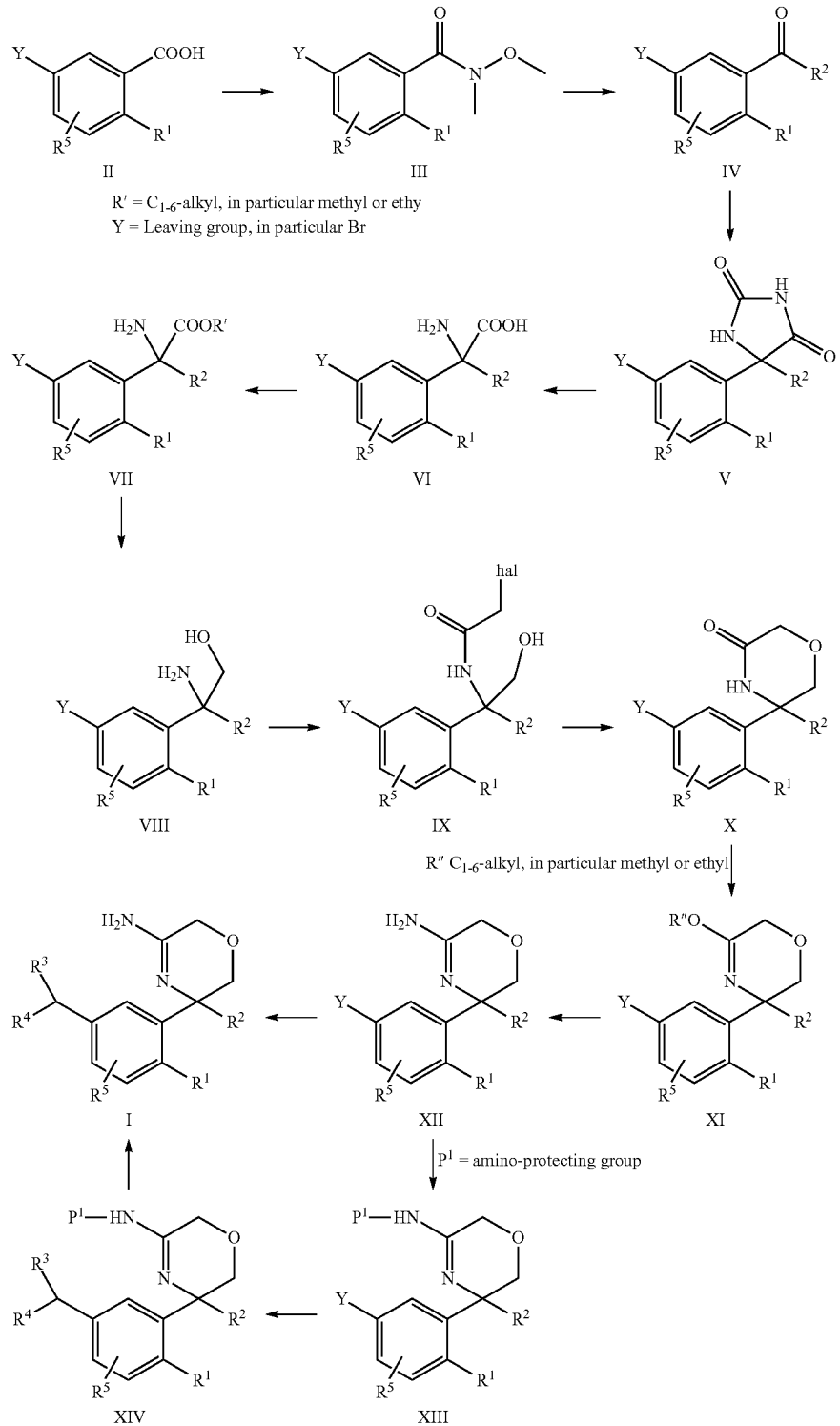

Scheme 1: Syntheses of compounds of formula I.

Treatment of the iminoether of formula XI with ammonium salts such as ammonium chloride in polar solvents like alcohols, e.g. methanol yields the intermediate amine of formula XII.

Palladium-catalyzed cross coupling between organoboronic acids or esters thereof and compounds of formula XII under conditions (Suzuki-Miyaura-coupling) known to those skilled in the art yields the final compound of formula I.

Alternatively, compounds of formula XII can be used in their protected form, e.g. as triphenylmethyl derivatives, preferably by 4,4'-dimethoxytriphenymethyl (DMTr). The introduction of the protecting group can be performed in inert solvents, e.g. dichloromethane, at temperatures between 0° C. and room temperature to yield the N-protected amine of formula XIII.

Palladium-catalyzed cross coupling between organoboronic acids or esters thereof and compounds of formula XIII under conditions (Suzuki-Miyaura-coupling) known to those skilled in the art yields compounds of formula XIV.

The N-protecting group in compounds of formula XIV can be cleaved by acids like trifluoroacetic acid in inert solvents, e.g. dichloromethane, at temperatures between 0 and 23° C. to yield compounds of formula I.

Alternatively, compounds of formula I can be obtained as follows: According to scheme 2, the formation of a methyltriphenyl-phosphonium ylide produced from the corresponding phosphonium salts by strong base such as butyllithium in solvents such as tetrahydrofuran or toluene at temperatures between −78° C. and 0° C. followed by addition of the ketone of formula IV yields the desired alkenes of formula XV. The alkenes can then be reacted with a mixture of silver cyanate and iodine in solvents such as diethyl ether or mixtures of ethyl acetate and acetonitrile. The resultant iodoisocyanates of formulas XVI can then be heated with alcohols like tert-butanol and a base, like triethylamine or N,N-Diisopropyl-ethylamin (Huenig's base), to yield the oxazolidinones of formula XVII. Hydrolysis of the resultant oxazolidinone of formula XVII with aqueous base like lithium hydroxide yields the aminoalcohol of formula VIII.

N-Acylation of the aminoalcohol of formula VIII can be effected by condensation with halogenated acetic acid derivatives, such as chloroacetic acid using condensation reagents like benzotriazole derivatives, e.g. O-(benzotriazol-1-yl)-N,N,N',N'-tetramethyluronium-hexafluorophosphate (HBTU) and the like in inert solvents, or with acid chloride derivatives such as chloroacetylchloride in presence of a base such as triethylamine in an inert solvent, both methods under conditions known to those skilled in the art and yielding acetyl derivatives of formula IX. Lactams of formula X can be prepared by cyclization of the alcohol of formula IX with base, such as potassium tert-butylate, in solvents such as tert-butanol at temperatures ranging from room temperature to reflux.

Scheme 2: Synthesis of compounds of formula I via intermediates of formula XII.

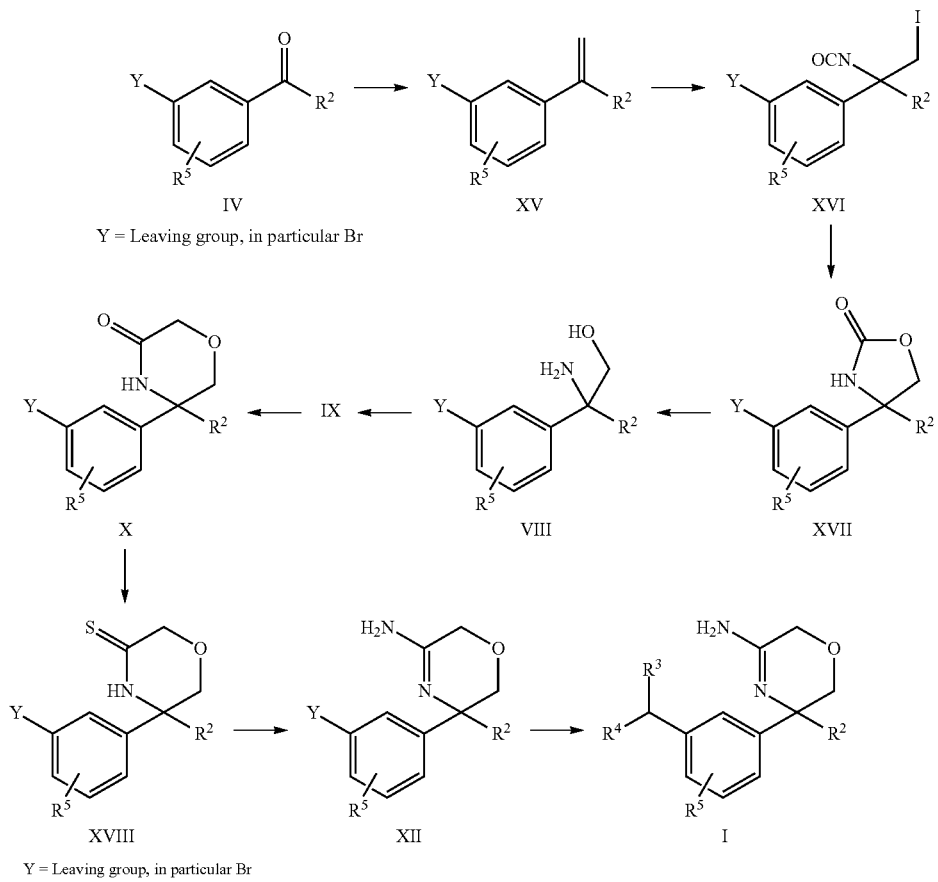

Y = Leaving group, in particular Br

Y = Leaving group, in particular Br

Further treatment of lactams of formula X with Lawesson's reagent under conditions known to those skilled in the art to yields the thiolactam of formula XVIII. Treatment of the thiolactam of formula XVIII either with oxidizing reagents, like tert-butyl hydroperoxide followed by ammonolysis, or by treatment with ammonia in methanol alone yields the final compound of formula I.

Scheme 3: Alternative synthesis of compounds of formula I.

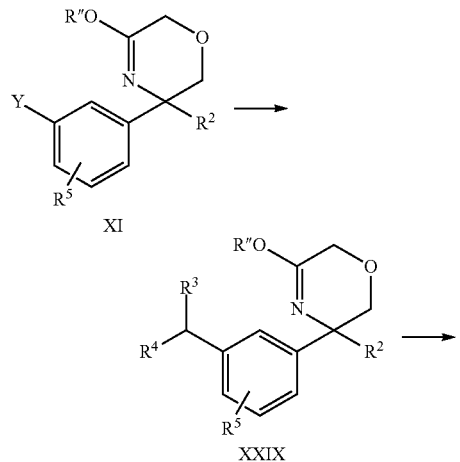

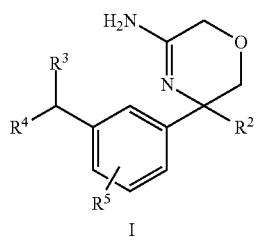

R'' = C$_{1-6}$-alkyl, in particular methyl or ethy
Y = Leaving group, in particular Br An alternative pathway to synthesize compounds of formula I is depicted in Scheme 3. Palladium-catalyzed cross coupling between organoboronic acids or esters thereof and iminoethers of formula XI under conditions (Suzuki-Miyaura-coupling) known to those skilled in the art yields compounds of formula XXIX. Treatment of the iminoether of formula XXIX with ammonium salts such as ammonium chloride in polar solvents like alcohols, e.g. methanol, yields final compounds of formula I.

Scheme 4: Syntheses of alkyne (R$^3$ and R$^4$ together with the C to which they are attached form an alkyne) derivatives of formula I.

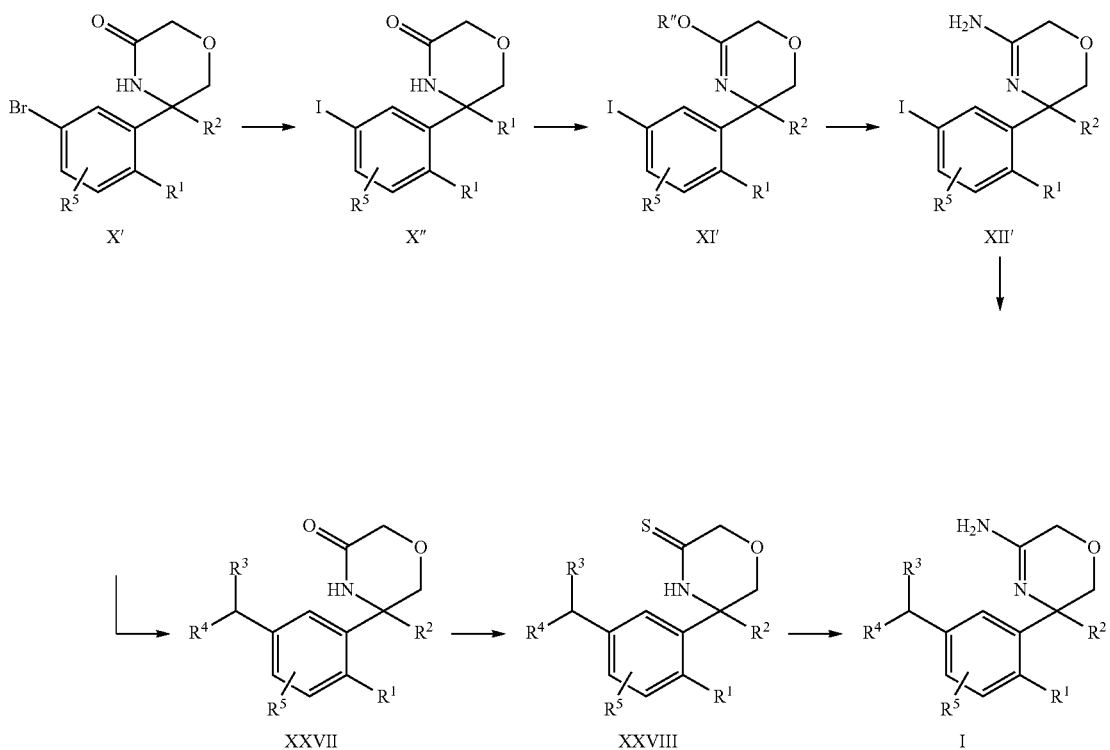

Compounds of formula I, wherein $R^3$ and $R^4$ together with the C to which they are attached form an alkyne, can be prepared as depicted in Scheme 4. The Sonogashira coupling of terminal alkynes with aryl bromides of formula X', iodides of formula X" or of formula XII' is performed with a palladium catalyst, e.g. bis(triphenyphosphine)-palladium(II) chloride, a copper(I) co-catalyst, e.g. copper(I)iodide, and an amine base, e.g. triethylamine, conditions known to those skilled in the art. In some cases the use of iodides is preferred over the use of bromides. The conversion of arylbromides of formula X' into the corresponding iodides of formula X" can be accomplished utilizing a catalyst system which comprises copper(I)iodide and a 1,2- or 1,3-diamine ligand as described by A. Klapars and S. L. Buchwald in JACS 2002, 124(50), 14844.

The further transformations leading to compounds of formula I via the iminoethers of formula XI' or thiolactams of formula XXVIII are performed as already described above.

Compounds of formula I, wherein $R^3$ and $R^4$ together with the C to which they are attached form for example a benzene-fused 5-membered heterocycle can be prepared following Scheme 5. Suzuki coupling of compounds of formula XXIX with vinylic boronic acid derivatives under conditions known to those skilled in the art yields the olefins of formula XX. The reaction sequence leading to lactams of formula X' is accomplished by procedures already described above.

Cleavage of the dioxolane derivatives of formula X' and oxidation of the transiently formed aldehyde to acids of formula XXVI can be performed in one step utilizing an acidic oxidative reagent like e.g. potassium monopersulphate.

Acids of formula XXVI can the be transformed into 5-membered heterocycles by general methods known to those skilled in the art.

Thereafter, the reaction sequence leading to compounds of formula I follows procedures already described above, e.g. via thiolactams of formula XVIII.

Scheme 5: Synthesis of compounds of formula I.

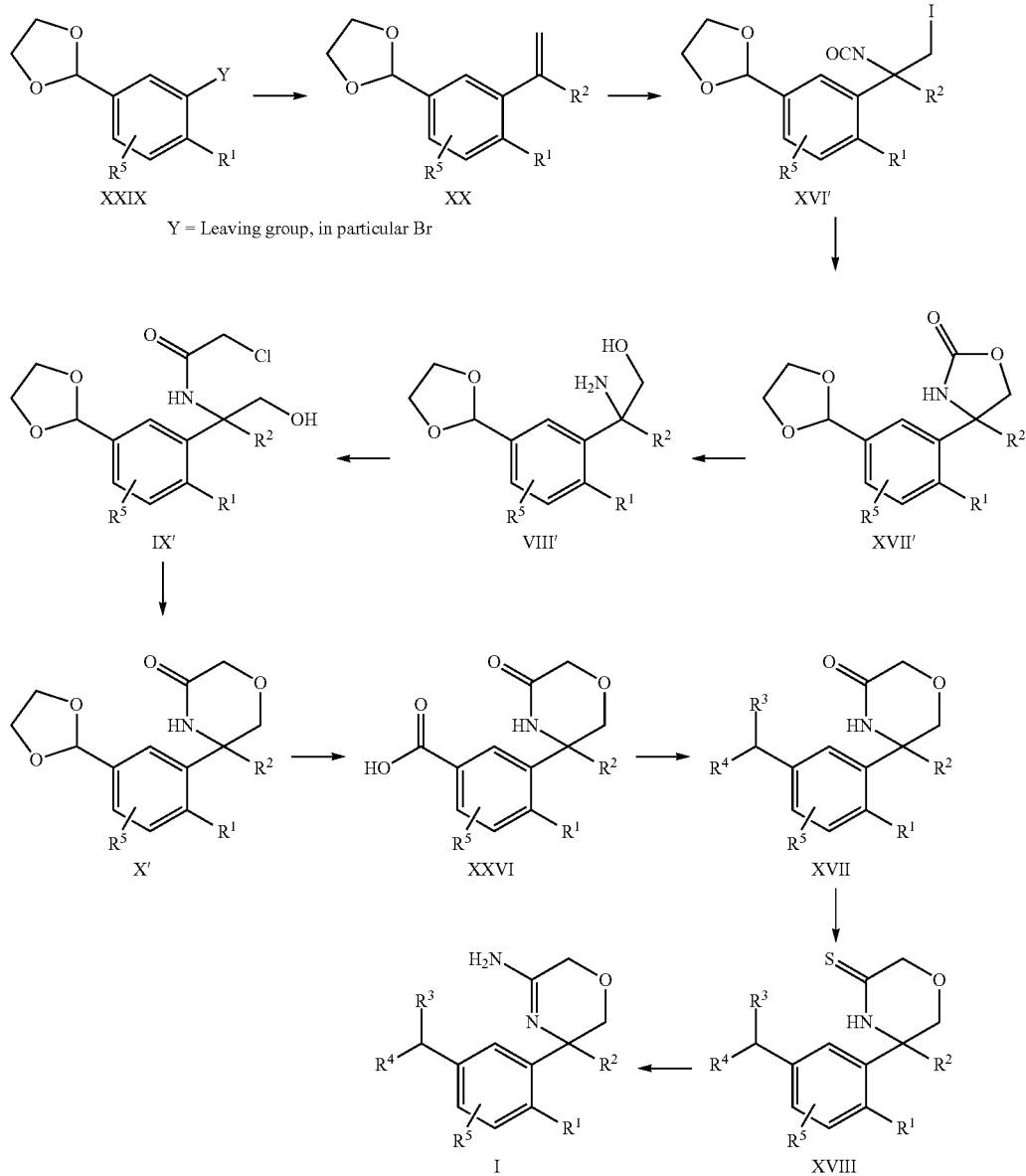

Y = Leaving group, in particular Br

Optionally, acids of formula XXVI can be obtained by palladium-catalyzed carbonylation of compounds of formula X with, e.g. 1,1'-bis(diphenylphosphino)ferrocene-palladium (II) dichloride as the catalyst, in presence of triethylamine. Preferably the reaction is performed in alcohols, e.g. methanol or ethanol, to yield the corresponding esters which are saponified under standard conditions to acids of formula XXVI.

Scheme 6: Alternative enantioselective synthesis of amino esters of formula VII'.

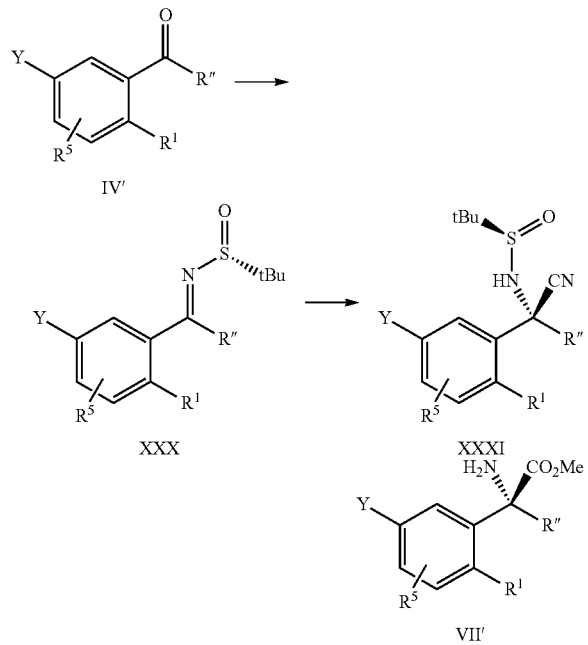

R" = $C_{1-6}$-alkyl, in particular methyl or ethy
Y = Leaving group, in particular Br As an alternative synthetic access to chiral amino esters of the general formula VII', the following route can be employed: Aromatic ketones of general formula IV' can be converted into the sulfinyl imine of general formula XXX in analogy to T. P. Tang & J. A. Ellman, J. Org. Chem. 1999, 64, 12, by condensation of the aryl ketone group and a sulfinamide, e.g. an alkyl sulfinamide, in this case most preferably (R)-(+)-tert-butylsulfinamide in the presence of a Lewis acid such as e.g. a titanium(IV)alkoxide, more preferably titanium (IV)ethoxide in a solvent such as an ether, e.g. diethyl ether or more preferably tetrahydrofuran.

The conversion of the sulfinyl imine XXX to the nitrile of general formula XXXI proceeds stereoselectively by the chiral directing group as described by Tang & Ellman or by A. Avenoza, J. H. Busto, F. Corzana, J. M. Peregrina, D. Sucunza, M. M. Zurbano in Synthesis 2005, (4), 575-578.

The sulfinyl imine of general formula XXXI can be treated with an mixed alkyl alkoxide aluminum cyanide reagent, e.g. ethylaluminium cyanoisopropoxide [EtAl(O-i-Pr)CN], in a solvent such as an ether, e.g. diethyl ether or more preferably tetrahydrofuran, at temperatures starting from −78° C. and eventually raising to −10° C., to generate the nitriles of general formula XXXIV as described e.g. by A. Avenoza, J. H. Busto, F. Corzana, J. M. Peregrina, D. Sucunza, M. M. Zurbano in Synthesis 2005, (4), 575-578.

Hydrolysis of the chiral directing group in the nitriles of general formula XXXI to give first the chiral amino nitriles can be accomplished with a mineral acid, e.g. sulfuric acid or preferably hydrochloric acid in a solvent such as an ether, e.g. diethyl ether, tetrahydrofuran or more preferably 1,4-dioxane, which is followed by another acidic reaction with a mineral acid, e.g. anhydrous hydrochloric acid or preferably sulfuric acid in a solvent such as an aliphatic alcohol, e.g. ethanol or more preferably methanol, at temperatures from 23 to 80° C., to give the chiral amino esters of general formula VII'.

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention can be derivatized at functional groups to provide derivatives which are capable of conversion back to the parent compound in vivo.

Pharmacological Tests

The compounds of formula I and their pharmaceutically acceptable salts possess valuable pharmacological properties. Compounds of the present invention are associated with inhibition of BACE1 and/or BACE2 activity. The compounds were investigated in accordance with the test given hereinafter.

Cellular Aβ-Lowering Assay:

Human HEK293 cells which are stably transfected with a vector expressing a cDNA of the human APP wt gene (APP695) were used to assess the potency of the compounds in a cellular assay. The cells were seeded in 96-well microtiter plates in cell culture medium (Iscove, plus 10% (v/v) fetal bovine serum, glutamine, penicillin/streptomycin) to about 80% confluence and the compounds were added at a 10× concentration in 1/10 volume of medium without FCS containing 8% DMSO (final concentration of DMSO was kept at 0.8% v/v). After 18-20 hrs incubation at 37° C. and 5% $CO_2$ in a humidified incubator the culture supernatant was harvested for the determination of Aβ40 concentrations. 96well ELISA plates (e.g., Nunc MaxiSorb) were coated with monoclonal antibody which specifically recognize the C-terminal end of Aβ40 (Brockhaus et al., NeuroReport 9, 1481-1486; 1998). After blocking of non-specific binding sites with e.g. 1% BSA and washing, the culture supernatants were added in suitable dilutions together with a horseradish peroxidase-coupled Aβ detection antibody (e.g., antibody 4G8, Senetek, Maryland Heights, Mo.) and incubated for 5 to 7 hrs. Subsequently the wells of the microtiter plate were washed extensively with Tris-buffered saline containing 0.05% Tween 20 and the assay was developed with tetramethylbenzidine/ H₂O₂ in citric acid buffer. After stopping the reaction with one volume 1 N H$_2$SO$_4$ the reaction was measured in an ELISA reader at 450 nm wavelength. The concentrations of Aβ in the culture supernatants were calculated from a standard curve obtained with known amounts of pure Aβ peptide.

Assay for BACE Inhibition by Measuring Cellular TMEM27 Cleavage:

The assay uses the principle of inhibition of human TMEM27 cleavage by endogenous cellular BACE2 in the Ins1e rat cell line and shedding from the cell surface into the culture medium, followed by detection in an ELISA assay. Inhibition of BACE2 prevents the cleavage and shedding in a dose-dependent manner.

The stable cell line "INS-TMEM27" represents an INS1e-derived cell line with inducible expression (using the TetOn system) of full-length hTMEM27 in a doxycycline-dependent manner. The cells are cultured throughout the experiment in RPMI1640+Glutamax (Invitrogen) Penicillin/Streptomycin, 10% Fetal bovine serum, 100 mM pyruvate, 5 mM beta-mercatptoethanol, 100 micrograms/ml G418 and 100 microgram/ml hygromycin and are grown inadherent culture at 37° C. in a standard CO$_2$ cell culture incubator.

INS-TMEM27 cells are seeded in 96-well plates. After 2 days in culture, BACE2 inhibitor is added in a range of concentrations as required by the assay and after a further two hours, doxycycline is added to a final concentration of 500 ng/ml. The cells are incubated for a further 46 hours and the supernatant harvested for detection of shed TMEM27.

An ELISA assay (using a pair of mouse anti-human-TMEM27 antibodies, raised against the extracellular domain of TMEM27) is used for detection of TMEM27 in the culture medium. An $EC_{50}$ for BACE2 inhibition is calculated using the ELISA readout for each inhibitor concentration with standard curve-fitting software such as XLFit for the Excel spreadsheet program.

TABLE 1

IC$_{50}$ values of selected examples

| Exam. | Structure | BACE1 IC$_{50}$ [μM] | BACE2 IC$_{50}$ [μM] |
|---|---|---|---|
| 1 | 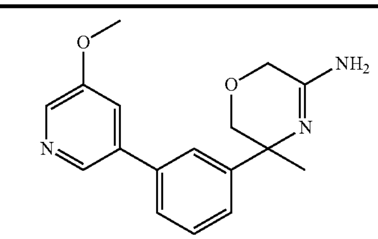 | 0.100 | |
| 2 | 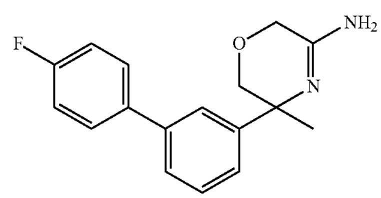 [SMILES: CC1(c2cccc(-c3ccc(F)cc3)c2)COCC(N)=N1] | 1.17 | — |
| 3 | 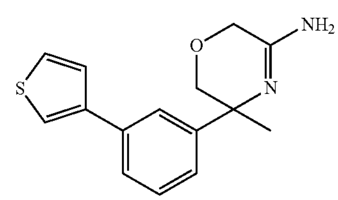 [SMILES: CC1(c2cccc(-c3ccsc3)c2)COCC(N)=N1] | 1.06 | — |
| 4 | 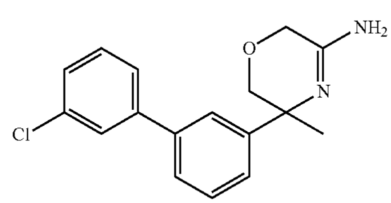 [SMILES: CC1(c2cccc(-c3cccc(Cl)c3)c2)COCC(N)=N1] | 0.39 | — |
| 5 | 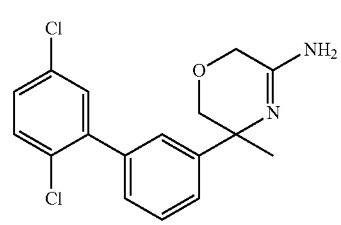 [SMILES: CC1(c2cccc(-c3cc(Cl)ccc3Cl)c2)COCC(N)=N1] | 1.09 | — |

TABLE 1-continued

IC$_{50}$ values of selected examples

| Exam. | Structure | BACE1 IC$_{50}$ [µM] | BACE2 IC$_{50}$ [µM] |
|---|---|---|---|
| 6 | 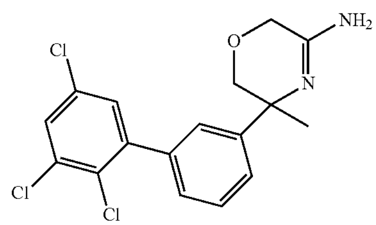 [SMILES: CC1(c2cccc(-c3cc(Cl)cc(Cl)c3Cl)c2)COCC(N)=N1] | 4.06 | — |
| 7 | 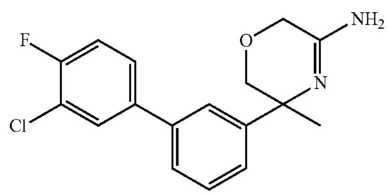 [SMILES: CC1(c2cccc(-c3ccc(F)c(Cl)c3)c2)COCC(N)=N1] | 0.65 | — |
| 8 | 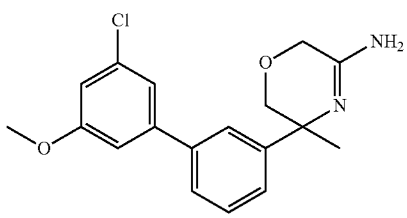 [SMILES: COc1cc(Cl)cc(-c2cccc(C3(C)COCC(N)=N3)c2)c1] | 1.49 | — |
| 9 | 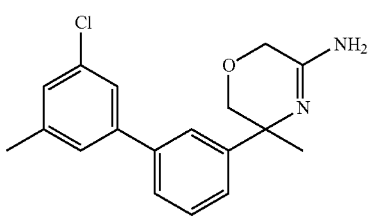 [SMILES: Cc1cc(Cl)cc(-c2cccc(C3(C)COCC(N)=N3)c2)c1] | 2.48 | 1.11 |
| 10 | 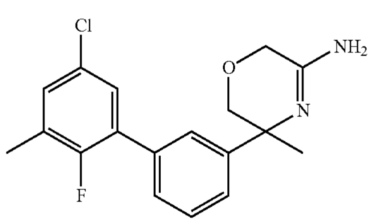 [SMILES: Cc1cc(Cl)cc(-c2cccc(C3(C)COCC(N)=N3)c2)c1F] | 1.50 | — |
| 11 | 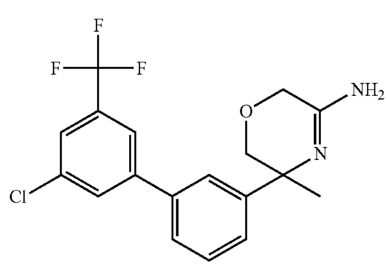 [SMILES: CC1(c2cccc(-c3cc(Cl)cc(C(F)(F)F)c3)c2)COCC(N)=N1] | 1.84 | — |

TABLE 1-continued

IC$_{50}$ values of selected examples

| Exam. | Structure | BACE1 IC$_{50}$ [μM] | BACE2 IC$_{50}$ [μM] |
|---|---|---|---|
| 12 | 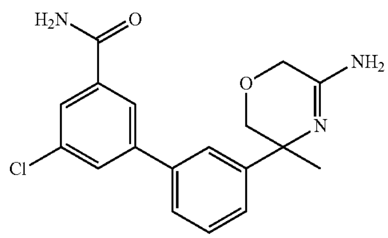 [SMILES: CC1(c2cccc(-c3cc(Cl)cc(C(N)=O)c3)c2)COCC(N)=N1] | 1.12 | — |
| 13 | 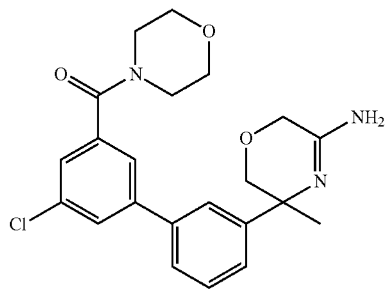 [SMILES: CC1(c2cccc(-c3cc(Cl)cc(C(=O)N4CCOCC4)c3)c2)COCC(N)=N1] | 2.39 | — |
| 14 | 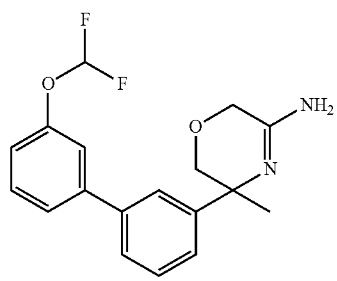 [SMILES: CC1(c2cccc(-c3cccc(OC(F)F)c3)c2)COCC(N)=N1] | 0.48 | — |
| 15 | 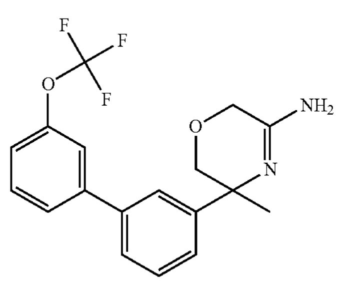 [SMILES: CC1(c2cccc(-c3cccc(OC(F)(F)F)c3)c2)COCC(N)=N1] | 2.31 | — |
| 16 | 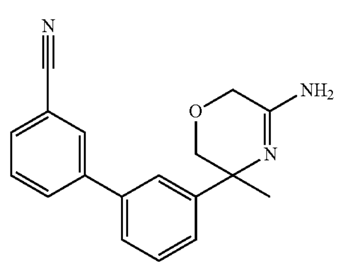 [SMILES: CC1(c2cccc(-c3cccc(C#N)c3)c2)COCC(N)=N1] | .28 | — |

TABLE 1-continued

IC₅₀ values of selected examples

| Exam. | Structure | BACE1 IC$_{50}$ [μM] | BACE2 IC$_{50}$ [μM] |
|---|---|---|---|
| 17 | 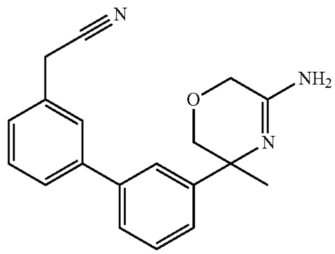 [SMILES: CC1(c2cccc(-c3cccc(CC#N)c3)c2)COCC(N)=N1] | 1.06 | |
| 18 | 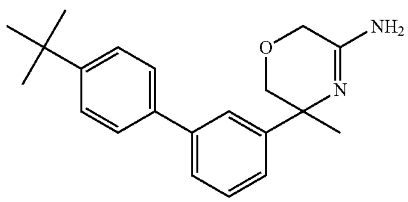 [SMILES: CC(C)(C)c1ccc(-c2cccc(C3(C)COCC(N)=N3)c2)cc1] | 6.12 | — |
| 19 | 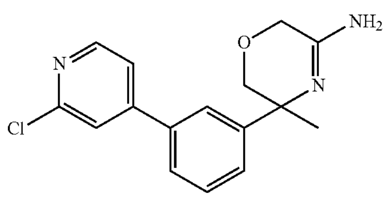 [SMILES: CC1(c2cccc(-c3ccnc(Cl)c3)c2)COCC(N)=N1] | 1.06 | — |
| 20 | 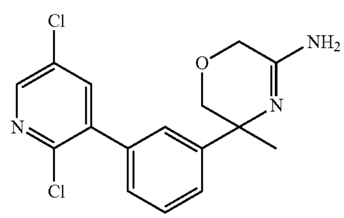 [SMILES: CC1(c2cccc(-c3cc(Cl)cnc3Cl)c2)COCC(N)=N1] | 0.49 | — |
| 21 | 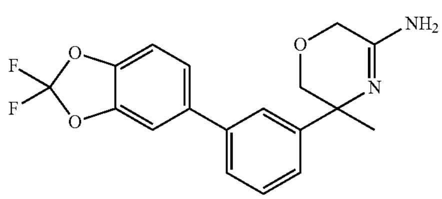 [SMILES: CC1(c2cccc(-c3ccc4c(c3)OC(F)(F)O4)c2)COCC(N)=N1] | 4.55 | — |
| 22 | 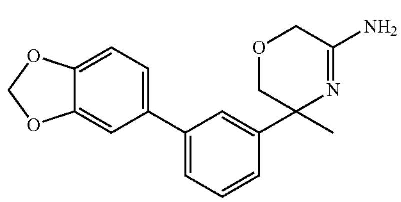 [SMILES: CC1(c2cccc(-c3ccc4c(c3)OCO4)c2)COCC(N)=N1] | 1.06 | — |
| 23 | 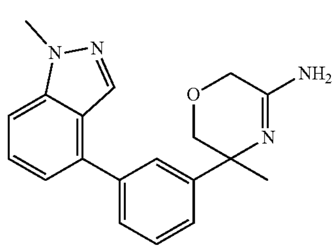 [SMILES: Cn1ncc2c(-c3cccc(C4(C)COCC(N)=N4)c3)cccc21] | 3.66 | — |

TABLE 1-continued
IC$_{50}$ values of selected examples
| Exam. | Structure | BACE1 IC$_{50}$ [μM] | BACE2 IC$_{50}$ [μM] |
|---|---|---|---|
| 24 | 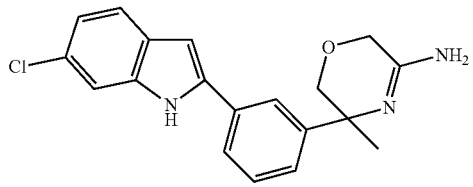 [SMILES: CC1(c2cccc(-c3cc4ccc(Cl)cc4[nH]3)c2)COCC(N)=N1] | 12.73 | — |
| 25 | 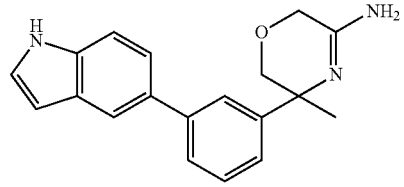 [SMILES: CC1(c2cccc(-c3ccc4[nH]ccc4c3)c2)COCC(N)=N1] | 6.41 | — |
| 26 | 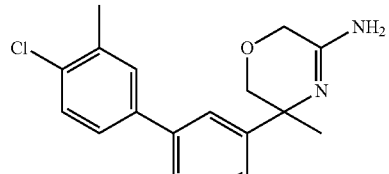 | 12.96 | — |
| 27 | 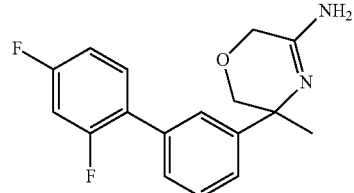 | 1.06 | — |
| 28 | 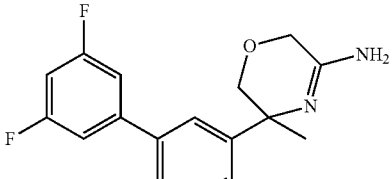 | 2.08 | — |
| 29 | 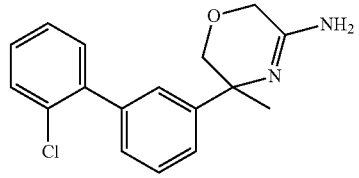 [SMILES: CC1(c2cccc(-c3ccccc3Cl)c2)COCC(N)=N1] | 1.06 | — |
| 30 | 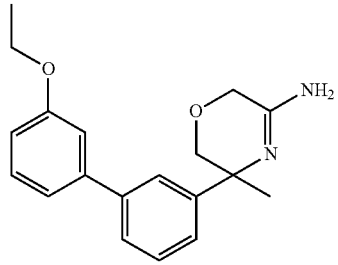 [SMILES: CCOc1cccc(-c2cccc(C3(C)COCC(N)=N3)c2)c1] | 9.10 | — |

TABLE 1-continued

IC₅₀ values of selected examples

| Exam. | Structure | BACE1 IC$_{50}$ [μM] | BACE2 IC$_{50}$ [μM] |
|---|---|---|---|
| 31 | 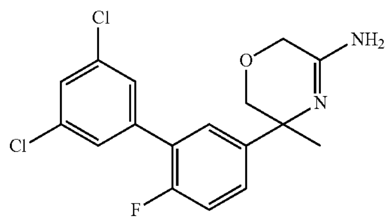 [SMILES: CC1(c2ccc(F)c(-c3cc(Cl)cc(Cl)c3)c2)COCC(N)=N1] | 1.00 | — |
| 32 | 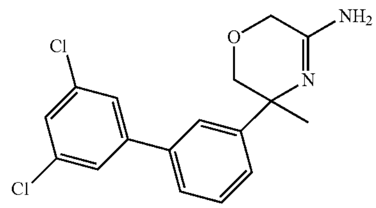 [SMILES: CC1(c2cccc(-c3cc(Cl)cc(Cl)c3)c2)COCC(N)=N1] | 1.53 | 0.47 |
| 33 | 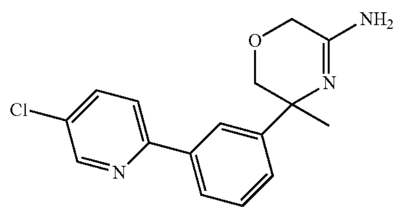 [SMILES: CC1(c2cccc(-c3ccc(Cl)cn3)c2)COCC(N)=N1] | 12.55 | — |
| 34 | 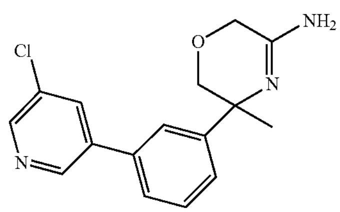 [SMILES: CC1(c2cccc(-c3cncc(Cl)c3)c2)COCC(N)=N1] | 0.39 | — |
| 35 | 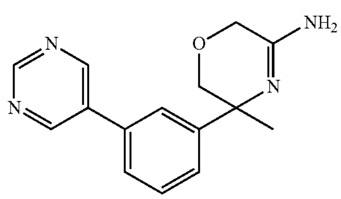 [SMILES: CC1(c2cccc(-c3cncnc3)c2)COCC(N)=N1] | 0.71 | — |
| 36 | 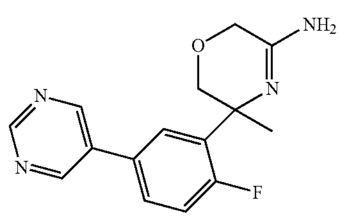 [SMILES: CC1(c2cc(-c3cncnc3)ccc2F)COCC(N)=N1] | 0.98 | — |
| 37 | 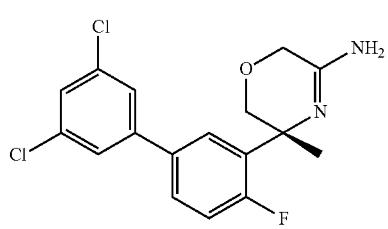 [SMILES: C[C@@]1(c2cc(-c3cc(Cl)cc(Cl)c3)ccc2F)COCC(N)=N1] | 0.51 | 0.12 |

TABLE 1-continued
IC$_{50}$ values of selected examples
| Exam. | Structure | BACE1 IC$_{50}$ [μM] | BACE2 IC$_{50}$ [μM] |
|---|---|---|---|
| 38 | 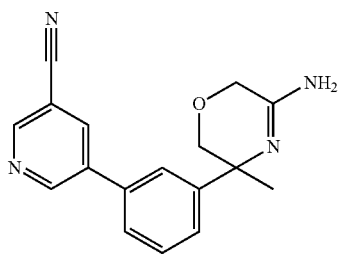 [SMILES: CC1(c2cccc(-c3cncc(C#N)c3)c2)COCC(N)=N1] | 0.31 | — |
| 39 | 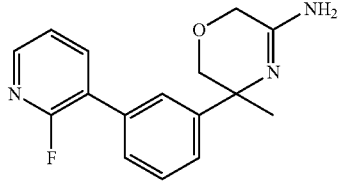 [SMILES: CC1(c2cccc(-c3cccnc3F)c2)COCC(N)=N1] | 0.28 | — |
| 40 | 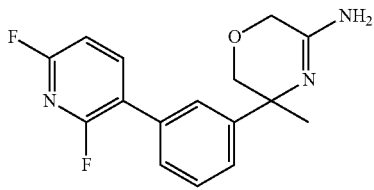 [SMILES: CC1(c2cccc(-c3ccc(F)nc3F)c2)COCC(N)=N1] | 0.53 | — |
| 41 | 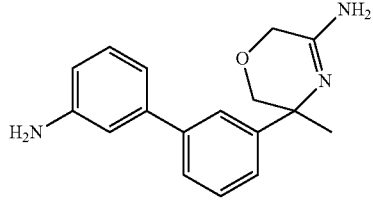 [SMILES: CC1(c2cccc(-c3cccc(N)c3)c2)COCC(N)=N1] | 3.07 | — |
| 42 | 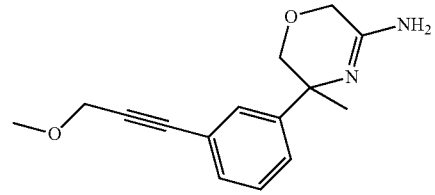 [SMILES: COCC#Cc1cccc(C2(C)COCC(N)=N2)c1] | 1.06 | — |
| 43 | 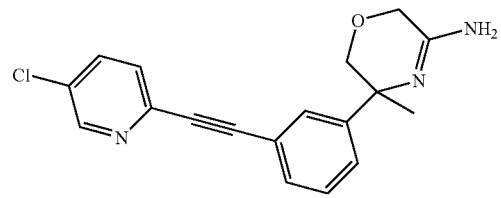 [SMILES: CC1(c2cccc(C#Cc3ccc(Cl)cn3)c2)COCC(N)=N1] | 0.30 | — |

TABLE 1-continued

IC$_{50}$ values of selected examples

| Exam. | Structure | BACE1 IC$_{50}$ [μM] | BACE2 IC$_{50}$ [μM] |
|---|---|---|---|
| 44 | 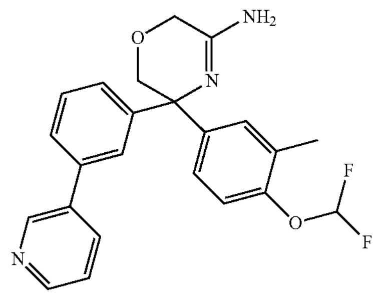 [SMILES: Cc1cc(C2(c3cccc(-c4cccnc4)c3)COCC(N)=N2)ccc1OC(F)F] | 0.06 | — |
| 45 | 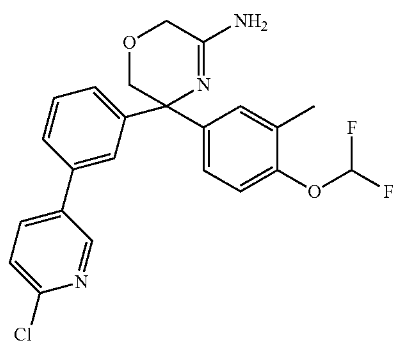 [SMILES: Cc1cc(C2(c3cccc(-c4ccc(Cl)nc4)c3)COCC(N)=N2)ccc1OC(F)F] | 0.36 | — |
| 46 | 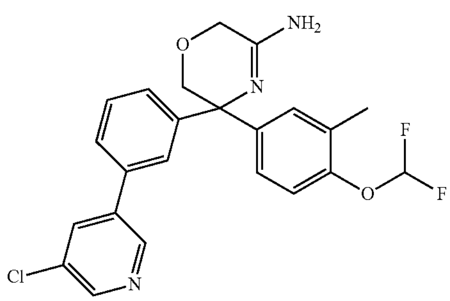 [SMILES: Cc1cc(C2(c3cccc(-c4cncc(Cl)c4)c3)COCC(N)=N2)ccc1OC(F)F] | 0.04 | 0.03 |
| 47 | 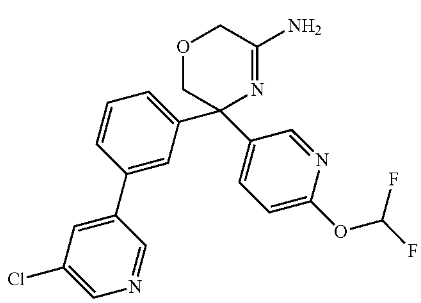 [SMILES: NC1=NC(c2ccc(OC(F)F)nc2)(c2cccc(-c3cncc(Cl)c3)c2)COC1] | 0.11 | — |
| 48 | 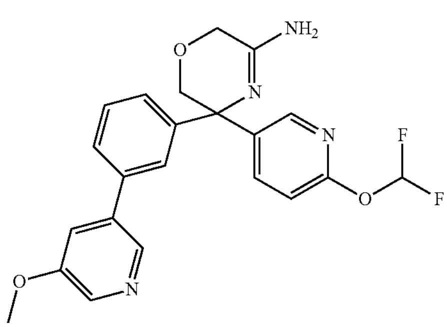 [SMILES: COc1cncc(-c2cccc(C3(c4ccc(OC(F)F)nc4)COCC(N)=N3)c2)c1] | 0.03 | — |

TABLE 1-continued

IC$_{50}$ values of selected examples

| Exam. | Structure | BACE1 IC$_{50}$ [μM] | BACE2 IC$_{50}$ [μM] |
|---|---|---|---|
| 49 | 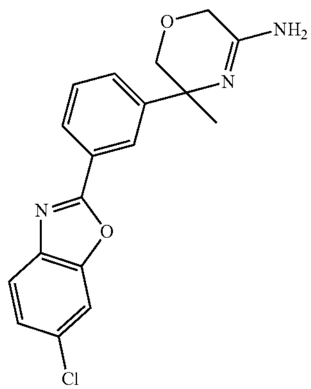 [SMILES: CC1(c2cccc(-c3nc4ccc(Cl)cc4o3)c2)COCC(N)=N1] | 0.20 | 0.20 |
| 50 | 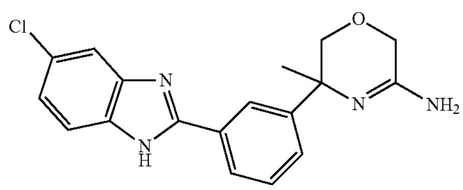 [SMILES: CC1(c2cccc(-c3nc4cc(Cl)ccc4[nH]3)c2)COCC(N)=N1] | 1.28 | — |
| 51 | 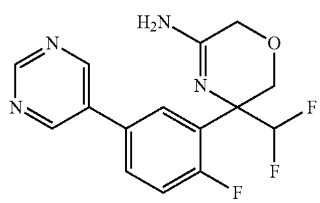 [SMILES: NC1=NC(c2cc(-c3cncnc3)ccc2F)(C(F)F)COC1] | 0.77 | — |
| 52 | 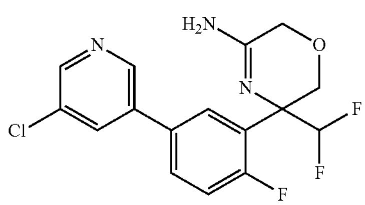 [SMILES: NC1=NC(c2cc(-c3cncc(Cl)c3)ccc2F)(C(F)F)COC1] | 0.28 | — |
| 53 | 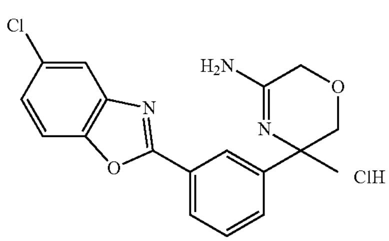 [SMILES: CC1(c2cccc(-c3nc4cc(Cl)ccc4o3)c2)COCC(N)=N1 ; Cl] | 1.49 | — |
| 54 | 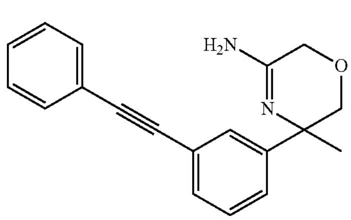 [SMILES: CC1(c2cccc(C#Cc3ccccc3)c2)COCC(N)=N1] | 1.47 | — |

TABLE 1-continued

IC$_{50}$ values of selected examples

| Exam. | Structure | BACE1 IC$_{50}$ [μM] | BACE2 IC$_{50}$ [μM] |
|---|---|---|---|
| 55 | (structure) | 2.78 | — |
| 56 | (structure) | 2.55 | — |
| 57 | (structure) | 6.72 | — |
| 58 | (structure) | 8.34 | — |
| 59 | (structure) | 4.39 | — |

CYP Inhibition Assay

Inhibition of cytochromes P450 (CYPs) 2C9, 2D6 and 3A4 was assessed using human liver microsomes and CYP-selective substrate metabolism reactions. 50 μl incubations were made up containing (finally) 0.2 mg/ml pooled human liver microsomes, 5 μM substrate (diclofenac for CYP2C9 [4'hydroxylase], dextromethorphan for CYP2D6 [O-demethylase] or midazolam for CYP3A4 [1'hydroxylase]), 0.25 μL DMSO containing test inhibitor and NADPH regenerating system. Test inhibitor concentrations of 50, 16.7, 5.6, 1.9, 0.6 and 0.2 μM were assessed in singlicate. Incubations were prewarmed to 37° C. for 10 minutes before initiation by addition of NADPH regenerating system. Incubations were quenched after 5 minutes (20 minutes for dextromethorphan) by addition of 50 μl cold acetonitrile containing 20 ng/ml 4-OH-diclofenac-13C6, 20 ng/mL dextrorphan-D3 and 20 ng/mL 1-OH-midazolam-D4. Quenched incubates were stored at −20° C. for at least 1 hour before centrifugation (20,000×g, 20 minutes). Supernatants were removed and diluted 1:1 with water prior to analysis using a RapidFire sample injector system and API4000 mass spectrometer. Peak areas for substrate, metabolite and stable-labelled metabolite standard were determined using MS/MS. The peak area ratios between the metabolite generated by the enzymatic reaction and the internal standard were used in subsequent calculations. The percentage of (DMSO) control activity was calculated for each incubate and IC$_{50}$ values estimated by non-linear regression. Sulfaphenazole, quinidine or ketoconazole were tested in each CYP2C9, CYP2D6 or CYP3A4 inhibition experiment, respectively, to ensure assay sensitivity and reproducibility. (Validated assays for human cytochrome P450 activities, R. L. Walsky and R. S. Obach, Drug Metabolism and Disposition 32: 647-660, 2004. and S. Fowler and H. Zhang, The AAPS Journal, Vol. 10, No. 2, 410-424, 2008.)

Cathepsin D and Cathepsin E Fluorescent Substrate Kinetic Assays

General Assay Principle

The MR121 fluorescence assays described below are based on the fact that MR121 forms a non-fluorescent ground state complex with tryptophan. In solution this formation occurs at millimolar concentrations of tryptophan. The mechanism can be used to design a generic biochemical assay for proteases. A substrate peptide is labeled at the N-terminus with tryptophan and at the C-terminus with the fluorophore MR121 (for cathepsin D the 10 amino acid peptide WTSVLMAAPC-MR121 was used; for cathepsin E, MR121-CKLVFFAEDW was used). In absence of protease activity, the substrates remain intact and the MR121 fluorescence is reduced by the high local Trp-concentration. If the substrates are cleaved by the enzymes the MR121 fluorescence is recovered.

Assay Procedure

The fluorescent substrate cathepsin D and cathepsin E kinetic assays were performed at room temperature in 384-well microtiter plates (black with clear flat bottom, non binding surface plates from Corning) in a final volume of 51 µl. The test compounds were serially diluted in DMSO (15 concentrations, 1/3 dilution steps) and 1 µl of diluted compounds were mixed for 10 min with 40 µl of cathepsin D (from human liver, Calbiochem) diluted in assay buffer (100 mM sodium acetate, 0.05% BSA, pH 5.5; final concentration: 200 nM) or with 40 µl of recombinant human cathepsin E (R&D Systems) diluted in assay buffer (100 mM sodium acetate, 0.05% BSA, pH 4.5; final concentration: 0.01 nM). After addition of 10 µl of the cathepsin D substrate WTSVLMAAPC-MR121 diluted in cathepsin D assay buffer (final concentration: 300 nM) or 10 µl of the cathepsin E substrate MR121-CKLVFFAEDW diluted in cathepsin E assay buffer (final concentration: 300 nM), the plates were strongly shaken for 2 minutes. The enzymatic reaction was followed in a plate: vision reader (Perkin Elmer) (excitation wavelength: 630 nm; emission: 695 nm) for at least 30 minutes in a kinetic measurement detecting an increase of MR121 fluorescence during the reaction time. The slope in the linear range of the kinetic was calculated and the $IC_{50}$ of the test compounds were determined using a four parameter equation for curve fitting.

p-gp (P-glycoprotein) Assay

Cell Lines and Vesicles Used for Transport Experiments

The LLC-PK1 cell line (ATCC #CL-101) is a porcine kidney epithelial cell line. The MDR1 (Human multidrug resistance protein 1) transfected cell lines were obtained from Dr. A. Schinkel, The Netherlands Cancer Institute (Amsterdam, The Netherlands). All cell lines were cultured on permeable inserts (Costar, 0.33 cm² area, pore size 3.0 µm, low density) at $4.5 \cdot 10^5$ cells/cm². Transport measurements were performed at day 4 after seeding. Tightness of the cell monolayer was controlled via the permeability of the extracellular marker lucifer yellow (10 µM). A detailed description of the method was reported by Schwab et al. (Schwab D, Schrag P, Portmann R, Rühmann S. *Operation procedure: LLC-PK1 cell lines, parental and transfected with human (MDR1) or mouse (mdr1a) Pglycoprotein to study transcellular transport by P-glycoprotein*. Report No. 1008708. Jul. 1, 2002. and Schwab D, Schrag P, Portmann R. Validation report on in vitro P-glycoprotein transport of 16 reference compounds in LLC-PK1 cells (parental) and MDR1 or mdr1a (Mouse multidrug resistance protein 1a) transfected LLC-PK1 cells and correlation to in vivo brain penetration in mice. Report No. 1008771. Aug. 21, 2002.). Experiments showing lucifer yellow permeation superior to 1%/h were rejected.

In Vitro Transport Experiments

Bidirectional transcellular transport using LLC-PK1 and L-MDR1 LLC-PK1 cells exogenously expressing the human MDR1)

The method used for transport experiments was reported Schwab et al. (see above.). The experiments were performed on a TECAN automated liquid handling system. Briefly, medium was removed from all compartments and the medium of receiver side was replaced with culture medium. The trans-cellular transport measurements were initiated by adding the substrate together with extracellular marker lucifer yellow to the donor side Inhibitors were added to both sides (1 µM elacridar). Transport experiments were performed both in the basolateral-to-apical and apical-to-basolateral directions with 3 wells each. The plates were incubated at 37° C. and 5% $CO_2$ in a Liconic incubator. Samples were taken from the donor and the opposite (acceptor) side after 2 hours incubation. Concentrations of substrate in both compartments were determined by scintillation counting (digoxin) or by LC-MS/MS. The extracellular marker (lucifer yellow) was quantified using a spectrafluor plus reader at 430/535 nm (Ex/Em). In each experiment 3 different inserts were used for each condition and a mean was calculated.

Data Analysis

Bidirectional transcellular transport using LLC-PK1 and L-MDR1 cells

For the transcellular transport, the following equation was used for data evaluation:

$$P_{app} = \frac{1}{A * C_0} * \frac{dQ}{dt}$$

where $P_{app}$, A, $C_0$, and dQ/dt represent the apparent permeability, the filter surface area, the initial concentration, and the amount transported per time period, respectively. $P_{app}$ values were calculated on the basis of a single time point (2 h).

Transport efflux ratios (ER) were calculated as follows:

$$ER = \frac{P_{app}BA}{P_{app}AB}$$

where $P_{app}BA$ is the permeability value in the basolateral-to-apical direction, and $P_{app}AB$ the permeability value in the apical-to-basolateral direction. $P_{app}$ were not corrected for flux of the extracellular marker lucifer yellow, which was used to assess the quality of the cell monolayers.

Results

TABLE 2 biological data of selected examples

| Ex. | P-gp human | Cathepsin E $IC_{50}$ [µM] | Cathepsin D $IC_{50}$ [µM] | CYP $IC_{50}$ [µM] [5] | | |
|---|---|---|---|---|---|---|
| | | | | 3A4 | 2D6 | 2C9 |
| 32 | 1.1 | 3.8 | 2.8 | >50 | >50 | 3.7 |
| 35 | 21 | — | — | >50 | 18 | >50 |
| 36 | 11 | 13 | 34 | >50 | 41 | >50 |

Pharmaceutical Compositions

The compounds of formula I and the pharmaceutically acceptable salts can be used as therapeutically active substances, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical compositions. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

The following examples illustrate the present invention without limiting it, but serve merely as representative thereof. The pharmaceutical compositions conveniently contain about 1-500 mg, preferably 1-100 mg, of a compound of formula I. Examples of compositions according to the invention are:

Example A

Tablets of the following composition are manufactured in the usual manner:

TABLE 3 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Micro crystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 4 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 5 possible soft gelatin capsule ingredient composition

| ingredient | mg/capsule |
|---|---|
| Compound of formula I | 5 |
| Yellow wax | 8 |

TABLE 5-continued possible soft gelatin capsule ingredient composition

| ingredient | mg/capsule |
|---|---|
| Hydrogenated Soya bean oil | 8 |
| Partially hydrogenated plant oils | 34 |
| Soya bean oil | 110 |
| Total | 165 |

TABLE 6 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 7 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 8 possible injection solution composition

| ingredient | mg/injection solution. |
|---|---|
| Compound of formula I | 3 |
| Polyethylene Glycol 400 | 150 |

TABLE 8-continued possible injection solution composition

| ingredient | mg/injection solution. |
|---|---|
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 9 possible sachet composition

| ingredient | mg/sachet |
|---|---|
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

Preparation of the intermediate iminoether (RS)-3-(3-bromo-phenyl)-5-methoxy-3-methyl-3,6-dihydro-2H[1,4]oxazine (intermediate XI-1)

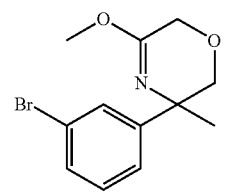 [SMILES: COC1=NC(C)(c2cccc(Br)c2)COC1]

a) (RS)-5-(3-Bromo-phenyl)-5-methyl-imidazolidine-2,4-dione (intermediate V-1)

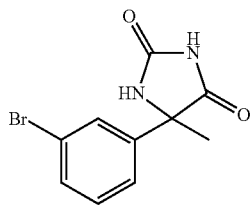

A mixture of 3-bromo-acetophenone (10.0 g, 50 mmol), potassium cyanide (4.96 g, 75 mmol), and ammonium carbonate (33.45 g, 348 mmol) in ethanol (65 ml) was heated in an autoclave at 120° C. for 16 h. For the workup, the reaction mixture was cooled to room temperature, then treated with water (250 ml) and ethyl acetate (500 ml). The aqueous layer was separated and re-extracted with ethyl acetate (250 ml). The combined organic layers were washed twice with saturated sodium chloride solution (2×250 ml), thereafter dried over sodium sulfate, and evaporated at reduced pressure. There were obtained 13.2 g (98.6% of theory) of (RS)-5-(3-bromo-phenyl)-5-methyl-imidazolidine-2,4-dione as a white solid. The purity of the product allowed using it in the next step without further purification. MS (ISP): m/z=267.2 [M+H]$^+$, 269.2 [M+2+H]$^+$.

b) (RS)-2-Amino-2-(3-bromo-phenyl)-propionic acid methyl ester (intermediate VII-1)

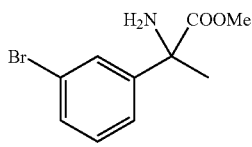

A dispersion of (RS)-2-amino-2-(3-bromo-phenyl)-propionic acid methyl ester (12.81 g, 48 mmol) in 6 N sodium hydroxide solution (95.23 ml) was heated to reflux for 48 h. For the workup, the reaction mixture was cooled with ice and treated with hydrochloric acid (36.5%) until pH 1 was reached. The mixture was evaporated to dryness at reduced pressure. The crude (RS)-2-amino-2-(3-bromo-phenyl)-propionic acid hydrochloride was dispersed in methanol (500 ml) and cooled to 0° C. Within 12 minutes and under ice cooling, thionylchloride (18.02 ml, 246 mmol) was added dropwise. After complete addition, the reaction mixture was heated to reflux for 60 h. For the workup, the reaction mixture was cooled to room temperature and evaporated at reduced pressure. The white residue was treated with a mixture of water and ice (200 ml), triethylamine (16.5 ml), and diethylether (500 ml). The resulting suspension was filtrated over Dicalite®; thereafter the aqueous layer was separated and re-extracted with diethylether (250 ml). The combined organic layers were washed with saturated sodium chloride solution (250 ml), dried over sodium sulfate, and evaporated at reduced pressure. There were obtained 9.39 g (76.7% of theory) of (RS)-2-amino-2-(3-bromo-phenyl)-propionic acid methyl ester as a light yellow oil. The purity of the product allowed using it in the next step without further purification. MS (ISP): m/z=258.1 [M+H]$^+$, 260.0 [M+2+H]$^+$.

c) (RS)-2-Amino-2-(3-bromo-phenyl)-propan-1-ol (intermediate VIII-1)

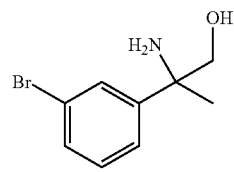

A solution of the (RS)-2-amino-2-(3-bromo-phenyl)-propionic acid methyl ester (9.39 g, mmol) in tetrahydrofuran (360 ml) was treated portionwise at −5° C. with lithiumaluminiumhydride (1.41 g, 36 mmol; 282 mg/2 min). After complete addition, stirring was continued at 0-5° C. for 30 minutes. For the workup, the reaction mixture was cooled to −7° C., and water (9 ml) was added dropwise. Thereafter, 2 N sodium hydroxide solution (9 ml) was added and stirring continued for 15 minutes at room temperature. They grey suspension was filtrated through Dicalite which was washed with tetrahydrofuran (200 ml). The filtrate was evaporated at reduced pressure. There were obtained 8.67 g of crude (RS)-2-amino-2-(3-bromo-phenyl)-propan-1-ol as colorless oil. The purity of the product allowed using it in the next step without further purification. MS (ISP): m/z=230.1 [M+H]$^+$, 232.0 [M+2+H]$^+$.

d) (RS)—N-[1-(3-Bromo-phenyl)-2-hydroxy-1-methyl-ethyl]-2-chloro-acetamide (intermediate IX-1)

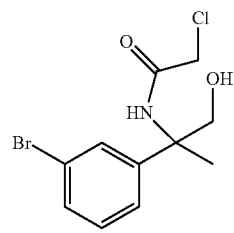 [SMILES: CC(CO)(NC(=O)CCl)c1cccc(Br)c1]

A solution of crude (RS)-2-amino-2-(3-bromo-phenyl)-propan-1-ol (8.38 g, 36 mmol) and triethylamine (6.08 ml, 44 mmol) in acetonitrile (140 ml) was treated dropwise at −2° C. with chloro-acetyl chloride (3.25 ml, 40 mmol). After complete addition, the orange colored solution was left to warm to room temperature and stirring was continued for 2 h. For the workup, to the reaction was added silica gel (10 g) and it was evaporated at reduced pressure, thereafter, it was purified by chromatography on silica gel using a gradient of dichloromethane/methanol=100/0 to 90/10 as the eluent. There were obtained 9.62 g (86% of theory) of (RS)—N-[1-(3-bromo-phenyl)-2-hydroxy-1-methyl-ethyl]-2-chloro-acetamide as a light brown oil. MS (ISP): m/z=304.1 [M+H]$^+$, 306.1 [M+2+H]$^+$, 308.2 [M+4+H]$^+$.

e) (RS)-5-(3-Bromo-phenyl)-5-methyl-morpholin-3-one (intermediate X-1)

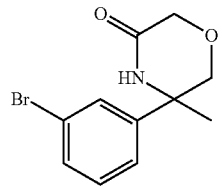

A solution of (RS)—N-[1-(3-bromo-phenyl)-2-hydroxy-1-methyl-ethyl]-2-chloro-acetamide (5.36 g, 17 mmol) in 2-methyl-2-butanol (100 ml) was treated in one portion with potassium tert-butylate (6.66 g, 58 mmol). Initially, the temperature rose to 30° C.; the reaction mixture was left to cool to room temperature and stirring was continued for one hour. For the workup, the reaction mixture was treated with methanol (50 ml), then evaporated at reduced pressure. The residue was purified by chromatography on silica gel using a gradient of dichloromethane/methanol=100/0 to 75/25 as the eluent. There were obtained 4.18 g (88% of theory) of (RS)-5-(3-bromo-phenyl)-5-methyl-morpholin-3-one as a white solid. MS (ISP): m/z=270.1 [M+H]$^+$, 272.2 [M+2+H]$^+$.

f) (RS)-3-(3-Bromo-phenyl)-5-methoxy-3-methyl-3,6-dihydro-2H[1,4]oxazine (intermediate XI-1)

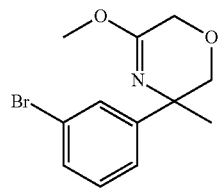

In a vacuum dried flask under an argon atmosphere, a solution of (RS)-5-(3-bromo-phenyl)-5-methyl-morpholin-3-one (3.0 g, 11.1 mmol) in dichloromethane (145 ml) was treated with trimethyloxonium tetrafluoroborate (2.594 g, 17 mmol). The reaction mixture was stirred at room temperature for 17 hours. For the workup, the incomplete reaction was extracted with a saturated solution of sodium hydrogen-carbonate (70 ml). The organic layer was dried over sodium sulfate and evaporated. There were obtained 3.12 g of the title compound as light yellow oil containing about 17% of the starting lactam. MS (ISP): m/z=284.2 [M+H]$^+$, 286.1 [M+2+H]$^+$.

Preparation of the intermediate iminoether (RS)-3-(5-bromo-2-fluoro-phenyl)-5-methoxy-3-methyl-3,6-dihydro-2H[1,4]oxazine (intermediate XI-2)

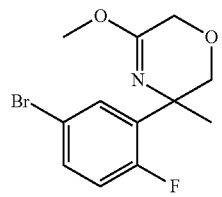

In close analogy to the reaction sequence for the preparation of (RS)-3-(3-bromo-phenyl)-5-methoxy-3-methyl-3,6-dihydro-2H[1,4]oxazine (intermediate XI-1) the (RS)-3-(5-bromo-2-fluoro-phenyl)-5-methoxy-3-methyl-3,6-dihydro-2H-[1,4]oxazine (intermediate XI-2) was obtained as follows:

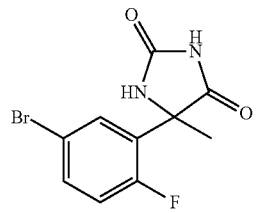

a) Intermediate V-2 (R$^1$=Me, R$^2$=F, Y=Br): Starting from 1-(5-bromo-2-fluoro-phenyl)-ethanone (CAS 198477-89-3) (49 mmol) the (RS)-5-(5-bromo-2-fluoro-phenyl)-5-methyl-imidazolidine-2,4-dione was obtained as a light yellow solid (12.41 g, 89% of theory). MS (ISP): m/z=285.0 [M+H]$^+$, 287.0 [M+2+H]$^+$.

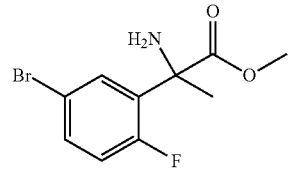

b) Intermediate VII-2 (R$^1$=Me, R$^2$=F, Y=Br): Starting from (RS)-5-(5-bromo-2-fluoro-phenyl)-5-methyl-imidazolidine-2,4-dione (intermediate V-2) (43 mmol) via the (RS)-2-amino-2-(5-bromo-2-fluoro-phenyl)-propionic acid the (RS)-2-amino-2-(5-bromo-2-fluoro-phenyl)-propionic acid methyl ester was obtained as a light yellow solid (3.82 g, 32% of theory). MS (ISP): m/z=275.9 [M+H]$^+$, 278.0 [M+2+H]$^+$.

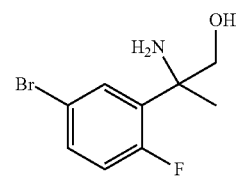

c) Intermediate VIII-2 (R$^1$=Me, R$^2$=F, Y=Br): Starting from (RS)-2-amino-2-(5-bromo-2-fluoro-phenyl)-propionic acid methyl ester (intermediate VII-2) (14 s mmol) the (RS)-2-amino-2-(5-bromo-2-fluoro-phenyl)-propan-1-ol was obtained as a light yellow solid in quantitative yield (3.43 g). MS (ISP): m/z=248.1 [M+H]$^+$, 250.1 [M+2+H]$^+$.

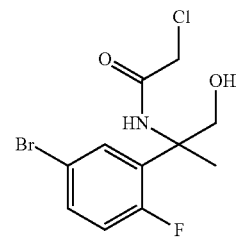 [SMILES: CC(CO)(NC(=O)CCl)c1cc(Br)ccc1F]

d) Intermediate IX-2 (R¹=Me, R²=F, Y=Br): Starting from (RS)-2-amino-2-(5-bromo-2-fluoro-phenyl)-propan-1-ol (intermediate VIII-2) (14 mmol) the N—[(RS)-1-(5-bromo-2-fluoro-phenyl)-2-hydroxy-1-methyl-ethyl]-2-chloro-acetamide was obtained as a yellow oil (2.71 g, 60% of theory). MS (ISP): m/z=324.2 [M+H]⁺, 326.3 [M+2+H]⁺.

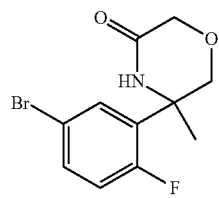 [SMILES: CC1(c2cc(Br)ccc2F)COCC(=O)N1]

e) Intermediate X-2 (R¹=Me, R²=F, Y=Br): Starting from N—[(RS)-1-(5-bromo-2-fluoro-phenyl)-2-hydroxy-1-methyl-ethyl]-2-chloro-acetamide (intermediate IX-2) (8 mmol) the (RS)-5-(5-bromo-2-fluoro-phenyl)-5-methyl-morpholin-3-one was obtained as a light yellow solid (2.02 g, 88% of theory). MS (ISP): m/z=286.0 [M+H]⁺, 288.1 [M+2+H]⁺.

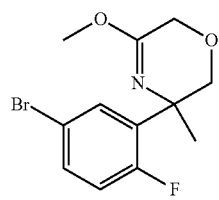

f) Intermediate XI-2 (R¹=Me, R²=F, R″=Me, Y=Br): Starting from (RS)-5-(5-bromo-2-fluoro-phenyl)-5-methyl-morpholin-3-one (intermediate X-2) (0.6 mmol) the (RS)-3-(5-bromo-2-fluoro-phenyl)-5-methoxy-3-methyl-3,6-dihydro-2H-[1,4]oxazine was obtained as a light yellow oil (0.17 g, 95% of theory). MS (ISP): m/z=302.1 [M+H]⁺, 304.1 [M+2+H]⁺.

Preparation of the intermediate iminoether (RS)-5-ethoxy-3-(3-iodo-phenyl)-3-methyl-3,6-dihydro-2H-[1,4]oxazine (intermediate XI-3)

a) (RS)-5-(3-Iodo-phenyl)-5-methyl-morpholin-3-one (intermediate X-3)

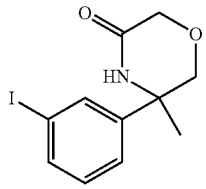

A mixture of (RS)-5-(3-bromo-phenyl)-5-methyl-morpholin-3-one (X-1) (2.0 g), cupper(I) iodide (72 mg), trans-N,N'-dimethyl-1,2-cyclohexandiamine (105 mg), and sodium iodide (2.22 g) in dioxane (20 ml) was heated at 110° C. over the weekend. The reaction mixture was evaporated at reduced pressure and the residue directly transferred to column chromatography on silica using a gradient of dichloromethane/methanol=100/0 to 75/25 as the eluent. The (RS)-5-(3-iodo-phenyl)-5-methyl-morpholin-3-one was obtained as a light green solid (2.26 g, 96% of theory). MS (ISP): m/z=318.2 [M+H]⁺.

b) Starting from (RS)-5-(3-iodo-phenyl)-5-methyl-morpholin-3-one (intermediate X-3) (2.25 g) the alkylation with triethyloxonium tetrafluoroborate yielded the (RS)-5-ethoxy-3-(3-iodo-phenyl)-3-methyl-3,6-dihydro-2H-[1,4]oxazine (intermediate XI-3) as a light brown oil (2.34 g, 67% of theory). MS (ISP): m/z=346.1 [M+H]⁺.

Preparation of the intermediate amino oxazine (RS)-5-(3-bromo-phenyl)-5-methyl-5,6-dihydro-2H-[1,4]oxazin-3-ylamine (intermediae XII-1)

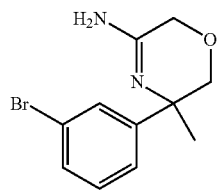

A dried pressure tube was charged with a dispersion of (RS)-3-(3-bromo-phenyl)-5-methoxy-3-methyl-3,6-dihydro-2H[1,4]oxazine (3.91 g, 14 mmol) and ammonium chloride (4.42 g, 83 mmol) in methanol (140 ml). The tube was sealed and heated at 100° C. overnight. After cooling, the reaction mixture was evaporated to dryness. The crude product was purified on an Isolute flash NH₂ column using a gradient of dichloromethane/methanol=100/0 to 75/25 as the eluent. The (RS)-5-(3-bromo-phenyl)-5-methyl-5,6-dihydro-2H-[1,4]oxazin-3-ylamine was obtained as a light yellow foam (2.71 g, 73% of theory). MS (ISP): m/z=269.2 [M+H]⁺, 271.1 [M+2+H]⁺.

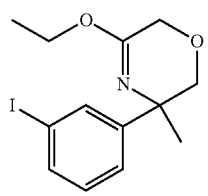

Intermediate XII-2 ($R^1$=Me, Y=I, n=0)

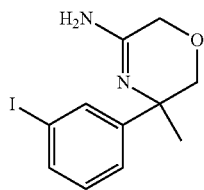

Starting from (RS)-5-ethoxy-3-(3-iodo-phenyl)-3-methyl-3,6-dihydro-2H-[1,4]oxazine (intermediate XI-3) (2.32 g) the (RS)-5-(3-iodo-phenyl)-5-methyl-5,6-dihydro-2H-[1,4]oxazin-3-ylamine was obtained as a white solid (0.93 g, 63% of theory). MS (ISP): m/z=317.1 $[M+H]^+$.

Preparation of the intermediate amino oxazine (RS)-5-(3-Bromo-4-fluoro-phenyl)-5-methyl-5,6-dihydro-2H-[1,4]oxazin-3-ylamine (intermediate XII-3)

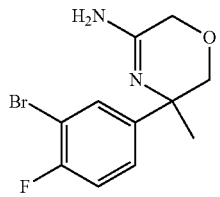

a) (RS)-5-(3-Bromo-4-fluoro-phenyl)-5-methyl-morpholin-3-one (intermediate X-4)

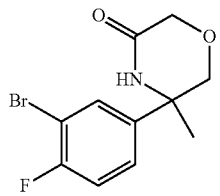

In close analogy to the reaction sequence described for the preparation of intermediate X-2 and starting from 1-(3-bromo-4-fluoro-phenyl)-ethanone (CAS 1007-15-4) the (RS)-5-(3-bromo-4-fluoro-phenyl)-5-methyl-morpholin-3-one (intermediate X-4) was obtained as a white solid. MS (ISP): m/z=288.0 $[M+H]^+$.

b) (RS)-5-(3-Bromo-4-fluoro-phenyl)-5-methyl-morpholin-3-thione (intermediate XVIII-1)

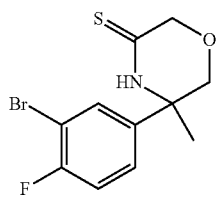 [SMILES: CC1(c2ccc(F)c(Br)c2)COCC(=S)N1]

A solution of the (RS)-5-(3-bromo-4-fluoro-phenyl)-5-methyl-morpholin-3-one (intermediate X-4) (265 mg, 0.9 mmol) in tetrahydrofuran (5.3 ml) was treated with 2,4-bis(4-methoxyphenyl)-1,3,2,4-dithiadiphosphetane-2,4-disulfide (Lawesson's reagent) (380 mg, 0.9 mmol). After 2.5 hours stirring at 70° C. the reaction mixture was evaporated at reduced pressure. The crude product was purified by chromatography on silica gel using a gradient of heptane/ethyl acetate=100/0 to 0/100 as the eluent. The (RS)-5-(3-bromo-4-fluoro-phenyl)-5-methyl-morpholin-3-thione was obtained as a light yellow gum (262 mg, 94% of theory). MS (ISP): m/z=302.2 $[M-H]^-$, 304.1 $[M+2-H]^-$.

c) (RS)-5-(3-Bromo-4-fluoro-phenyl)-5-methyl-5,6-dihydro-2H-[1,4]oxazin-3-ylamine (intermediate XII-3)

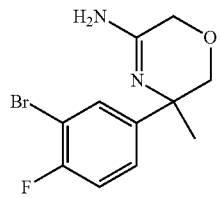 [SMILES: CC1(c2ccc(F)c(Br)c2)COCC(N)=N1]

A solution of (RS)-5-(3-bromo-4-fluoro-phenyl)-5-methyl-morpholin-3-thione (intermediate XVIII-1) (202 mg, 0.7 mmol) in methanol (15 ml) was treated with a solution of ammonia in methanol (7M, 5.7 ml, 39.8 mmol) and an aqueous solution of tert-butyl hydroperoxide (70% in water, 0.91 ml, 6.6 mmol). After stirring at room temperature overnight, the reaction mixture was diluted with water and extracted three times with dichloromethane. The combined organic layers were washed with water, then dried over sodium sulphate and evaporated. The crude product was purified by chromatography on silica gel using a gradient of heptane/ethyl acetate=100/0 to 0/100 as the eluent. The (RS)-5-(3-bromo-4-fluoro-phenyl)-5-methyl-5,6-dihydro-2H-[1,4]oxazin-3-ylamine was obtained as a colorless gum (109 mg, 57% of theory). MS (ISP): m/z=287.2 $[M+H]^+$, 289.1 $[M+2+H]^+$.

Preparation of the intermediate amino oxazine (R)-5-(5-Bromo-2-fluoro-phenyl)-5-methyl-5,6-dihydro-2H-[1,4]oxazin-3-ylamine (intermediate XII-4)

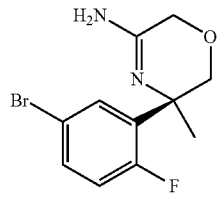 [SMILES: C[C@@]1(c2cc(Br)ccc2F)COCC(N)=N1]

a) 4-Bromo-1-fluoro-2-isopropenyl-benzene (intermediate XV-1)

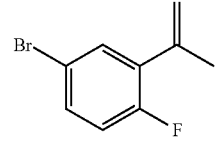

A suspension of methyltriphenylphosphonium bromide (58.92 g, 162 mmol) in tetrahydrofuran (400 ml) was treated with potassium tert-butylate (18.51 g, 162 mmol), and the yellow mixture was stirred at room temperature for 20 minutes. The orange reaction mixture was cooled to 0° C., and a solution of 1-(5-bromo-2-fluoro-phenyl)-ethanone (29.33 g, 135 mmol) in tetrahydrofuran (50 ml) was added within 16 minutes. The mixture was left to warm to room temperature and stirred for 1.5 hours. For the workup, the mixture was diluted with ethyl acetate (650 ml) and extracted with water (450 ml). The organic layer separated, washed with brine (220 ml), dried and evaporated at reduced pressure. After chromatography on silica gel using a gradient of hexane/ethyl acetate=100/0 to 80/20 as the eluent, the 4-bromo-1-fluoro-2-isopropenyl-benzene was obtained as a yellow oil (28.49 g, 98% of theory).

b) (RS)-4-Bromo-1-fluoro-2-(2-iodo-1-isocyanato-1-methyl-ethyl)-benzene (intermediate XVI-1)

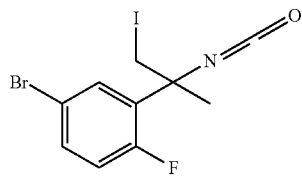 [SMILES: CC(CI)(N=CC=O)c1cc(Br)ccc1F]

Under a nitrogen atmosphere to a suspension of 4-bromo-1-fluoro-2-isopropenyl-benzene (9.40 g, 44 mmol) and freshly prepared silver cyanate (7.97 g, 52 mmol) in acetonitrile (50 ml) was added dropwise within 40 minutes at 0-7° C. in the dark a solution of iodine (12.21 g, 48 mmol) in ethyl acetate (100 ml). After complete addition the reaction mixture was left to warm to room temperature and stirring was continued for 16 hours. The precipitate was filtered off and washed with ethyl acetate (300 ml). The filtrates were washed with an aqueous solution of sodium sulphite (1%, 100 ml) and brine (50 ml). The organic layer was dried over sodium sulphate, then evaporated at reduced pressure. The (RS)-4-bromo-1-fluoro-2-(2-iodo-1-isocyanato-1-methyl-ethyl)-benzene was obtained as a brown oil (16.60 g, 98% of theory) which was used in the next step without further purification.

c) (RS)-4-(5-Bromo-2-fluoro-phenyl)-4-methyl-oxazolidin-2-one (intermediate XVII-1)

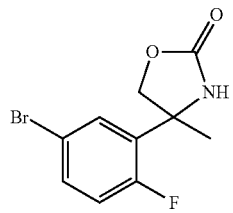

A solution of the crude (RS)-4-bromo-1-fluoro-2-(2-iodo-1-isocyanato-1-methyl-ethyl)-benzene (10.01 g, 26 mmol) in N,N-dimethyl-formamide (90 ml) was treated at room temperature with silver tetrafluoroborate (5.58 g, 29 mmol) and tert-butanol (3.86 g, 52 mmol). The yellow suspension was stirred at 80° C. overnight. For the workup, the reaction mixture was evaporated at reduced pressure, the residue triturated in ethyl acetate then filtered. The solution was concentrated at reduced pressure and the crude product purified by chromatography on silica gel using a gradient of dichloromethane/methanol=100/0 to 40/60 as the eluent. The (RS)-4-(5-bromo-2-fluoro-phenyl)-4-methyl-oxazolidin-2-one was obtained as a white solid (4.33 g, 61% of theory). MS (ISP): m/z=274.2 [M+H]$^+$, 276.2 [M+2+H]$^+$.

d) (R)-4-(5-Bromo-2-fluoro-phenyl)-4-methyl-oxazolidin-2-one (intermediate XVII-1a) and (S)-4-(5-Bromo-2-fluoro-phenyl)-4-methyl-oxazolidin-2-one (intermediate XVII-1b)

The (RS)-4-(5-bromo-2-fluoro-phenyl)-4-methyl-oxazolidin-2-one (intermediate XVII) (20.2 g) was divided in 1.0 g aliquots which were separated on chiral HPLC (Chiralpak AD) using a 90:10-mixture of heptane and ethanol as the eluent. The first eluting (R)-(−)-4-(5-bromo-2-fluoro-phenyl)-4-methyl-oxazolidin-2-one was obtained as a brown crystalline solid (9.15 g, e.e. >95%), the second eluting (S)-(+)-4-(5-bromo-2-fluoro-phenyl)-4-methyl-oxazolidin-2-one as a light brown solid (9.25 g, e.e. >95%).

e) (R)-2-Amino-2-(5-bromo-2-fluoro-phenyl)-propan-1-ol (intermediate VIII-3)

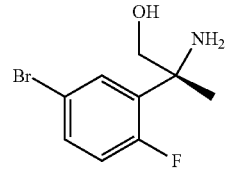

A solution of the (R)-4-(5-bromo-2-fluoro-phenyl)-4-methyl-oxazolidin-2-one (8.94 g, 33 mmol) in a 1:1-mixture of ethanol and water (120 ml) was treated with lithium hydroxide monohydrate (6.85 g, 163 mmol) and the reaction mixture was stirred at 100° C. overnight. For the workup, the reaction mixture was evaporated at reduced pressure and the residue dissolved in ethyl acetate (90 ml), then extracted with hydrochloric acid (2N, 90 ml). The aqueous layer was treated with a solution of sodium hydroxide (2N, 100 ml) and solid sodium chloride was added until saturation. The following extraction with ethyl acetate (3×200 ml) and the evaporation of the combined organic layers after drying over sodium sulphate yielded the (R)-2-amino-2-(5-bromo-2-fluoro-phenyl)-propan-1-ol as a white crystalline solid (7.90 g, 98% of theory, e.e.>98%).

f) N—[(R)-1-(5-Bromo-2-fluoro-phenyl)-2-hydroxy-1-methyl-ethyl]-2-chloro-acetamide (intermediate IX-3)

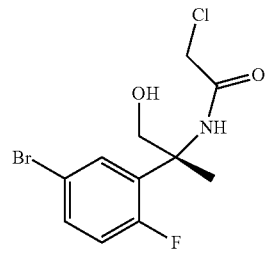 [SMILES: C[C@@](CO)(NC(=O)CCl)c1cc(Br)ccc1F]

In a manner analogous to that described for intermediate IX-1 the acylation of (R)-2-amino-2-(5-bromo-2-fluoro-phenyl)-propan-1-ol with chloro-acetyl chloride yielded the N—[(R)-1-(5-bromo-2-fluoro-phenyl)-2-hydroxy-1-methyl-ethyl]-2-chloro-acetamide as a light yellow oil (9.30 g, 90% of theory; e.e. >96%). MS (ISP): m/z=322.0 [M+H]⁺, 324.0 [M+2+H]⁺, 326.0 [M+4+H]⁺.

g) (R)-5-(5-Bromo-2-fluoro-phenyl)-5-methyl-morpholin-3-one (intermediate X-5)

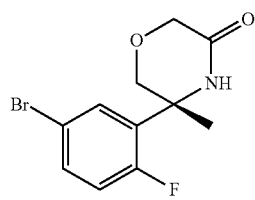

In a manner analogous to that described for intermediate X-1 the cyclization of N—[(R)-1-(5-bromo-2-fluoro-phenyl)-2-hydroxy-1-methyl-ethyl]-2-chloro-acetamide (9.30 g, 29 mmol) yielded the title compound as a white solid (6.49 g, 79% of theory).

h) (R)-5-(5-Bromo-2-fluoro-phenyl)-5-methyl-morpholine-3-thione (intermediate XVIII-2)

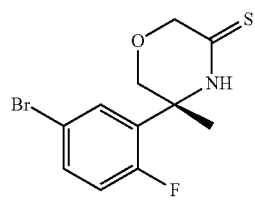 [SMILES: C[C@@]1(c2cc(Br)ccc2F)COCC(=S)N1]

A pressure tube was charged with a solution of N—[(R)-1-(5-bromo-2-fluoro-phenyl)-2-hydroxy-1-methyl-ethyl]-2-chloro-acetamide (2.00 g, 6.9 mmol) in tetrahydrofuran (50 ml). The colorless solution was treated with Lawesson's reagent (2.81 g, 6.9 mmol) to give a yellow suspension. The tube was sealed and the mixture stirred at 70° C. overnight. For the workup, the reaction mixture was diluted with ethyl acetate (300 ml) and extracted with a saturated solution of sodium hydrogen carbonate (75 ml). The organic layer was washed with brine (2×80 ml). The combined aqueous layers were extracted with ethyl acetate (300 ml). The combined organic layers were dried over sodium sulphate and concentrated at reduced pressure. The (R)-5-(5-bromo-2-fluoro-phenyl)-5-methyl-morpholine-3-thione was obtained as a light yellow gum (1.93 g, 92% of theory) sufficiently pure to be engaged in the next step without further purification. MS (ISP): m/z=302.0 [M+H]⁺, 304.0 [M+2+H]⁺.

i) (R)-5-(5-Bromo-2-fluoro-phenyl)-5-methyl-5,6-dihydro-2H-[1,4]oxazin-3-ylamine (Intermediate XII-4)

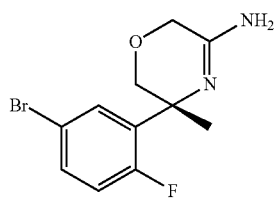

A pressure tube was charged with a solution of (R)-5-(5-bromo-2-fluoro-phenyl)-5-methyl-morpholine-3-thione (1.93 g, 6.3 mmol) in methanol (195 ml). A solution of ammonia in methanol (7M, 54 ml, 381 mmol) and an aqueous solution of tert-butyl hydroperoxide (70%, 8.17 g, 63.4 mmol) were added. The tube was sealed and the reaction mixture was stirred overnight at room temperature for 21 hours. For the workup, the reaction mixture was diluted with water and extracted three times with dichloromethane. The combined organic layers were washed with brine, dried over sodium sulphate and evaporated. The crude product was purified by chromatography on an Isolute flash NH₂ column using dichloromethane as the eluent. The (R)-5-(5-bromo-2-fluoro-phenyl)-5-methyl-5,6-dihydro-2H-[1,4]oxazin-3-ylamine was obtained as an off-white gum (1.42 g, 62% of theory). MS (ISP): m/z=287.1 [M+H]⁺, 289.0 [M+2+H]⁺.

Preparation of the intermediate amino oxazine (RS)-5-(3-bromo-phenyl)-5-(4-difluoromethoxy-3-methyl-phenyl)-5,6-dihydro-2H-[1,4]oxazin-3-ylamine (intermediate XII-5)

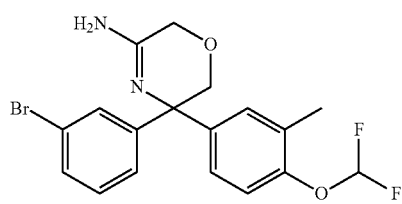 [SMILES: Cc1cc(C2(c3cccc(Br)c3)COCC(N)=N2)ccc1OC(F)F]

a) (RS)-4-(3-Bromo-phenyl)-4-(4-difluoromethoxy-3-methyl-phenyl)-oxazolidin-2-one (intermediate XVII-2)

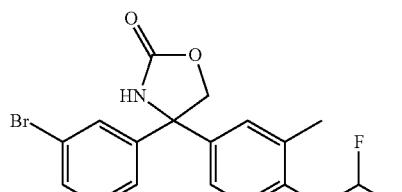

A solution of iodine (5.5 g, 1.1 eq.) in ethyl acetate (60 ml) was added dropwise to a suspension of silver isocyanate (3.3 g, 1.2 eq) and 4-[1-(3-bromo-phenyl)-vinyl]-1-difluoromethoxy-2-methyl-benzene (CAS 1180015-79-9) (6.7 g, 1 eq.) in acetonitrile (80 ml) and ethyl acetate (20 ml). During the addition the suspension was cooled in an ice-bath. The resulting brown suspension was stirred for 1 hour at room temperature. After an TLC sample indicated complete conversion of the starting material, the reaction mixture was filtrated and concentrated in vacuo. The crude was dissolved in tert-butanol (100 ml) and triethylamine (2.76 ml, 1 eq.) was added. The mixture was stirred at 100° C. overnight. For the workup the mixture was allowed to cool to room temperature, then the solvent was removed at reduced pressure and the residue taken up in ethyl acetate. The solution was washed with water (3×20 ml), dried over sodium sulphate and concentrated at reduced pressure. The residue was purified by chromatography on silica gel using a 9:1-mixture of cyclohexane and ethyl acetate as the eluent. There were obtained 5.1 g (67% of theory) of the (RS)-4-(3-bromo-phenyl)-4-(4-difluoromethoxy-3-methyl-phenyl)-oxazolidin-2-one as a white solid. MS (ISP): m/z=398 [M+H]$^+$.

b) (RS)-2-Amino-2-(3-bromo-phenyl)-2-(4-difluoromethoxy-3-methyl-phenyl)-ethanol (intermediate VIII-4)

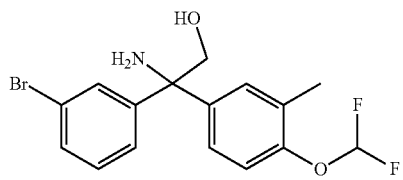 [SMILES: Cc1cc(C(N)(CO)c2cccc(Br)c2)ccc1OC(F)F]

A solution of 4-(3-bromo-phenyl)-4-(4-difluoromethoxy-3-methyl-phenyl)-oxazolidin-2-one (intermediate XVII-2) (5.1 g, 1 eq) in a 9:1-mixture of ethanol and water (50 ml) was added lithium hydroxide (9.2 g, 30 eq). The reaction was stirred at reflux for 3 hours. Then the mixture was allowed to cool to room temperature and concentrated at reduced pressure. The residue was extracted with ethyl acetate (3×20 ml), the combined organic layers were collected, dried over sodium sulphate and concentrated in vacuo. The residue was purified by chromatography on silica gel using a 5:1-mixture of cyclohexane and ethyl acetate as the eluent. There were obtained 4.8 g (93% of theory) of the (RS)-2-amino-2-(3-bromo-phenyl)-2-(4-difluoromethoxy-3-methyl-phenyl)-ethanol as a white solid.

c) (RS)-5-(3-Bromo-phenyl)-5-(4-difluoromethoxy-3-methyl-phenyl)-morpholin-3-one (intermediate X-5)

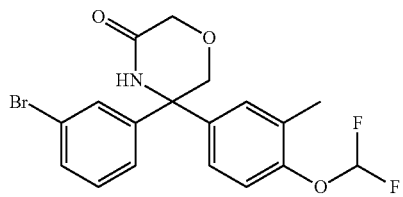 [SMILES: Cc1cc(C2(c3cccc(Br)c3)COCC(=O)N2)ccc1OC(F)F]

Chloroacetylchloride (1.81 ml, 1.2 eq) was added dropwise to a solution of (RS)-2-amino-2-(3-bromo-phenyl)-2-(4-difluoromethoxy-3-methyl-phenyl)-ethanol (intermediate VIII-4) (4.81 g, 1 eq) and triethylamine (2.78 ml, 1.5 eq) in acetonitrile (70 ml) at −2° C. After complete addition, the solution was left to warm to room temperature and stirring was continued for 5 hours. The reaction mixture was concentrated, washed with brine (3×20 ml), dried over sodium sulphate and concentrated in vacuo. The crude was dissolved in tert-butanol (50 ml), then treated in one portion with potassium tert-butanolate (4.9 g, 3.3 eq) and stirred at 35° C. overnight. The reaction mixture was then treated with water (50 ml) and extracted with ethyl acetate (3×20 ml). The combined organic layers were collected, dried over sodium sulphate and concentrated in vacuo. The residue was purified by chromatography on silica gel using a 9:1-mixture of cyclohexane and ethyl acetate as the eluent. The (RS)-5-(3-bromo-phenyl)-5-(4-difluoromethoxy-3-methyl-phenyl)-morpholin-3-one was obtained as a white solid (4.5 g, 81% of theory). MS (ISP): m/z=413.8 [M+H]$^+$.

d) (RS)-5-(3-Bromo-phenyl)-5-(4-difluoromethoxy-3-methyl-phenyl)-5,6-dihydro-2H-[1,4]oxazin-3-ylamine (intermediate XII-5)

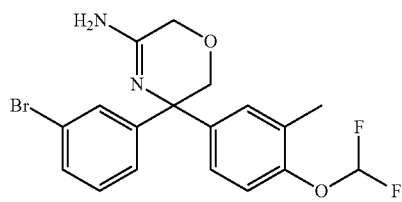 [SMILES: Cc1cc(C2(c3cccc(Br)c3)COCC(N)=N2)ccc1OC(F)F]

In a vacuum dried flask under an argon atmosphere, a solution of (RS)-5-(3-bromo-phenyl)-5-(4-difluoromethoxy-3-methyl-phenyl)-morpholin-3-one (2.5 g, 1 eq) in dichloromethane (80 ml) was treated with trimethyloxonium tetrafluoroborate (2.7 g, 3 eq). The reaction mixture was stirred at room temperature overnight. The incomplete reaction was then washed with a saturated solution of sodium hydrogen carbonate (50 ml). The organic layer was dried over sodium sulfate and evaporated. The crude was dissolved in methanol (15 ml) and the solution transferred under an nitrogen atmosphere into a dried pressure tube. After the addition of ammonium chloride (0.182 g, 3.4 mmol) the sealed pressure tube was heated at 100° C. for 16 hours. After cooling, the reaction mixture was filtered and evaporated to dryness, taken up with dichloromethane (30 ml) and filtered again. The solvent was removed and the residue was passed through a SCX (50 g) cartridge, washing with a mixture of dichloromethane and methanol. The product was recovered eluting with a solution of ammonia (2M) in methanol. 1.45 g of the (RS)-5-(3-bromo-phenyl)-5-(4-difluoromethoxy-3-methyl-phenyl)-5,6-dihydro-2H-[1,4]oxazin-3-ylamine were obtained as a white solid (58% of theory). MS (ISP): m/z=412.9 [M+H]$^+$.

Preparation of the intermediate amino oxazine (RS)-5-(3-bromo-phenyl)-5-(6-difluoromethoxy-pyridin-3-yl)-5,6-dihydro-2H-[1,4]oxazin-3-ylamine (intermediate XII-6)

a) 5-[1-(3-Bromo-phenyl)-vinyl]-2-methoxy-pyridine

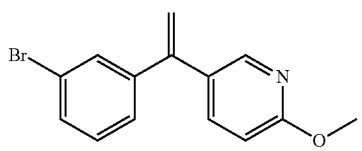 [SMILES: C=C(c1ccc(OC)nc1)c1cccc(Br)c1]

A solution of 5-bromo-2-methoxy-pyridine (10.0 g, 1 eq) in dry tetrahydrofuran (50 ml) was treated dropwise at −78° C. under a nitrogen atmosphere with n-butyllithium (1.6N in hexane, 30 ml, 0.9 eq). The mixture was stirred at −78° C. for 1 hour, then was added a solution of 3-bromo acetophenone (7.7 ml, 1.1 eq) in dry tetrahydrofuran (20 mL) at −78° C. The mixture was then allowed to warm to room temperature. The progress of the reaction was checked by TLC (cyclohexane/AcOEt 9:1). After 1 hour conversion to the desired product was complete. For the workup, saturated solution of ammonium chloride (30 ml) was added, the tetrahydrofuran layer was separated, and then the aqueous phase was extracted with dichloromethane (3×20 ml). The organic fractions were collected, dried over sodium sulphate and evaporated. The crude was dissolved in acetic acid (100 ml) and concentrated sulphuric acid (20 ml) was added, and mixture was stirred at room temperature for 2 hours. A solution of sodium hydroxide (15%) was added to the mixture until pH 6-5, then it was extracted with dichloromethane (3×25 ml). The organic phases were collected, dried and evaporated. The crude was purified by flash chromatography eluting with cyclohexane. 10.3 g of The 5-[1-(3-bromo-phenyl)-vinyl]-2-methoxy-pyridine was obtained as colorless oil (10.3 g, 71% of theory). MS (ISP): m/z=291.9 [M+H]$^+$.

b) 5-[1-(3-Bromo-phenyl)-vinyl]-1H-pyridin-2-one

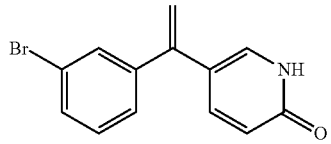 [SMILES: C=C(c1ccc(=O)[nH]c1)c1cccc(Br)c1]

A sealed tube was charged with 5-[1-(3-bromo-phenyl)-vinyl]-2-methoxy-pyridine (600 mg) and pyridinium hydrochloride (3 g) freshly prepared. The tube was heated at 125° C. for 10 minutes, then the mixture was allowed to cool to room temperature. The crude was dissolved in dichloromethane (15 ml), the solution washed with hydrochloric acid (1N) (2×15 ml), dried over sodium sulphate and evaporated. The crude product was purified by flash chromatography eluting with cyclohexane/ethyl acetate. The 5-[1-(3-bromo-phenyl)-vinyl]-1H-pyridin-2-one was obtained as a colorless oil (366 mg, 64% of theory). MS (ISP): m/z=278 [M+H]$^+$.

c) 5-[1-(3-Bromo-phenyl)-vinyl]-2-difluoromethoxy-pyridine (intermediate XV-2)

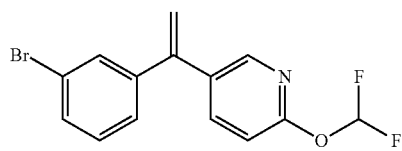 [SMILES: C=C(c1ccc(OC(F)F)nc1)c1cccc(Br)c1]

The 5-[1-(3-bromo-phenyl)-vinyl]-1H-pyridin-2-one (10 g, 1 eq) was dissolved in acetonitrile (180 ml) and degassed for 1 hour. Then sodium chlorodifluoroacetate (8.5 g, 1.2 eq) was added and the mixture heated to 100° C. overnight under a nitrogen atmosphere. The mixture was cooled to room temperature, the solvent was removed, and the crude was partitioned between water (100 ml) and ethyl acetate (100 ml). The organic layer was separated, dried over sodium sulphate, and concentrated in vacuo. The crude product was purified by flash chromatography eluting with ethyl acetate. The 5-[1-(3-bromo-phenyl)-vinyl]-2-difluoromethoxy-pyridine was obtained as colorless oil (2.6 g, 26% of theory). MS (ISP): m/z=328 [M+H]$^+$.

d) (RS)-2-Amino-2-(3-bromo-phenyl)-2-(6-difluoromethoxy-pyridin-3-yl)-ethanol (intermediate VIII-5)

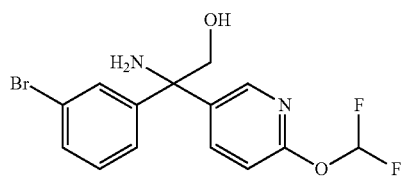 [SMILES: NC(CO)(c1ccc(OC(F)F)nc1)c1cccc(Br)c1]

In close analogy to the reaction sequence described for the preparation of intermediate VIII-3, the cyclisation of the 5-[1-(3-bromo-phenyl)-vinyl]-2-difluoromethoxy-pyridine with iodine and silver isocyanate followed by heating with tert-butanol and triethylamin, then by basic deprotection yielded the (RS)-2-amino-2-(3-bromo-phenyl)-2-(6-difluoromethoxy-pyridin-3-yl)-ethanol as a light yellow solid (1.6 g, 56% of theory). MS (ISP): m/z=361 [M+H]$^+$.

e) (RS)-5-(3-Bromo-phenyl)-5-(6-difluoromethoxy-pyridin-3-yl)-morpholin-3-one (intermediate X-6)

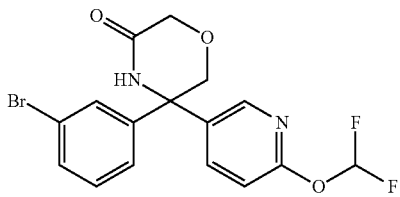 [SMILES: O=C1COCC(c2ccc(OC(F)F)nc2)(c2cccc(Br)c2)N1]

In close analogy to the reaction sequence described for the preparation of intermediate X-1, the acylation of the (RS)-2-amino-2-(3-bromo-phenyl)-2-(6-difluoromethoxy-pyridin-3-yl)-ethanol with chloroacetylchloride followed by cyclisation with tert-butanol and potassium tert-butanolate yielded the (RS)-5-(3-bromo-phenyl)-5-(6-difluoromethoxy-pyridin-3-yl)-morpholin-3-one as a light yellow solid (1.6 g, 91% of theory). MS (ISP): m/z=400.9 [M+H]$^+$.

f) (RS)-5-(3-Bromo-phenyl)-5-(6-difluoromethoxy-pyridin-3-yl)-morpholin-3-thione (intermediate XVIII-3)

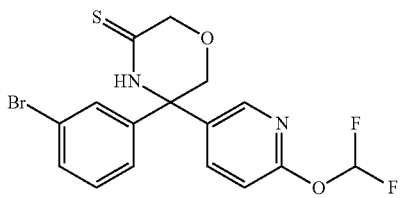

A mixture of (RS)-5-(3-bromo-phenyl)-5-(6-difluoromethoxy-pyridin-3-yl)-morpholin-3-one (1.6 g, 1.0 eq) and Lawesson's reagent (2.0 g, 1.2 eq) in tetrahydrofuran (60 ml) was stirred at room temperature overnight. For the workup, the solvent was removed at reduce pressure. The crude product was purified by chromatography on silica gel using a gradient of hexane/ethyl acetate as the eluent. The (RS)-5-(3-bromo-phenyl)-5-(6-difluoromethoxy-pyridin-3-yl)-morpholin-3-thione was obtained as a yellow foam (1.0 g, 83% of theory). MS (ISP): m/z=415 [M+H]$^+$.

g) (RS)-5-(3-Bromo-phenyl)-5-(6-difluoromethoxy-pyridin-3-yl)-5,6-dihydro-2H-[1,4]oxazin-3-ylamine (XII-6)

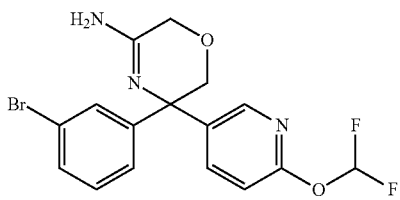 [SMILES: NC1=NC(c2ccc(OC(F)F)nc2)(c2cccc(Br)c2)COC1]

A dried pressure tube was charged under an argon atmosphere with a dispersion of 5-(3-bromo-phenyl)-5-(6-difluoromethoxy-pyridin-3-yl)-morpholine-3-thione (1.0 g) in a solution of ammonia (7M) in methanol (30 ml). The tube was sealed and heated at 100° C. for 3 hours. After cooling, the reaction mixture was evaporated to dryness and dissolved in dichloromethane, then loaded onto an SCX-cartridge. A 1:1-mixture of dichloromethane and methanol was passed through the column to remove impurities, and the aminoxazine was eluted with ammonia in methanol (2M solution). The (RS)-5-(3-bromo-phenyl)-5-(6-difluoromethoxy-pyridin-3-yl)-5,6-dihydro-2H-[1,4]oxazin-3-ylamine was obtained as a yellow foam (0.82 g, 83% of theory). MS (ISP): m/z=399 [M+H]$^+$.

Preparation of the intermediate protected amino oxazine (RS)-[5-(3-bromo-phenyl)-5-methyl-5,6-dihydro-2H-[1,4]oxazin-3-yl]-carbamic acid tert-butyl ester (intermediate XIII-1i

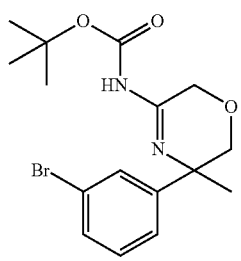 [SMILES: CC(C)(C)OC(=O)NC1=NC(C)(c2cccc(Br)c2)COC1]

A solution of (RS)-5-(3-bromo-phenyl)-5-methyl-5,6-dihydro-2H-[1,4]oxazin-3-ylamine (intermediate XII-1) (0.20 g) in dichloromethane (20 ml) was treated with N-ethyl-diisopropyl-amine (0.23 g), di-tert-butyl dicarbonate (0.364 g), and N,N-dimethyl-formamide (0.01 g) at room temperature overnight. The reaction mixture was evaporated and the residue was purified by column chromatography using a gradient of dichloromethane/methanol=100/0 to 80/20 as the eluent. The (RS)-[5-(3-bromo-phenyl)-5-methyl-5,6-dihydro-2H-[1,4]oxazin-3-yl]-carbamic acid tert-butyl ester (intermediate XIII-1) as the main component was obtained together with (RS)-[5-(3-bromo-phenyl)-5-methyl-5,6-dihydro-2H-[1,4]oxazin-3-yl]-dicarbamic acid di-tert-butyl ester as white solid (0.21 g, 78% of theory). MS (ISP): m/z=369.1 [M+H]$^+$, 371.0 [M+2+H]$^+$ and 469.3 [M+H]$^+$, 471.0 [M+2+H]$^+$.

Preparation of the intermediate lactam 3-((RS)-3-methyl-5-oxo-morpholin-3-yl)-benzoic acid (intermediate XXVI-1)

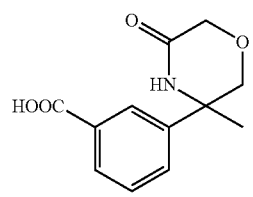 [SMILES: CC1(c2cccc(C(=O)O)c2)COCC(=O)N1]

a) 2-(3-Isopropenyl-phenyl)-[1,3]dioxolane (intermediate XX-1)

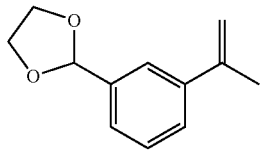

A degassed solution of 2-(3-bromo-phenyl)-[1,3]dioxolane (3.46 ml, 22.6 mmol) in dimethoxyethane (60 ml) was added into a tube which has been charged with a mixture of 2-isopropenyl-4,4,5,5-tetramethyl-[1,3,2]dioxaborolane (3.8 g, 22.6 mmol) and an aqueous solution of sodium carbonate (1M, 20 ml); tetrakis(triphenylphosphine)palladium(0) (0.266 g) is then added, the tube is sealed and heated to 90° C. overnight. After cooling of the reaction mixture, water (20 ml) was added, the aqueous layer separated and extracted with dichloromethane (3×20 ml). The combined organic layers were dried over sodium sulphate and evaporated. The crude product was purified by chromatography on silica gel using cyclohexane as the eluent. There were obtained 2.85 g (68% of theory) of the 2-(3-isopropenyl-phenyl)-[1,3]dioxolane.

b) (RS)-5-(3-[1,3]Dioxolan-2-yl-phenyl)-5-methyl-morpholin-3-one (intermediate XXV-1)

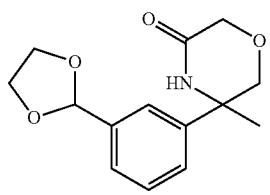 [SMILES: CC1(c2cccc(C3OCCO3)c2)COCC(=O)N1]

In a reaction sequence analogous to that described for the preparation of intermediate X-5, starting from the 2-(3-isopropenyl-phenyl)-[1,3]dioxolane (2.85 g), 1.49 g of the title compound were obtained.

c) 3-((RS)-3-Methyl-5-oxo-morpholin-3-yl)-benzoic acid (intermediate XXVI-1)

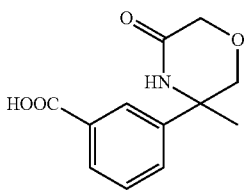 [SMILES: CC1(c2cccc(C(=O)O)c2)COCC(=O)N1]

A solution of (RS)-5-(3-[1,3]dioxolan-2-yl-phenyl)-5-methyl-morpholin-3-one (1.49 g, 5.7 mmol) in a mixture of tetrahydrofuran (65 ml) and water (13 ml) was treated with potassium monopersulphate (5.21 g, 8.5 mmol) under stirring at room temperature for 3 hours. For the workup, water (20 ml) and ethyl acetate were added. The organic layer was separated, washed with water (2×20 ml). The organic layer was dried over sodium sulphate and evaporated at reduced pressure. The 3-((RS)-3-methyl-5-oxo-morpholin-3-yl)-benzoic acid obtained (0.9 g, 67% of theory) was pure and could be used in the next step without further purification.

Example 1

Method A

5-[3-(5-Methoxy-pyridin-3-yl)-phenyl]-5-methyl-5,6-dihydro-2H-[1,4]oxazin-3-ylamine A degassed solution of (RS)-5-(3-bromo-phenyl)-5-methyl-5,6-dihydro-2H-[1,4]oxazin-3-ylamine (intermediate XII-1) (50 mg, 0.19 mmol), (5-methoxy-3-pyridinyl)-boronic acid (36 mg, 0.22 mmol), and cesium carbonate (244 mg, 0.75 mmol) in a mixture of tetrahydrofuran (3 ml) and water (1 ml) was treated in a tube under an argon atmosphere with [1,1'-bis(diphenylphosphino)ferrocene]dichloropalladium(II) (CAS 72287-26-4) (7 mg, 0.009 mmol). The tube was sealed and heated to 80° C. for 2 hours. For the workup, the reaction mixture was cooled, diluted with ethyl acetate and washed with water. The organic layer was separated, dried over sodium sulphate and evaporated. The crude product was purified by chromatography on an Isolute flash NH$_2$ column using a gradient of dichloromethane/methanol=100/0 to 95/5 as the eluent. The (RS)-5-[3-(5-methoxy-pyridin-3-yl)-phenyl]-5-methyl-5,6-dihydro-2H-[1,4]oxazinyl-amine was obtained as an off-white solid (31 mg, 56% of theory). MS (ISP): m/z=298.2 [M+H]$^+$.

Examples 2 and 3

In close analogy to the procedure described in Example 1 (method A), the following compounds were obtained by palladium-catalyzed coupling of (RS)-5-(3-bromo-phenyl)-5-methyl-5,6-dihydro-2H-[1,4]oxazin-3-ylamine (intermediate XII-1) with boronic acid derivatives using [1,1'-bis(diphenylphosphino)ferrocene]dichloropalladium(II) as the catalyst.

Example 2

5-(4'-Fluoro-biphenyl-3-yl)-5-methyl-5,6-dihydro-2H-[1,4]oxazin-3-ylamine or 5-(4'-Fluoro-biphenyl-3-yl)-5-methyl-5,6-dihydro-2H-[1,4]oxazin-3-ylamine formate With (4-fluorophenyl)-boronic acid the 5-(4'-fluoro-biphenyl-3-yl)-5-methyl-5,6-dihydro-2H-[1,4]oxazin-3-ylamine formate as an off-white solid after purification by preparative HPLC. MS (ISP): m/z=298.2 [M+H]$^+$.

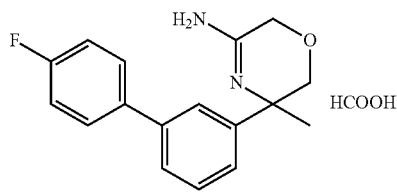 [SMILES: CC1(c2cccc(-c3ccc(F)cc3)c2)COCC(N)=N1 ; "HCOOH"]

Example 3

5-Methyl-5-(3-thiophen-3-yl-phenyl)-5,6-dihydro-2H-[1,4]oxazin-3-ylamine or 5-Methyl-5-(3-thiophen-3-yl-phenyl)-5,6-dihydro-2H-[1,4]oxazin-3-ylamine formate With β-thiophene)-boronic acid the 5-methyl-5-(3-thiophen-3-yl-phenyl)-5,6-dihydro-2H-[1,4]oxazin-3-ylamine formate as an off-white solid after purification by preparative HPLC. MS (ISP): m/z=273.3 [M+H]$^+$.

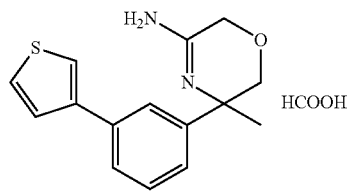 [SMILES: CC1(c2cccc(-c3ccsc3)c2)COCC(N)=N1 ; "HCOOH"]

Examples 4-26

In close analogy to the procedure described in Example 1 (method A), the following compounds were obtained by palladium-catalyzed coupling of (RS)-5-(3-bromo-phenyl)-5-methyl-5,6-dihydro-2H-[1,4]oxazin-3-ylamine (intermediate XII-1) with boronic acid derivatives using [1,1'-bis(diphenylphosphino)ferrocene]dichloropalladium(II) as the catalyst. In the following examples instead of a mixture of tetrahydrofuran and water a 2:1-mixture of N,N-dimethylacetamide and water was used as the solvent and with reaction times between 20 minutes and 5 hours.

Example 4

5-(3'-Chloro-biphenyl-3-yl)-5-methyl-5,6-dihydro-2H-[1,4]oxazin-3-ylamine or 5-(3'-Chloro-biphenyl-3-yl)-5-methyl-5,6-dihydro-2H-[1,4]oxazin-3-ylamine formate With (3-chlorophenyl)-boronic acid the 5-(3'-chloro-biphenyl-3-yl)-5-methyl-5,6-dihydro-2H-[1,4]oxazin-3-ylamine formate as a white solid after purification by preparative HPLC. MS (ISP): m/z=301.1 [M+H]$^+$.

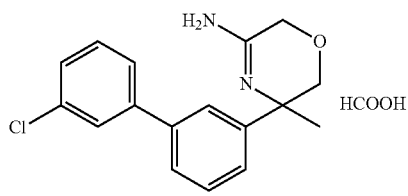 [SMILES: CC1(c2cccc(-c3cccc(Cl)c3)c2)COCC(N)=N1 ; "HCOOH"]

Example 5

5-(2',5'-Dichloro-biphenyl-3-yl)-5-methyl-5,6-dihydro-2H-[1,4]oxazin-3-ylamine or 5-(2',5'-Dichloro-biphenyl-3-yl)-5-methyl-5,6-dihydro-2H-[1,4]oxazin-3-ylamine formate With (2,5-dichlorophenyl)-boronic acid the 5-(2',5'-dichloro-biphenyl-3-yl)-5-methyl-5,6-dihydro-2H-[1,4]oxazin-3-ylamine formate as a white solid after purification by preparative HPLC. MS (ISP): m/z=335.4 [M+H]$^+$.

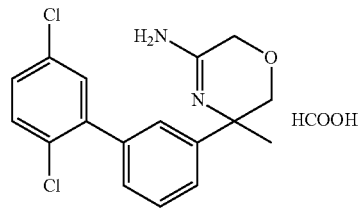 [SMILES: CC1(c2cccc(-c3cc(Cl)ccc3Cl)c2)COCC(N)=N1 ; "HCOOH"]

Example 6

5-Methyl-5-(2',3',5'-trichloro-biphenyl-3-yl)-5,6-dihydro-2H-[1,4]oxazin-3-ylamine or 5-Methyl-5-(2',3',5'-trichloro-biphenyl-3-yl)-5,6-dihydro-2H-[1,4]oxazin-3-ylamine formate With (2,3,5-trichlorophenyl)-boronic acid the 5-methyl-5-(2',3',5'-trichloro-biphenyl-3-yl)-5,6-dihydro-2H-[1,4]oxazin-3-ylamine formate as an amorphous white solid after purification by preparative HPLC. MS (ISP): m/z=371.2 [M+H]$^+$.

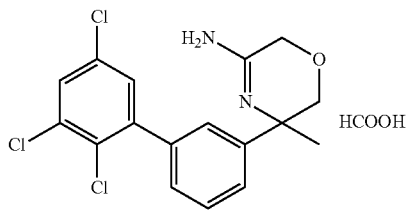 [SMILES: CC1(c2cccc(-c3cc(Cl)cc(Cl)c3Cl)c2)COCC(N)=N1 ; "HCOOH"]

Example 7

5-(3'-Chloro-4'-fluoro-biphenyl-3-yl)-5-methyl-5,6-dihydro-2H-[1,4]oxazin-3-ylamine or 5-(3'-Chloro-4'-fluoro-biphenyl-3-yl)-5-methyl-5,6-dihydro-2H-[1,4]oxazin-3-ylamine formate With (3-chloro-4-fluorophenyl)-boronic acid the 5-(3'-chloro-4'-fluoro-biphenyl-3-yl)-5-methyl-5,6-dihydro-2H-[1,4]oxazin-3-ylamine formate as an amorphous white solid after purification by preparative HPLC. MS (ISP): m/z=319.2 [M+H]$^+$.

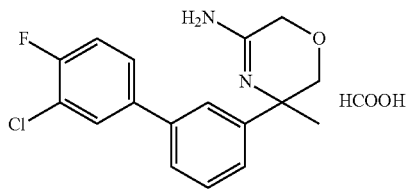 [SMILES: CC1(c2cccc(-c3ccc(F)c(Cl)c3)c2)COCC(N)=N1 ; "HCOOH"]

Example 8

5-(3'-Chloro-5'-methoxy-biphenyl-3-yl)-5-methyl-5,6-dihydro-2H-[1,4]oxazin-3-ylamine or 5-(3'-Chloro-5'-methoxy-biphenyl-3-yl)-5-methyl-5,6-dihydro-2H-[1,4]oxazin-3-ylamine formate With (3-chloro-4-methoxyphenyl)-boronic acid the 5-(3'-chloro-4'-methoxy-biphenyl-3-yl)-5-methyl-5,6-dihydro-2H-[1,4]oxazin-3-ylamine formate as an amorphous white solid after purification by preparative HPLC. MS (ISP): m/z=331.1 [M+H]$^+$.

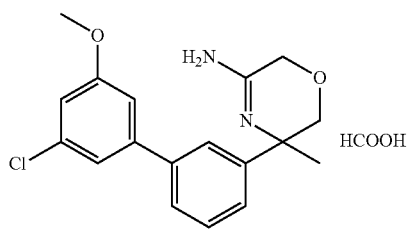 [SMILES: COc1cc(Cl)cc(-c2cccc(C3(C)COCC(N)=N3)c2)c1 ; "HCOOH"]

Example 9

5-(3'-Chloro-5'-methyl-biphenyl-3-yl)-5-methyl-5,6-dihydro-2H-[1,4]oxazin-3-ylamine or 5-(3'-Chloro-5'-methyl-biphenyl-3-yl)-5-methyl-5,6-dihydro-2H-[1,4]oxazin-3-ylamine formate With (3-chloro-5-methylphenyl)boronic acid the 5-(3'-chloro-4'-methyl-biphenyl-3-yl)-5-methyl-5,6-dihydro-2H-[1,4]oxazin-3-ylamine formate as a white solid after purification by preparative HPLC. MS (ISP): m/z=315.2 [M+H]$^+$.

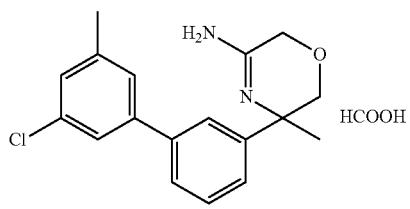 [SMILES: Cc1cc(Cl)cc(-c2cccc(C3(C)COCC(N)=N3)c2)c1 ; "HCOOH"]

Example 10

5-(5'-Chloro-2'-fluoro-3'-methyl-biphenyl-3-yl)-5-methyl-5,6-dihydro-2H-[1,4]oxazin-3-ylamine or 5-(5'-Chloro-2'-fluoro-3'-methyl-biphenyl-3-yl)-5-methyl-5,6-dihydro-2H-[1,4]oxazin-3-ylamine formate With (5-chloro-2-fluoro-3-methylphenyl)-boronic acid the 5-(5'-chloro-2'-fluoro-3'-methyl-biphenyl-3-yl)-5-methyl-5,6-dihydro-2H-[1,4]oxazin-3-ylamine formate as a white solid after purification by preparative HPLC. MS (ISP): m/z=333.2 [M+H]$^+$.

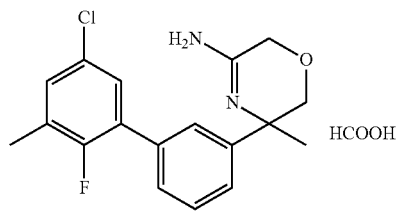

Example 11

5-(5'-Chloro-3'-trifluoromethyl-biphenyl-3-yl)-5-methyl-5,6-dihydro-2H-[1,4]oxazin-3-ylamine or 5-(5'-Chloro-3'-trifluoromethyl-biphenyl-3-yl)-5-methyl-5,6-dihydro-2H-[1,4]oxazin-3-ylamine formate With (5-chloro-3-trifluoromethyl-phenyl)-boronic acid the 5-(5'-chloro-3'-trifluoromethyl-biphenyl-3-yl)-5-methyl-5,6-dihydro-2H-[1,4]oxazin-3-ylamine formate as an amorphous off-white solid after purification by preparative HPLC. MS (ISP): m/z=369.1 [M+H]$^+$.

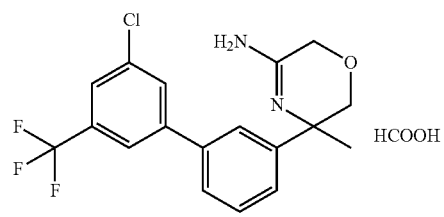 [SMILES: CC1(c2cccc(-c3cc(Cl)cc(C(F)(F)F)c3)c2)COCC(N)=N1 ; "HCOOH"]

Example 12

3'-(5-Amino-3-methyl-3,6-dihydro-2H-[1,4]oxazin-3-yl)-5-chloro-biphenyl-3-carboxylic acid amide or 3'-(5-Amino-3-methyl-3,6-dihydro-2H-[1,4]oxazin-3-yl)-5-chloro-biphenyl-3-carboxylic acid amide formate With [3-(aminocarbonyl)-5-chlorophenyl]-boronic acid the 3'-(5-amino-3-methyl-3,6-dihydro-2H-[1,4]oxazin-3-yl)-5-chloro-biphenyl-3-carboxylic acid amide formate as an amorphous off-white solid after purification by preparative HPLC. MS (ISP): m/z=344.3 [M+H]$^+$.

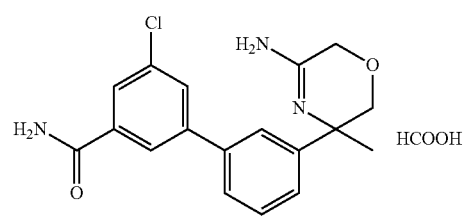 [SMILES: CC1(c2cccc(-c3cc(Cl)cc(C(N)=O)c3)c2)COCC(N)=N1 ; "HCOOH"]

Example 13

[3'-(5-Amino-3-methyl-3,6-dihydro-2H-[1,4]oxazin-3-yl)-5-chloro-biphenyl-3-yl]-morpholin-4-yl-methanone or [3'-(5-Amino-3-methyl-3,6-dihydro-2H-[1,4]oxazin-3-yl)-5-chloro-biphenyl-3-yl]-morpholin-4-yl-methanone formate With [3-chloro-5-(4-morpholinylcarbonyl)phenyl]-boronic acid the [3'-(5-amino-3-methyl-3,6-dihydro-2H-[1,4]oxazin-3-yl)-5-chloro-biphenyl-3-yl]-morpholin-4-yl-methanone formate as an amorphous off-white solid after purification by preparative HPLC. MS (ISP): m/z=414.3 [M+H]$^+$.

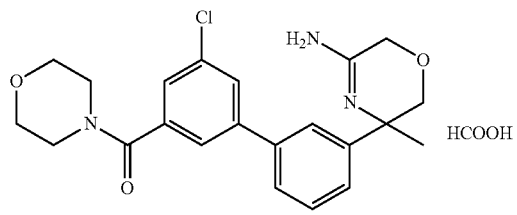 [SMILES: CC1(c2cccc(-c3cc(Cl)cc(C(=O)N4CCOCC4)c3)c2)COCC(N)=N1 ; "HCOOH"]

Example 14

5-(3'-Difluoromethoxy-biphenyl-3-yl)-5-methyl-5,6-dihydro-2H-[1,4]oxazin-3-ylamine or 5-(3'-Difluoromethoxy-biphenyl-3-yl)-5-methyl-5,6-dihydro-2H-[1,4]oxazin-3-ylamine formate With [3-(difluoromethoxy)phenyl]-boronic acid the 5-(3'-difluoromethoxy-biphenyl-3-yl)-5-methyl-5,6-dihydro-2H-[1,4]oxazin-3-ylamine formate as an off-white solid after purification by preparative HPLC. MS (ISP): m/z=333.2 [M+H]$^+$.

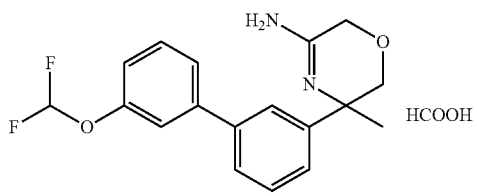 [SMILES: CC1(c2cccc(-c3cccc(OC(F)F)c3)c2)COCC(N)=N1 ; "HCOOH"]

Example 15

5-Methyl-5-(3'-trifluoromethoxy-biphenyl-3-yl)-5,6-dihydro-2H-[1,4]oxazin-3-ylamine or 5-Methyl-5-(3'-trifluoromethoxy-biphenyl-3-yl)-5,6-dihydro-2H-[1,4]oxazin-3-ylamine formate With [3-(trifluoromethoxy)phenyl]-boronic acid the 5-methyl-5-(3'-trifluoromethoxy-biphenyl-3-yl)-5,6-dihydro-2H-[1,4]oxazin-3-ylamine formate as an off-white solid after purification by preparative HPLC. MS (ISP): m/z=351.2 [M+H]$^+$.

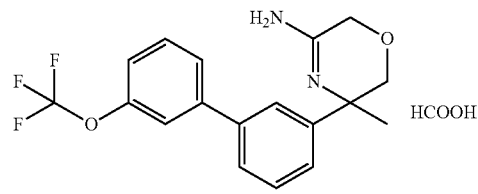 [SMILES: CC1(c2cccc(-c3cccc(OC(F)(F)F)c3)c2)COCC(N)=N1 ; "HCOOH"]

Example 16

3'-(5-Amino-3-methyl-3,6-dihydro-2H-[1,4]oxazin-3-yl)-biphenyl-3-carbonitrile or 3'-(5-Amino-3-methyl-3,6-dihydro-2H-[1,4]oxazin-3-yl)-biphenyl-3-carbonitrile formate With (3-cyanophenyl)-boronic acid the 3'-(5-amino-3-methyl-3,6-dihydro-2H-[1,4]oxazin-3-yl)-biphenyl-3-carbonitrile formate as an amorphous off-white solid after purification by preparative HPLC. MS (ISP): m/z=292.3 [M+H]$^+$.

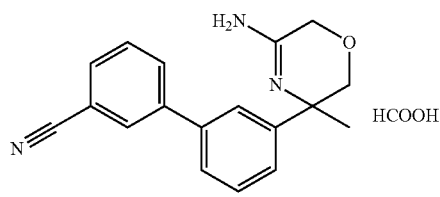 [SMILES: CC1(c2cccc(-c3cccc(C#N)c3)c2)COCC(N)=N1 ; "HCOOH"]

Example 17

[3'-(5-Amino-3-methyl-3,6-dihydro-2H-[1,4]oxazin-3-yl)-biphenyl-3-yl]-acetonitrile or [3'-(5-Amino-3-methyl-3,6-dihydro-2H-[1,4]oxazin-3-yl)-biphenyl-3-yl]-acetonitrile formate With [3-(cyanomethyl)phenyl]-boronic acid the [3'-5-amino-3-methyl-3,6-dihydro-2H-[1,4]oxazin-3-yl)-biphenyl-3-yl]-acetonitrile formate as an amorphous white solid after purification by preparative HPLC. MS (ISP): m/z=306.2 [M+H]$^+$.

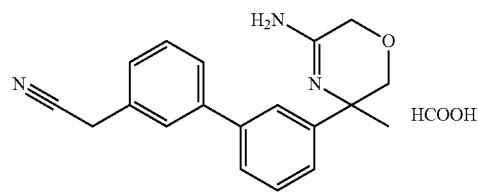 [SMILES: CC1(c2cccc(-c3cccc(CC#N)c3)c2)COCC(N)=N1 ; "HCOOH"]

Example 18

[3'-(5-Amino-3-methyl-3,6-dihydro-2H-[1,4]oxazin-3-yl)-biphenyl-3-yl]-acetonitrile or [3'-(5-Amino-3-methyl-3,6-dihydro-2H-[1,4]oxazin-3-yl)-biphenyl-3-yl]-acetonitrile formate With 4-tert-butyl-boronic acid the 5-(4'-tert-butyl-biphenyl-3-yl)-5-methyl-5,6-dihydro-2H-[1,4]oxazin-3-ylamine formate as a white solid after purification by preparative HPLC. MS (ISP): m/z=323.4 [M+H]$^+$.

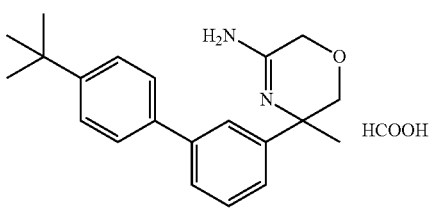 [SMILES: CC(C)(C)c1ccc(-c2cccc(C3(C)COCC(N)=N3)c2)cc1 ; "HCOOH"]

Example 19

5-(4'-tert-Butyl-biphenyl-3-yl)-5-methyl-5,6-dihydro-2H-[1,4]oxazin-3-ylamine or 5-(4'-tert-Butyl-biphenyl-3-yl)-5-methyl-5,6-dihydro-2H-[1,4]oxazin-3-ylamine formate With 2-chloro-pyridine-4-boronic acid the 5-[3-(2-chloro-pyridin-4-yl)-phenyl]-5-methyl-5,6-dihydro-2H-[1,4]oxazin-3-ylamine formate as a purple solid after purification by preparative HPLC. MS (ISP): m/z=302.1 [M+H]$^+$.

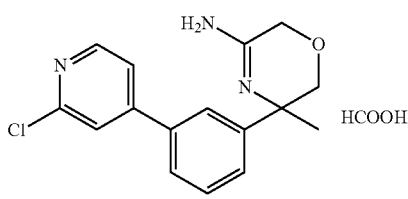 [SMILES: CC1(c2cccc(-c3ccnc(Cl)c3)c2)COCC(N)=N1 ; "HCOOH"]

Example 20

5-[3-(2,5-Dichloro-pyridin-3-yl)-phenyl]-5-methyl-5,6-dihydro-2H-[1,4]oxazin-3-ylamine or 5-[3-(2,5-Dichloro-pyridin-3-yl)-phenyl]-5-methyl-5,6-dihydro-2H-[1,4]oxazin-3-ylamine formate With 2,5-dichloro-pyridine-3-boronic acid the 5-[3-(2,5-dichloro-pyridin-3-yl)-phenyl]-5-methyl-5,6-dihydro-2H-[1,4]oxazin-3-ylamine formate as a white solid after purification by preparative HPLC. MS (ISP): m/z=336.2 [M+H]$^+$.

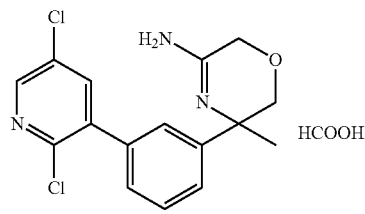 [SMILES: CC1(c2cccc(-c3cc(Cl)cnc3Cl)c2)COCC(N)=N1 ; "HCOOH"]

Example 21

5-[3-(2,2-Difluoro-benzo[1,3]dioxol-5-yl)-phenyl]-5-methyl-5,6-dihydro-2H-[1,4]oxazin-3-ylamine or 5-[3-(2,2-Difluoro-benzo[1,3]dioxol-5-yl)-phenyl]-5-methyl-5,6-dihydro-2H-[1,4]oxazin-3-ylamine formate With 2,2-difluoro-benzo[1,3]dioxole-5-boronic acid the 5-[3-(2,2-difluoro-benzo[1,3]dioxol-5-yl)-phenyl]-5-methyl-5,6-dihydro-2H-[1,4]oxazin-3-ylamine formate as an amorphous off-white material after purification by preparative HPLC. MS (ISP): m/z=347.2 [M+H]$^+$.

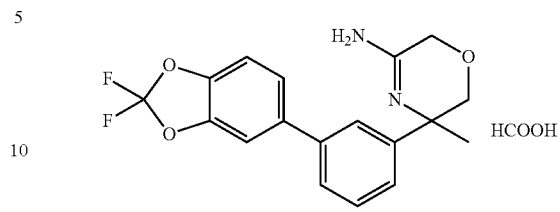

Example 22

5-(3-Benzo[1,3]dioxol-5-yl-phenyl)-5-methyl-5,6-dihydro-2H-[1,4]oxazin-3-ylamine or 5-(3-Benzo[1,3]dioxol-5-yl-phenyl)-5-methyl-5,6-dihydro-2H-[1,4]oxazin-3-ylamine formate With benzo[1,3]dioxole-5-boronic acid the 5-[3-(benzo[1,3]dioxol-5-yl)-phenyl]-5-methyl-5,6-dihydro-2H-[1,4]oxazin-3-ylamine formate as an amorphous off-white material after purification by preparative HPLC. MS (ISP): m/z=347.2 [M+H]$^+$.

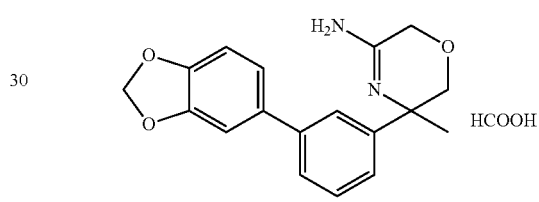

Example 23

5-Methyl-5-[3-(1-methyl-1H-indazol-4-yl)-phenyl]-5,6-dihydro-2H-[1,4]oxazin-3-ylamine or 5-Methyl-5-[3-(1-methyl-1H-indazol-4-yl)-phenyl]-5,6-dihydro-2H-[1,4]oxazin-3-ylamine formate With 1-methyl-1H-indazole-4-boronic acid the 5-methyl-5-[3-(1-methyl-1H-indazol-4-yl)-phenyl]-5,6-dihydro-2H-[1,4]oxazin-3-ylamine formate as an amorphous off-white material after purification by preparative HPLC. MS (ISP): m/z=321.3 [M+H]$^+$.

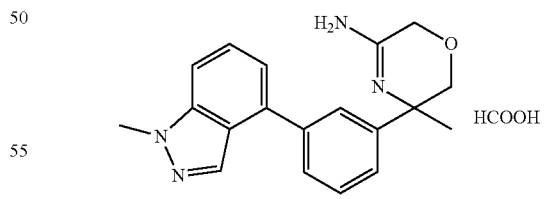

Example 24

5-[3-(6-Chloro-1H-indol-2-yl)-phenyl]-5-methyl-5,6-dihydro-2H-[1,4]oxazin-3-ylamine or 5-[3-(6-Chloro-1H-indol-2-yl)-phenyl]-5-methyl-5,6-dihydro-2H-[1,4]oxazin-3-ylamine hydrochloride a) With 1(tert-butoxyvarbonyl)-6-chloro-1H-indol-2-yl-boronic acid the (RS)-2-[3-(5-amino-3-methyl-3,6-dihydro- 2H-[1,4]oxazin-3-yl)-phenyl]-6-chloro-indole-1-carboxylic acid tert-butyl ester formate as an amorphous off-white material after purification by preparative HPLC. MS (ISP): m/z=440.3 [M+H]⁺.

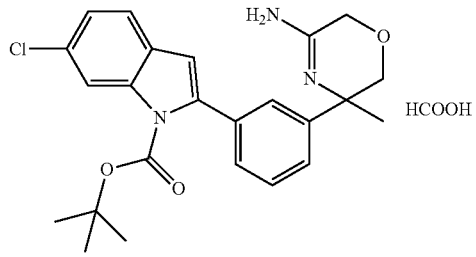 [SMILES: CC(C)(C)OC(=O)n1c(-c2cccc(C3(C)COCC(N)=N3)c2)cc2ccc(Cl)cc21 ; "HCOOH"]

b) A mixture of 2-[3-(5-amino-3-methyl-3,6-dihydro-2H-[1,4]oxazin-3-yl)-phenyl]-6-chloro-indole-1-carboxylic acid tert-butyl ester formate (12 mg, 0.02 mmol) and hydrochloric acid in dioxane (4M) was left at room temperature for 7 hours. For the workup, the solution was evaporated at reduced pressure and the residue dried at high vacuum to yield the (RS)-5-[3-(6-chloro-1H-indol-2-yl)-phenyl]-5-methyl-5,6-dihydro-2H-[1,4]oxazin-3-ylamine hydrochloride as an amorphous brown material. MS (ISP): m/z=340.1 [M+H]⁺.

Example 25

5-[3-(1H-Indol-5-yl)-phenyl]-5-methyl-5,6-dihydro-2H-[1,4]oxazin-3-ylamine or 5-[3-(1H-Indol-5-yl)-phenyl]-5-methyl-5,6-dihydro-2H-[1,4]oxazin-3-ylamine formate With 5-indolyl-boronic acid the 5-[3-(1H-indol-5-yl)-phenyl]-5-methyl-5,6-dihydro-2H-[1,4]oxazin-3-ylamine formate as an amorphous light brown material after purification by preparative HPLC. MS (ISP): m/z=306.4 [M+H]⁺.

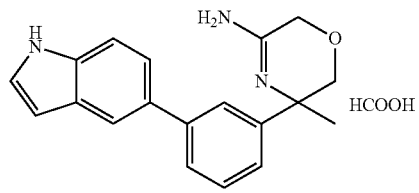 [SMILES: CC1(c2cccc(-c3ccc4[nH]ccc4c3)c2)COCC(N)=N1 ; "HCOOH"]

Example 26

5-(4'-Chloro-3'-methyl-biphenyl-3-yl)-5-methyl-5,6-dihydro-2H-[1,4]oxazin-3-ylamine or 5-(4'-Chloro-3'-methyl-biphenyl-3-yl)-5-methyl-5,6-dihydro-2H-[1,4]oxazin-3-ylamine formate With 4-chloro-3-methylphenyl-boronic acid the (RS)-5-(4'-chloro-3'-methyl-biphenyl-3-yl)-5-methyl-5,6-dihydro- 2H-[1,4]oxazin-3-ylamine formate as an amorphous off-white material after purification by preparative HPLC. MS (ISP): m/z=315.0 [M+H]⁺.

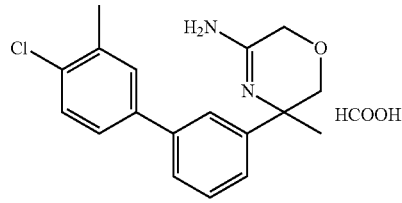 [SMILES: Cc1cc(-c2cccc(C3(C)COCC(N)=N3)c2)ccc1Cl ; "HCOOH"]

Example 27

5-(2',4'-Difluoro-biphenyl-3-yl)-5-methyl-5,6-dihydro-2H-[1,4]oxazin-3-ylamine

A degassed solution of (RS)-5-(3-bromo-phenyl)-5-methyl-5,6-dihydro-2H-[1,4]oxazin-3-ylamine (intermediate XII-1) (100 mg, 0.37 mmol) in 1,2-dimethoxyethane was treated with tetrakis(triphenylphosphine)palladium(0) (42.7 mg, 0.037 mmol), then purged again with argon for 15 minutes. Thereafter, a solution of sodium hydrogencarbonate (1 M, 0.5 ml) and 2,4-difluoro-benzene-boronic acid (116.5 g, 0.74 mmol) were added. The tube was sealed and the mixture heated to 100° C. for 3 hours. For the workup, the reaction mixture was filtered through Celite®, then extracted with dichloromethane (2×15 ml). The combined organic layers were evaporated and the residue was repeatedly (3×) purified by chromatography on a silica-amine phase. The (RS)-5-(2',4'-difluoro-biphenyl-3-yl)-5-methyl-5,6-dihydro-2H-[1,4]oxazin-3-ylamine was obtained as an off-white solid (20 mg, 18% of theory). MS (ISP): m/z=303.4 [M+H]⁺.

Examples 28-30

In close analogy to the procedure described in Example 27, the following compounds were obtained:

Example 28

5-(3',5'-Difluoro-biphenyl-3-yl)-5-methyl-5,6-dihydro-2H-[1,4]oxazin-3-ylamine

With 3,5-difluoro-benzene-boronic acid the 5-(3',5'-difluoro-biphenyl-3-yl)-5-methyl-5,6-dihydro-2H-[1,4]oxazin-3-ylamine as an off-white solid. MS (ISP): m/z=303.0 [M+H]⁺.

Example 29

5-(2'-Chloro-biphenyl-3-yl)-5-methyl-5,6-dihydro-2H-[1,4]oxazin-3-ylamine

With 2-chloro-benzene-boronic acid the 5-(2'-chloro-biphenyl-3-yl)-5-methyl-5,6-dihydro-2H-[1,4]oxazin-3-ylamine as an off-white solid. MS (ISP): m/z=301.4 [M+H]⁺.

Example 30

5-(3'-Ethoxy-biphenyl-3-yl)-5-methyl-5,6-dihydro-2H-[1,4]oxazin-3-ylamine

With 3-ethoxy-benzene-boronic acid the (RS)-5-(3'-ethoxy-biphenyl-3-yl)-5-methyl-5,6-dihydro-2H-[1,4]oxazin-3-ylamine as an off-white solid. MS (ISP): m/z=311 [M+H]⁺.

Example 31

5-(3',5'-Dichloro-6-fluoro-biphenyl-3-yl)-5-methyl-5,6-dihydro-2H-[1,4]oxazin-3-ylamine or 5-(3',5'-Dichloro-6-fluoro-biphenyl-3-yl)-5-methyl-5,6-dihydro-2H-[1,4]oxazin-3-ylamine formate In close analogy to the procedure described in Example 1, the palladium-catalyzed coupling of (RS)-5-(3-bromo-4-fluoro-phenyl)-5-methyl-5,6-dihydro-2H-[1,4]oxazin-3-ylamine (intermediate XII-3) with 3,5-dichloro-phenyl-boronic acid yielded after purification by preparative HPLC the 5-(3',5'-dichloro-6-fluoro-biphenyl-3-yl)-5-methyl-5,6-dihydro-2H-[1,4]oxazin-3-ylamine formate as an off-white solid. MS (ISP): m/z=301.4 [M+H]⁺.

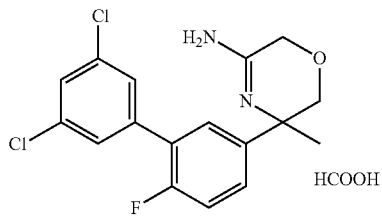 [SMILES: CC1(c2ccc(F)c(-c3cc(Cl)cc(Cl)c3)c2)COCC(N)=N1 ; "HCOOH"]

Example 32

Method B

5-(3',5'-Dichloro-biphenyl-3-yl)-5-methyl-5,6-dihydro-2H-[1,4]oxazin-3-ylamine

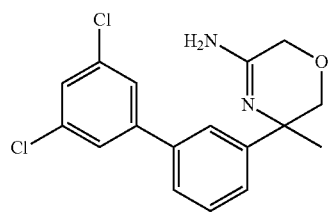 [SMILES: CC1(c2cccc(-c3cc(Cl)cc(Cl)c3)c2)COCC(N)=N1]

a) (RS)-3-(3',5'-Dichloro-biphenyl-3-yl)-5-methoxy-3-methyl-3,6-dihydro-2H-[1,4]oxazine A degassed solution of (RS)-3-(3-bromo-phenyl)-5-methoxy-3-methyl-3,6-dihydro-2H[1,4]oxazine (intermediate XI-1) (200 mg, 0.7 mmol) in 1,2-dimethoxyethane (3 ml) and 2-(3,5-dichloro-phenyl)-4,4,5,5-tetramethyl-[1,3,2]dioxaborolane (288 mg, 1.1 mmol) was treated consecutively with a solution of sodium carbonate (2M, 0.6 ml), triphenylphosphine (38 mg, 0.1 mmol), and palladium(II)acetate (16 mg, 0.1 mmol). The mixture was heated overnight in a sealed tube at 105° C. For the workup, the reaction mixture was evaporated at reduced pressure and the residue directly purified by chromatography on a silica-amine phase using a gradient of heptane/ethylacetate=100/0 to 60/10 as the eluent. The (RS)-3-(3',5'-dichloro-biphenyl-3-yl)-5-methoxy-3-methyl-3,6-dihydro-2H-[1,4]oxazine was obtained as a colorless oil (160 mg, 65% of theory). MS (ISP): m/z=350.2 [M+H]⁺.

b) (RS)-5-(3',5'-Dichloro-biphenyl-3-yl)-5-methyl-5,6-dihydro-2H-[1,4]oxazin-3-ylamine In a manner analogous to that described for the preparation of intermediate XII-1, the treatment of (RS)-3-(3',5'-dichloro-biphenyl-3-yl)-5-methoxy-3-methyl-3,6-dihydro-2H-[1,4]oxazine with ammonium chloride in methanol at 100° C. overnight yielded the title compound as a white foam. MS (ISP): m/z=302.2 [M+H]⁺.

Examples 33-35

In close analogy to the reaction sequence described in Example 32 (method B), the following compounds were obtained by palladium-catalyzed coupling of (RS)-3-(3-bromo-phenyl)-5-methoxy-3-methyl-3,6-dihydro-2H[1,4]oxazine (intermediate XI-1) with boronic acid derivatives followed by the treatment of the corresponding imino-ether with ammonium chloride:

Example 33

5-[3-(5-Chloro-pyridin-2-yl)-phenyl]-5-methyl-5,6-dihydro-2H-[1,4]oxazin-3-ylamine With 5-chloro-pyridine-2-boronic acid the 5-[3-(5-chloro-pyridin-2-yl)-phenyl]-5-methyl-5,6-dihydro-2H-[1,4]oxazin-3-ylamine as a white foam. MS (ISP): m/z=302.2 [M+H]⁺.

Example 34

5-[3-(5-Chloro-pyridin-3-yl)-phenyl]-5-methyl-5,6-dihydro-2H-[1,4]oxazin-3-ylamine With 5-chloro-pyridine-3-boronic acid the 5-[3-(5-chloro-pyridin-3-yl)-phenyl]-5-methyl-5,6-dihydro-2H-[1,4]oxazin-3-ylamine as a white foam. MS (ISP): m/z=302.2 [M+H]⁺.

Example 35

5-Methyl-5-(3-pyrimidin-5-yl-phenyl)-5,6-dihydro-2H-[1,4]oxazin-3-ylamine

With pyrimidine-5-boronic acid the 5-methyl-5-(3-pyrimidin-5-yl-phenyl)-5,6-dihydro-2H-[1,4]oxazin-3-ylamine as a white foam. MS (ISP): m/z=269.3 [M+H]⁺.

Examples 36

5-(2-Fluoro-5-pyrimidin-5-yl-phenyl)-5-methyl-5,6-dihydro-2H-[1,4]oxazin-3-ylamine In close analogy to the reaction sequence described in Example 31 (method B), the palladium-catalyzed coupling of (RS)-3-(5-bromo-2-fluoro-phenyl)-5-methoxy-3-methyl-3,6-dihydro-2H-[1,4]oxazine (intermediate XI-2) with pyrimidine-5-boronic acid followed by the treatment of the corresponding imino-ether with ammonium chloride yielded the 5-(2-fluoro-5-pyrimidin-5-yl-phenyl)-5-methyl-5,6-dihydro-2H-[1,4]oxazin-3-ylamine as a white foam. MS (ISP): m/z=302.2 [M+H]$^+$.

Examples 37

(R)-5-(3',5'-Dichloro-4-fluoro-biphenyl-3-yl)-5-methyl-5,6-dihydro-2H-[1,4]oxazin-3-ylamine or (R)-5-(3',5'-Dichloro-4-fluoro-biphenyl-3-yl)-5-methyl-5,6-dihydro-2H-[1,4]oxazin-3-ylamine formate In analogy to the procedure described in Example 1 (method A), the palladium-catalyzed coupling of (R)-5-(5-bromo-2-fluoro-phenyl)-5-methyl-5,6-dihydro-2H-[1,4]oxazin-3-ylamine (intermediate XII-4) with 3,5-dichloropheny-boronic acid using [1,1'-bis(diphenylphosphino)ferrocene]dichloropalladium(II) as the catalyst in a 2:1-mixture of N,N-dimethylacetamide and water yielded after purification by preparative HPLC the (R)-5-(3',5'-dichloro-4-fluoro-biphenyl-3-yl)-5-methyl-5,6-dihydro-2H-[1,4]oxazin-3-ylamine formate as a white solid. MS (ISP): m/z=353.1 [M+H]$^+$.

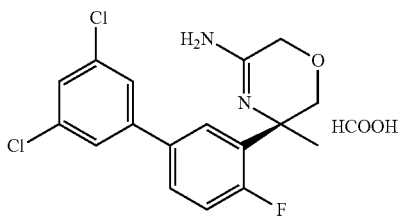 [SMILES: C[C@@]1(c2cc(-c3cc(Cl)cc(Cl)c3)ccc2F)COCC(N)=N1 ; "HCOOH"]

Example 38

Method C 5-(3-(5-Amino-3-methyl-3,6-dihydro-2H-1,4-oxazin-3-yl)phenyl)nicotinonitrile or 5-(3-(5-amino-3-methyl-3,6-dihydro-2H-1,4-oxazin-3-yl)phenyl)nicotinonitrile trifluoroacetate

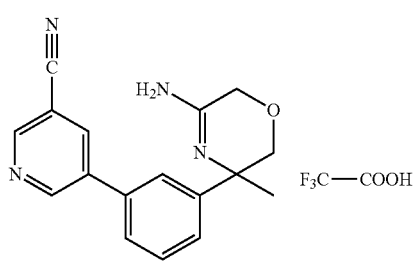

a) (RS)-{5-[3-(5-Cyano-pyridin-3-yl)-phenyl]-5-methyl-5,6-dihydro-2H-[1,4]oxazin-3-yl}-carbamic acid tert-butyl ester In a manner analogous to that described for the preparation of Example 1, the palladium-catalyzed coupling of (RS)-[5-(3-bromo-phenyl)-5-methyl-5,6-dihydro-2H-[1,4]oxazin-3-yl]-carbamic acid tert-butyl ester (intermediate XIII-1) with 5-(4,4,5,5-tetramethyl-[1,3,2]dioxaborolan-2-yl)-nicotinonitrile using [1,1'-bis(diphenylphosphino)ferrocene] dichloro-palladium(II) as the catalyst yielded the title compounds as a white semisolid. MS (ISP): m/z=393.2 [M+H]$^+$.

b) 5-[3-(5-Amino-3-methyl-3,6-dihydro-2H-[1,4] oxazin-3-yl)-phenyl]-nicotinonitrile trifluoroacetate A solution of (RS)-{5-[3-(5-cyano-pyridin-3-yl)-phenyl]-5-methyl-5,6-dihydro-2H-[1,4]oxazin-3-yl}-carbamic acid tert-butyl ester (49 mg, 0.13 mmol) in dichloromethane (1.5 ml) was treated with trifluoroacetic acid (1.03 ml, 13.3 mmol). The orange colored solution was stirred at room temperature for 30 minutes. For the workup, the solution was evaporated at high vacuum. Heptane was added to the oily residue, and the resulting suspension was evaporated at reduced pressure. After drying at high vacuum the title compound was obtained as a brown solid (49 mg, 98% of theory). MS (ISP): m/z=293.1 [M+H]$^+$.

Examples 39-41

In close analogy to the reaction sequence described in Example 38 (method C), the following compounds were obtained by palladium-catalyzed coupling of (RS)-[5-(3-bromo-phenyl)-5-methyl-5,6-dihydro-2H-[1,4]oxazin-3-yl]-carbamic acid tert-butyl ester (intermediate XIII-1) with boronic acid derivatives followed by the cleavage of the N-protecting group with trifluoroacetic acid:

Example 39

5-(3-(2-fluoropyridin-3-yl)phenyl)-5-methyl-5,6-dihydro-2H-1,4-oxazin-3-amine or 5-(3-(2-fluoropyridin-3-yl)phenyl)-5-methyl-5,6-dihydro-2H-1,4-oxazin-3-amine trifluoroacetate With 2-fluoro-pyridine-3-boronic acid via the intermediate (RS)-{5-[3-(2-fluoro-pyridin-3-yl)-phenyl]-5-methyl-5,6-dihydro-2H-[1,4]oxazin-3-yl}-carbamic acid tert-butyl ester {MS (ISP): m/z=386.2 [M+H]$^+$} the 5-[3-(2-fluoro-pyridin-3-yl)-phenyl]-5-methyl-5,6-dihydro-2H-[1,4]oxazin-3-ylamine trifluoroacetate as a brown solid. MS (ISP): m/z=286.1 [M+H]$^+$.

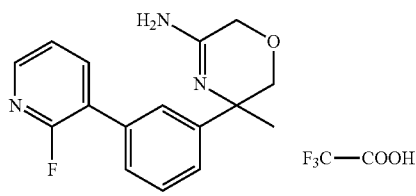 [SMILES: CC1(c2cccc(-c3cccnc3F)c2)COCC(N)=N1 ; O=C(O)C(F)(F)F]

Example 40

5-(3-(2,6-difluoropyridin-3-yl)phenyl)-5-methyl-5,6-dihydro-2H-1,4-oxazin-3-amine or 5-(3-(2,6-difluoropyridin-3-yl)phenyl)-5-methyl-5,6-dihydro-2H-1,4-oxazin-3-amine trifluoroacetate With 2,6-difluoro-pyridine-3-boronic acid via the intermediate (RS)-{5-[3-(2,6-difluoro-pyridin-3-yl)-phenyl]-5-methyl-5,6-dihydro-2H-[1,4]oxazin-3-yl}-carbamic acid tert-butyl ester {MS (ISP): m/z=404.4 [M+H]$^+$} the 5-[3-(2,6- difluoro-pyridin-3-yl)-phenyl]-5-methyl-5,6-dihydro-2H-[1,4]oxazin-3-ylamine trifluoroacetate as a brown solid. MS (ISP): m/z=304.1 [M+H]⁺.

Example 41

5-(3'-Amino-biphenyl-3-yl)-5-methyl-5,6-dihydro-2H-[1,4]oxazin-3-ylamine

With 3-amino-benzene-boronic acid, tetrakis(triphenylphosphine)palladium(0) as the catalyst (cf. example 27), and potassium carbonate as the base in dimethylformamide the intermediate (RS)-[5-(3'-amino-biphenyl-3-yl)-5-methyl-5,6-dihydro-2H-[1,4]oxazin-3-yl]-carbamic acid tert-butyl ester and, thereof, the (RS)-5-(3'-amino-biphenyl-3-yl)-5-methyl-5,6-dihydro-2H-[1,4]oxazin-3-ylamine as an off-white solid. MS (ISP): m/z=282.5 [M+H]⁺.

Example 42

Method D

5-[3-(3-Methoxy-prop-1-ynyl)-phenyl]-5-methyl-5,6-dihydro-2H-[1,4]oxazin-3-ylamine Under an argon atmosphere a solution of (RS)-5-(3-iodo-phenyl)-5-methyl-5,6-dihydro-2H-[1,4]oxazin-3-ylamine (intermediate XII-2) (103 mg, 0.3 mmol) and 3-methoxy-propyne (86 μl, 1 mmol) in dimethylformamide (3 ml) was prepared (solution 1). Likewise, a solution of bis(triphenylphosphine)palladium(II)chloride (14 mg, 0.02 mmol), triphenylphosphine (5 mg, 0.02 mmol), copper(I)iodide (1 mg, 0.005 mmol), and triethylamine (0.23 ml, 1.6 mmol) in dimethylformamide (3 ml) was prepared (solution 2). Solution 2 was warmed to 40° C., then solution 1 was added and the mixture heated to 60° C. The progress of the reaction was checked by mass spectroscopy and after 45 minutes a lot of starting material was left. Additional 3-methoxy-propyne (86 μl, 1 mmol) was added and after 30 minutes the reaction was almost complete. For the workup, the solvent was evaporated at reduced pressure and the residue residue directly purified by chromatography on a silica-amine column using dichloromethane as the eluent. The 5-[3-(3-methoxy-prop-1-ynyl)-phenyl]-5-methyl-5,6-dihydro-2H-[1,4]oxazin-3-ylamine was obtained as a light yellow foam (61 mg, 73% of theory). MS (ISP): m/z=259.3 [M+H]⁺.

Example 43

5-[3-(5-Chloro-pyridin-2-ylethynyl)-phenyl]-5-methyl-5,6-dihydro-2H-[1,4]oxazin-3-ylamine In a manner analogous to that described in Example 42, the reaction of (RS)-5-(3-iodo-phenyl)-5-methyl-5,6-dihydro-2H-[1,4]oxazin-3-ylamine (intermediate XII-2) with 5-chloro-2-trimethylsilanylethynyl-pyridine (EP385210) was performed. In addition, after combination of solution 1 and 2, a solution of tetrabutylammonium fluoride in tetrahydrofuran (1M, 0.47 ml) was added. The 5-[3-(5-chloro-pyridin-2-ylethynyl)-phenyl]-5-methyl-5,6-dihydro-2H-[1,4]oxazin-3-ylamine was obtained as a white foam. MS (ISP): m/z=326.3 [M+H]⁺.

Examples 44-46

In a manner analogous to that described in Example 27, the following compounds were obtained by the cross-coupling reaction of (RS)-5-(3-bromo-phenyl)-5-(4-difluoromethoxy-3-methyl-phenyl)-5,6-dihydro-2H-[1,4]oxazin-3-ylamine (intermediate XII-5) with boronic acid derivatives, tetrakis(triphenylphosphine)palladium(0) as the catalyst, cesium carbonate as the base at 75° C. for 2 hours. For the workup, the reaction mixtures were loaded onto a SCX-cartridge. A 1:1-mixture of dichloromethane and methanol was passed through the column to remove impurities and the products were eluted with a solution of ammonia in methanol (2.0M). the crude products were purified by mass triggered preparative HPLC followed by treatment with hydrochloric acid and evaporation:

Example 44

5-(4-Difluoromethoxy-3-methyl-phenyl)-5-(3-pyridin-3-yl-phenyl)-5,6-dihydro-2H-[1,4]oxazin-3-ylamine or 5-(4-Difluoromethoxy-3-methyl-phenyl)-5-(3-pyridin-3-yl-phenyl)-5,6-dihydro-2H-[1,4]oxazin-3-ylamine hydrochloride With pyridine-3-boronic acid the 5-(4-difluoromethoxy-3-methyl-phenyl)-5-(3-pyridin-3-yl-phenyl)-5,6-dihydro-2H-[1,4]oxazin-3-ylamine hydrochloride (32% of theory). MS (ISP): m/z=411 [M+H]⁺.

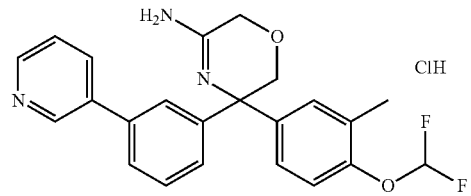 [SMILES: Cc1cc(C2(c3cccc(-c4cccnc4)c3)COCC(N)=N2)ccc1OC(F)F ; Cl]

Example 45

5-[3-(6-Chloro-pyridin-3-yl)-phenyl]-5-(4-difluoromethoxy-3-methyl-phenyl)-5,6-dihydro-2H-[1,4]oxazin-3-ylamine or 5-[3-(6-Chloro-pyridin-3-yl)-phenyl]-5-(4-difluoromethoxy-3-methyl-phenyl)-5,6-dihydro-2H-[1,4]oxazin-3-ylamine hydrochloride With 6-chloro-pyridine-3-boronic acid the 5-[3-(6-chloro-pyridin-3-yl)-phenyl]-5-(4-difluoromethoxy-3-methyl-phenyl)-5,6-dihydro-2H-[1,4]oxazin-3-ylamine hydrochloride (4% of theory). MS (ISP): m/z=444 [M+H]⁺.

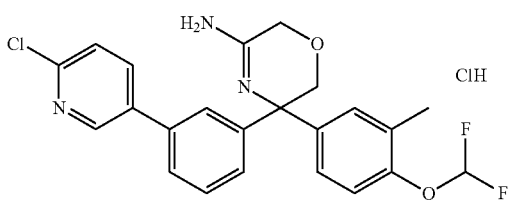 [SMILES: Cc1cc(C2(c3cccc(-c4ccc(Cl)nc4)c3)COCC(N)=N2)ccc1OC(F)F ; Cl]

Example 46

5-[3-(5-Chloro-pyridin-3-yl)-phenyl]-5-(4-difluoromethoxy-3-methyl-phenyl)-5,6-dihydro-2H-[1,4]oxazin-3-ylamine or 5-[3-(5-Chloro-pyridin-3-yl)-phenyl]-5-(4-difluoromethoxy-3-methyl-phenyl)-5,6-dihydro-2H-[1,4]oxazin-3-ylamine hydrochloride With 5-chloro-pyridine-3-boronic acid the 5-[3-(5-chloro-pyridin-3-yl)-phenyl]-5-(4-difluoromethoxy-3-methyl-phenyl)-5,6-dihydro-2H-[1,4]oxazin-3-ylamine hydrochloride (16% of theory). MS (ISP): m/z=444 [M+H]$^+$.

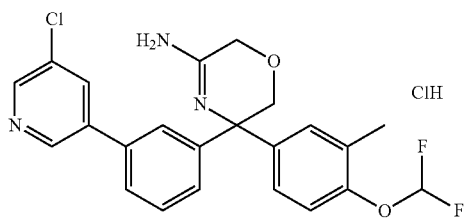 [SMILES: Cc1cc(C2(c3cccc(-c4cncc(Cl)c4)c3)COCC(N)=N2)ccc1OC(F)F ; Cl]

Examples 47-48

In a manner analogous to that described for Examples 44-46, the following compounds were obtained by the palladium-catalyzed cross-coupling reaction of (RS)-5-(3-bromophenyl)-5-(6-difluoromethoxy-pyridin-3-yl)-5,6-dihydro-2H-[1,4]oxazin-3-ylamine (XII-6):

Example 47

5-[3-(5-Chloro-pyridin-3-yl)-phenyl]-5-(6-difluoromethoxy-pyridin-3-yl)-5,6-dihydro-2H-[1,4]oxazin-3-ylamine or 5-[3-(5-Chloro-pyridin-3-yl)-phenyl]-5-(6-difluoromethoxy-pyridin-3-yl)-5,6-dihydro-2H-[1,4]oxazin-3-ylamine hydrochloride With 5-chloro-pyridine-3-boronic acid the 5-[3-(5-chloro-pyridin-3-yl)-phenyl]-5-(6-difluoromethoxy-pyridin-3-yl)-5,6-dihydro-2H-[1,4]oxazin-3-ylamine hydrochloride (44% of theory). MS (ISP): m/z=431 [M+H]$^+$.

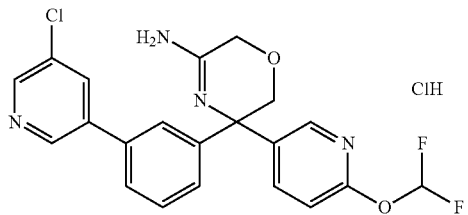 [SMILES: NC1=NC(c2ccc(OC(F)F)nc2)(c2cccc(-c3cncc(Cl)c3)c2)COC1 ; Cl]

Example 48

5-(6-Difluoromethoxy-pyridin-3-yl)-5-[3-(5-methoxy-pyridin-3-yl)-phenyl]-5,6-dihydro-2H-[1,4]oxazin-3-ylamine or 5-(6-Difluoromethoxy-pyridin-3-yl)-5-[3-(5-methoxy-pyridin-3-yl)-phenyl]-5,6-dihydro-2H-[1,4]oxazin-3-ylamine hydrochloride With 5-methoxy-pyridine-3-boronic acid the 5-(6-difluoromethoxy-pyridin-3-yl)-5-[3-(5-methoxy-pyridin-3-yl)-phenyl]-5,6-dihydro-2H-[1,4]oxazin-3-ylamine hydrochloride (18% of theory). MS (ISP): m/z=427 [M+H]$^+$.

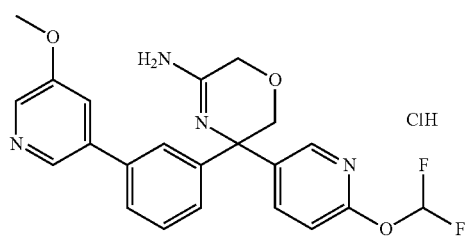 [SMILES: COc1cncc(-c2cccc(C3(c4ccc(OC(F)F)nc4)COCC(N)=N3)c2)c1 ; Cl]

Example 49

Method E

5-[3-(6-Chloro-benzooxazol-2-yl)-phenyl]-5-methyl-5,6-dihydro-2H-[1,4]oxazin-3-ylamine or 5-[3-(6-Chloro-benzooxazol-2-yl)-phenyl]-5-methyl-5,6-dihydro-2H-[1,4]oxazin-3-ylamine hydrochloride

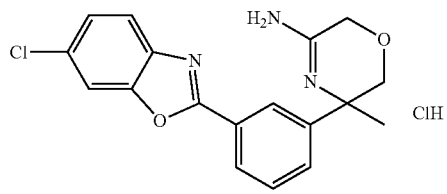 [SMILES: CC1(c2cccc(-c3nc4ccc(Cl)cc4o3)c2)COCC(N)=N1 ; Cl]

a) 5-[3-(6-Chloro-benzooxazol-2-yl)-phenyl]-5-methyl-morpholin-3-one

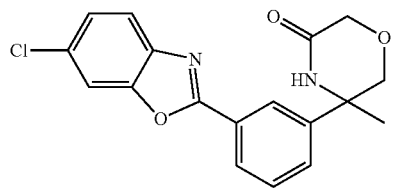

A mixture of 3-((RS)-3-methyl-5-oxo-morpholin-3-yl)-benzoic acid (intermediate XXVI-1) (250 mg, 1.1 mmol) and 2-amino-5-chloro-phenol (230 mg, 1.6 mmol) in polyphosphoric acid (1 g) was heated under stirring at 130° C. for 3 hours. For the workup, the reaction mixture was cooled and water was added. The mixture was neutralized with an aqueous solution of sodium hydroxide (10%), then extracted with dichloromethane. The organic layer was dried over sodium sulphate and evaporated to yield the (RS)-5-[3-(6-chloro-benzooxazol-2-yl)-phenyl]-5-methyl-morpholin-3-one (316 mg, 87% of theory) in a quality suited to be engaged in the next step without further purification. MS (ISP): m/z=343 [M+H]$^+$.

b) 5-[3-(6-Chloro-benzooxazol-2-yl)-phenyl]-5-methyl-morpholin-3-thione

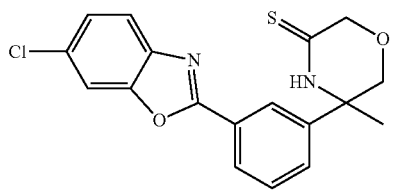 [SMILES: CC1(c2cccc(-c3nc4ccc(Cl)cc4o3)c2)COCC(=S)N1]

In close analogy to the procedure described for the preparation of Intermediate XVIII-1, the reaction of (RS)-5-[3-(6-chloro-benzooxazol-2-yl)-phenyl]-5-methyl-morpholin-3-one with Lawesson's reagent yielded the title compound (79% of theory). MS (ISP): m/z=359.1 [M+H]$^+$.

c) 5-[3-(6-Chloro-benzooxazol-2-yl)-phenyl]-5-methyl-5,6-dihydro-2H-[1,4]oxazin-3-ylamine Hydrochloride In a tube the (RS)-5-[3-(6-chloro-benzooxazol-2-yl)-phenyl]-5-methyl-morpholin-3-thione (260 mg, 0.7 mmol) was treated with a solution of ammonia in methanol (7M). The sealed tube was heated at 100° C. for 3 hours. For the workup, the reaction mixture was cooled to room temperature and evaporated. For purification the crude product was passed on a SCX column, and then further purified by preparative HPLC. Finally, the treatment with hydrochloric acid followed by evaporation yielded the title compound (23 mg, 9% of theory) MS (ISP): m/z=342 [M+H]$^+$.

Example 50

5-[3-(5-Chloro-1H-benzoimidazol-2-yl)-phenyl]-5-methyl-5,6-dihydro-2H-[1,4]oxazin-3-ylamine a) 5-[3-(6-Chloro-1H-benzoimidazol-2-yl)-phenyl]-5-methyl-morpholin-3-one

A solution of 3-((RS)-3-methyl-5-oxo-morpholin-3-yl)-benzoic acid (intermediate XXVI-1) (200 mg, 0.89 mmol), triethylamine (0.13 ml, 0.93 mmol), and O-(benzotriazol-1-yl)-N,N,N',N'-tetramethyluronium tetrafluoroborate (TBTU) (285 mg, 0.89 mmol) in a 3:1-mixture of dichloromethane and N,N-dimethylformamide was stirred at room temperature for 1 hour. Thereafter, 4-chloro-benzene-1,2-diamine (151 mg, 1.06 mmol) was added and stirring continued at room temperature. The progress of the reaction was followed by HPLC. After complete consumption of the acid, the reaction mixture was treated with water. The organic layer was separated and concentrated at reduced pressure. The solution was passed through a silica-NH$_2$ cartridge using a mixture of dichloromethane and methanol as the eluent. Furthermore, the crude product was purified by chromatography on silica gel using a gradient of dichloromethane/methanol=100/0 to 94/6 as the eluent yielding the intermediate (RS)—N-(2-amino-4(5)-chloro-phenyl)-3-(3-methyl-5-oxo-morpholin-3-yl)-benzamide (287 mg, 90% of theory). In order to complete the ring closure, the intermediate benzamide was dissolved in acetic acid (2 ml) and heated at 80° C. For the workup, the solution was evaporated at reduced pressure, the residue passed on a SCX column, which was eluted with a 1:1-mixture of dichloromethane and methanol, then with a solution of ammonia in methanol (3M) to recover the title compound. After evaporation 202 mg of the 5-[3-(6-chloro-1H-benzoimidazol-2-yl)-phenyl]-5-methyl-morpholin-3-one were obtained.

b) 5-[3-(6-Chloro-1H-benzoimidazol-2-yl)-phenyl]-5-methyl-morpholin-3-thione

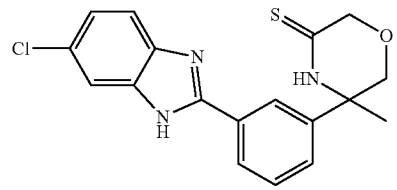

In close analogy to the procedure described for the preparation of Intermediate XVIII-1, the reaction of 5-[3-(6-chloro-1H-benzoimidazol-2-yl)-phenyl]-5-methyl-morpholin-3-one (202 mg, 0.6 mmol) with Lawesson's reagent yielded the title compound (210 mg, 98% of theory).

c) 5-[3-(6-Chloro-1H-benzoimidazol-2-yl)-phenyl]-5-methyl-5,6-dihydro-2H-[1,4]oxazin-3-ylamine In a manner analogous to that described for the preparation of the intermediate XII-3, the ammonolysis of (RS)-5-[3-(6-Chloro-1H-benzoimidazol-2-yl)-phenyl]-5-methyl-morpholin-3-thione (210 mg, 0.6 mmol) yielded the title compound (34 mg, 17% of theory).

Examples 51-52

In close analogy to the procedure described in Example 1 (method A), the following compounds were obtained by palladium-catalyzed coupling of (RS)-5-(5-bromo-2-fluoro-phenyl)-5-difluoromethyl-5,6-dihydro-2H-[1,4]oxazin-3-ylamine (CAS 1262859-04-0; WO2011009943) with boronic acid derivatives using [1,1'-bis(diphenylphosphino)ferrocene]dichloropalladium(II) as the catalyst. In the following examples instead of a mixture of tetrahydrofuran and water a 3:1-mixture of N,N-dimethylacetamide and water was used as the solvent and with a reaction time of 15 minutes.

Example 51

5-Difluoromethyl-5-(2-fluoro-5-pyrimidin-5-yl-phenyl)-5,6-dihydro-2H-[1,4]oxazin-3-ylamine

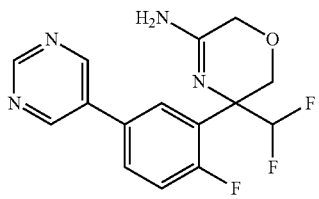

With pyrimidine-5-boronic acid the (RS)-5-difluoromethyl-5-(2-fluoro-5-pyrimidin-5-yl-phenyl)-5,6-dihydro-2H-[1,4]oxazin-3-ylamine as a white solid after purification by preparative HPLC. MS (ISP): m/z=323.2 [M+H]$^+$.

Example 52

5-[5-(5-Chloro-pyridin-3-yl)-2-fluoro-phenyl]-5-difluoromethyl-5,6-dihydro-2H-[1,4]oxazin-3-ylamine

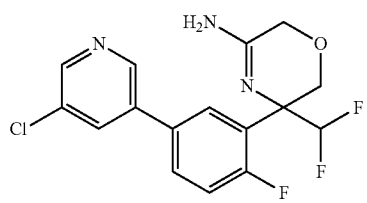 [SMILES: NC1=NC(c2cc(-c3cncc(Cl)c3)ccc2F)(C(F)F)COC1]

With 5-chloro-pyridine-3-boronic acid the (RS)-5-[5-(5-chloro-pyridin-3-yl)-2-fluoro-phenyl]-5-difluoromethyl-5,6-dihydro-2H-[1,4]oxazin-3-ylamine as a white solid after purification by preparative HPLC. MS (ISP): m/z=356.0 [M+H]$^+$.

Example 53

5-[3-(5-Chloro-benzooxazol-2-yl)-phenyl]-5-methyl-5,6-dihydro-2H-[1,4]oxazin-3-ylamine or (RS)-5-[3-(5-Chloro-benzooxazol-2-yl)-phenyl]-5-methyl-5,6-dihydro-2H-[1,4]oxazin-3-ylamine hydrochloride

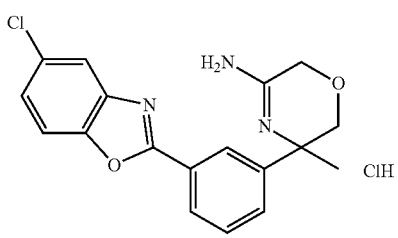 [SMILES: CC1(c2cccc(-c3nc4cc(Cl)ccc4o3)c2)COCC(N)=N1 ; Cl]

In a reaction sequence analogous to that described for the preparation of Example 49 (method E) the title compounds were obtained as follows:

a) (RS)-5-[3-(5-Chloro-benzooxazol-2-yl)-phenyl]-5-methyl-morpholin-3-one

The condensation of 3-((RS)-3-methyl-5-oxo-morpholin-3-yl)-benzoic acid (intermediate XXVI-1) and 2-amino-4-chloro-phenol with polyphosphoric acid at 130° C. during 3 hours yielded the title compound.

b) (RS)-5-[3-(5-Chloro-benzooxazol-2-yl)-phenyl]-5-methyl-morpholin-3-thione

In close analogy to the procedure described for the preparation of Intermediate XVIII-1, the reaction of (RS)-5-[3-(5-chloro-benzooxazol-2-yl)-phenyl]-5-methyl-morpholin-3-one with Lawesson's reagent yielded the title compound (57% of theory). MS (ISP): m/z=359.1 [M+H]$^+$.

c) 5-[3-(5-Chloro-benzooxazol-2-yl)-phenyl]-5-methyl-5,6-dihydro-2H-[1,4]oxazin-3-ylamine Hydrochloride The reaction of (RS)-5-[3-(5-chloro-benzooxazol-2-O-phenyl]-5-methyl-morpholin-3-thione with a solution of ammonia in methanol in a sealed tube at 100° C. during 3 hours followed by the purification on preparative HPLC and, finally, treatment with hydrochloric acid yielded the title compound (9% of theory). MS (ISP): m/z=343 [M+H]$^+$.

Example 54-55

In a manner analogous to that described in Example 42, the reaction of (RS)-5-(3-iodo-phenyl)-5-methyl-5,6-dihydro-2H-[1,4]oxazin-3-ylamine (intermediate XII-2) with ethynyl derivatives was performed. In case of silylated ethynyl derivatives, after combination of solution 1 and 2, a solution of tetrabutylammonium fluoride in tetrahydrofuran (1M) was added.

Example 54

5-Methyl-5-(3-phenylethynyl-phenyl)-5,6-dihydro-2H-[1,4]oxazin-3-ylamine

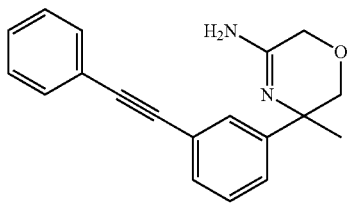 [SMILES: CC1(c2cccc(C#Cc3ccccc3)c2)COCC(N)=N1]

The reaction with 1-phenyl-2-(trimethylsilyl)-acetylene yielded the title compound as a yellow foam. MS (ISP): m/z=291.3 [M+H]$^+$.

Example 55

5-Methyl-5-(3-thiophen-3-ylethynyl-phenyl)-5,6-dihydro-2H-[1,4]oxazin-3-ylamine

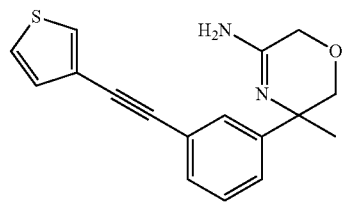 [SMILES: CC1(c2cccc(C#Cc3ccsc3)c2)COCC(N)=N1]

The reaction with 3-ethynylthiophene yielded the title compound as a light brown foam. MS (ISP): m/z=297.4 [M+H]$^+$.

Examples 56-59

In close analogy to the procedure described in Example 1 (method A), the following compounds were obtained by palladium-catalyzed coupling of (RS)-5-(3-bromo-phenyl)-5-methyl-5,6-dihydro-2H-[1,4]oxazin-3-ylamine (intermediate XII-1) with boronic acid derivatives using [1,1'-bis(diphenylphosphino)ferrocene]dichloropalladium(II) as the catalyst. In the following examples instead of a mixture of tetrahydrofuran and water a 2:1-mixture of N,N-dimethylacetamide and water was used as the solvent and with reaction times between 10 minutes and 5 hours.

Example 56

5-(4',5'-Difluoro-3'-methoxy-biphenyl-3-yl)-5-methyl-5,6-dihydro-2H-[1,4]oxazin-3-ylamine formate

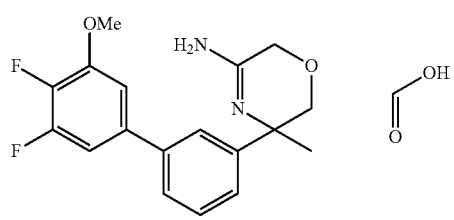 [SMILES: COc1cc(-c2cccc(C3(C)COCC(N)=N3)c2)cc(F)c1F ; O=CO]

With 3,4-difluoro-5-methoxyphenylboronic acid the title compound as a white solid after purification by preparative HPLC. MS (ISP): m/z=333.4 [M+H]$^+$.

Example 57

5-(3',5'-Bis-trifluoromethyl-biphenyl-3-yl)-5-methyl-5,6-dihydro-2H-[1,4]oxazin-3-ylamine formate

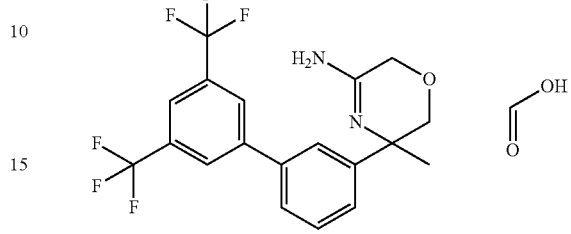

With 3,5-bis(trifluoromethyl)benzeneboronic acid the title compound as an amorphous off-white material after purification by preparative HPLC. MS (ISP): m/z=403.3 [M+H]$^+$.

Example 58

5-[4'-Fluoro-3'-(2,2,2-trifluoro-ethoxy)-biphenyl-3-yl]-5-methyl-5,6-dihydro-2H-[1,4]oxazin-3-ylamine formate

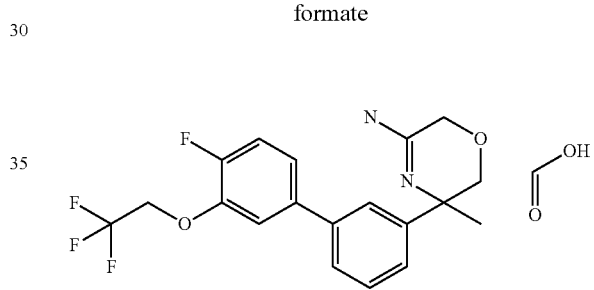

With 4-fluoro-3-(2,2,2-trifluoroethoxy)phenylboronic acid the title compound as an amorphous off-white material after purification by preparative HPLC. MS (ISP): m/z=383.3 [M+H]$^+$.

Example 59

5-[3-(7-Methoxy-naphthalen-2-yl)-phenyl]-5-methyl-5,6-dihydro-2H-[1,4]oxazin-3-ylamine formate

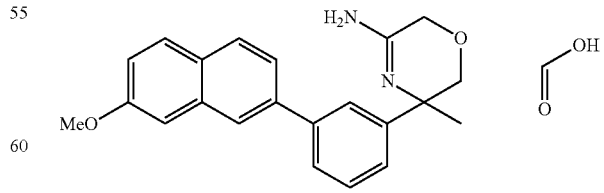

With 2-(7-methoxynaphthalen-2-yl)-4,4,5,5-tetramethyl-1,3,2-dioxaborolane (CAS 627526-31-2) the title compound as an amorphous light brown material after purification by preparative HPLC. MS (ISP): m/z=347.2 [M+H]$^+$.

The invention claimed is:
1. A compound of formula I

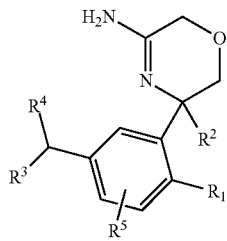

wherein
$R^1$ is selected from the group consisting of
i) hydrogen,
ii) halogen, and
iii) $C_{1-6}$-alkyl;
$R^2$ is selected from the group consisting of
i) hydrogen,
ii) $C_{1-6}$-alkyl,
iii) heteroaryl,
iv) heteroaryl substituted by 1-4 substituents individually selected from halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl,
v) aryl, and
vi) aryl substituted by 1-4 substituents individually selected from halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl;
$R^3$ and $R^4$ together with the C to which they are attached form a group selected from the group consisting of
i) aryl,
ii) aryl substituted by 1-4 substituents individually selected from acetamidyl, amino, amido, —C(O)-heterocyclyl, cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl,
iii) heteroaryl,
iv) heteroaryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl,
v) $C_{2-6}$-alkynyl,
vi) $C_{2-6}$-alkynyl substituted by 1-5 substituents individually selected from aryl, cyano, halogen-aryl, halogen, halogen-heteroaryl, heteroaryl, ydroxyl, $C_{1-6}$-alkyl, $C_{1-6}$-alkyl-aryl, $C_{1-6}$-alkyl-heteroaryl and $C_{1-6}$-alkoxy,
vii) $C_{3-6}$-cycloalkyl,
viii) $C_{3-6}$-cycloalkyl substituted by 1-4 substituents individually selected from cyano, cyano-$C_{1-6}$-alkyl, halogen, halogen-$C_{1-6}$-alkoxy, halogen-$C_{1-6}$-alkyl, ydroxyl, $C_{1-6}$-alkoxy, $C_{1-6}$-alkoxy-$C_{1-6}$-alkyl and $C_{1-6}$-alkyl,
ix) heterocyclyl, and
x) heterocyclyl substituted by 1-4 substituents individually selected from halogen, halogen-$C_{1-6}$-alkoxy, halogen-$C_{1-6}$-alkyl, ydroxyl, $C_{1-6}$-alkoxy, $C_{1-6}$-alkoxy-$C_{1-6}$-alkyl and $C_{1-6}$-alkyl;
$R^5$ is selected from the group consisting of
i) hydrogen,
ii) halogen, and
iii) $C_{1-6}$-alkyl;
or a pharmaceutically acceptable salt thereof.

2. The compound of claim 1, wherein
$R^1$ is selected from the group consisting of
i) hydrogen and
ii) halogen;
$R^2$ is selected from the group consisting of
i) $C_{1-6}$-alkyl,
ii) heteroaryl substituted by halogen-$C_{1-6}$-alkoxy,
iii) aryl substituted by 1-2 substituents individually selected from halogen-$C_{1-6}$-alkoxy and $C_{1-6}$-alkyl,
$R^3$ and $R^4$ together with the C to which they are attached form a group selected from the group consisting of
i) aryl substituted by 1-3 substituents individually selected from acetamidyl, amino, —C(O)-heterocyclyl, cyano, cyano-$C_{1-6}$-alkyl, halogen, halogen-$C_{1-6}$-alkoxy, halogen-$C_{1-6}$-alkyl, $C_{1-6}$-alkoxy and $C_{1-6}$-alkyl,
ii) heteroaryl,
iii) heteroaryl substituted by 1-2 substituents individually selected from cyano, halogen, $C_{1-6}$-alkoxy and $C_{1-6}$-alkyl, and
iv) $C_{2-6}$-alkynyl substituted by 1 substituent selected from halogen-heteroaryl and $C_{1-6}$-alkoxy;
$R^5$ is selected from the group consisting of
i) hydrogen and
ii) halogen.

3. The compound of claim 1, wherein $R^1$ is halogen.
4. The compound of claim 2, wherein $R^1$ is F.
5. The compound of claim 1, wherein $R^1$ is hydrogen.
6. The compound of claim 1, wherein $R^2$ is selected from the group consisting of $C_{1-6}$-alkyl, heteroaryl substituted by halogen-$C_{1-6}$-alkoxy, and aryl substituted by 1-2 substituents individually selected from halogen-$C_{1-6}$-alkoxy and $C_{1-6}$-alkyl.
7. The compound of claim 1, wherein $R^2$ is selected from the group consisting of 4-difluoromethoxy-3-methyl-phenyl, 6-difluoromethoxy-pyridin-3-yl and methyl.
8. The compound of claim 1, wherein $R^3$ and $R^4$ together with the C to which they are attached form a group selected from the group consisting of
i) aryl substituted by 1-3 substituents individually selected from acetamidyl, amino, —C(O)-heterocyclyl, cyano, cyano-$C_{1-6}$-alkyl, halogen, halogen-$C_{1-6}$-alkoxy, halogen-$C_{1-6}$-alkyl, $C_{1-6}$-alkoxy and $C_{1-6}$-alkyl,
ii) heteroaryl,
iii) heteroaryl substituted by 1-2 substituents individually selected from cyano, halogen, $C_{1-6}$-alkoxy and $C_{1-6}$-alkyl, and
iv) $C_{2-6}$-alkynyl substituted by 1 substituent selected from halogen-heteroaryl and $C_{1-6}$-alkoxy.
9. The compound of claim 1, wherein $R^3$ and $R^4$ together with the C to which they are attached form a group selected from the group consisting of 5-methoxy-pyridin-3-yl, 2,6-difluoropyridin-3-yl, 2-fluoropyridin-3-yl, 3,5-dichloro-phenyl, pyridin-3-yl, 5-chloro-pyridin-2-ylethynyl, 5-chloro-pyridin-3-yl, 5-cyano-pyridin-3-yl and 6-chloro-benzooxazol-2-yl.
10. The compound of claim 1, wherein $R^5$ is halogen.
11. The compound of claim 10, wherein $R^5$ is F.
12. The compound of claim 1, wherein $R^5$ is hydrogen.
13. The compound of claim 1, selected from the group consisting of
5-(6-Difluoromethoxy-pyridin-3-yl)-5-[3-(5-methoxy-pyridin-3-yl)-phenyl]-5,6-dihydro-2H-[1,4]oxazin-3-ylamine,
(R)-5-(3',5'-Dichloro-4-fluoro-biphenyl-3-yl)-5-methyl-5,6-dihydro-2H-[1,4]oxazin-3-ylamine,

[3'-(5-Amino-3-methyl-3,6-dihydro-2H-[1,4]oxazin-3-yl)-5-chloro-biphenyl-3-yl]-morpholin-4-yl-methanone,
[3'-(5-Amino-3-methyl-3,6-dihydro-2H-[1,4]oxazin-3-yl)-biphenyl-3-yl]-acetonitrile,
3'-(5-Amino-3-methyl-3,6-dihydro-2H-[1,4]oxazin-3-yl)-5-chloro-biphenyl-3-carboxylic acid amide,
3'-(5-Amino-3-methyl-3,6-dihydro-2H-[1,4]oxazin-3-yl)-biphenyl-3-carbonitrile,
5-(2',4'-Difluoro-biphenyl-3-yl)-5-methyl-5,6-dihydro-2H-[1,4]oxazin-3-ylamine,
5-(2',5'-Dichloro-biphenyl-3-yl)-5-methyl-5,6-dihydro-2H-[1,4]oxazin-3-ylamine,
5-(2'-Chloro-biphenyl-3-yl)-5-methyl-5,6-dihydro-2H-[1,4]oxazin-3-ylamine, and
5-(2-Fluoro-5-pyrimidin-5-yl-phenyl)-5-methyl-5,6-dihydro-2H-[1,4]oxazin-3-ylamine
or a pharmaceutically acceptable salt thereof.

14. The compound of claim 1, selected from the group consisting of
5-(3-(2,6-difluoropyridin-3-yl)phenyl)-5-methyl-5,6-dihydro-2H-1,4-oxazin-3-amine,
5-(3-(2-fluoropyridin-3-yl)phenyl)-5-methyl-5,6-dihydro-2H-1,4-oxazin-3-amine,
5-(3-(5-amino-3-methyl-3,6-dihydro-2H-1,4-oxazin-3-yl)phenyl)nicotinonitrile,
5-(3',5'-Dichloro-6-fluoro-biphenyl-3-yl)-5-methyl-5,6-dihydro-2H-[1,4]oxazin-3-ylamine,
5-(3',5'-Dichloro-biphenyl-3-yl)-5-methyl-5,6-dihydro-2H-[1,4]oxazin-3-ylamine,
5-(3',5'-Difluoro-biphenyl-3-yl)-5-methyl-5,6-dihydro-2H-[1,4]oxazin-3-ylamine,
5-(3'-Amino-biphenyl-3-yl)-5-methyl-5,6-dihydro-2H-[1,4]oxazin-3-ylamine,
5-(3-Benzo[1,3]dioxol-5-yl-phenyl)-5-methyl-5,6-dihydro-2H-[1,4]oxazin-3-ylamine,
5-(3'-Chloro-4'-fluoro-biphenyl-3-yl)-5-methyl-5,6-dihydro-2H-[1,4]oxazin-3-ylamine, and
5-(3'-Chloro-5'-methoxy-biphenyl-3-yl)-5-methyl-5,6-dihydro-2H-[1,4]oxazin-3-ylamine
or a pharmaceutically acceptable salt thereof.

15. The compound of claim 1, selected from the group consisting of
5-(3'-Chloro-5'-methyl-biphenyl-3-yl)-5-methyl-5,6-dihydro-2H-[1,4]oxazin-3-ylamine,
5-(3'-Chloro-biphenyl-3-yl)-5-methyl-5,6-dihydro-2H-[1,4]oxazin-3-ylamine,
5-(3'-Difluoromethoxy-biphenyl-3-yl)-5-methyl-5,6-dihydro-2H-[1,4]oxazin-3-ylamine,
5-(3'-Ethoxy-biphenyl-3-yl)-5-methyl-5,6-dihydro-2H-[1,4]oxazin-3-ylamine,
5-(4'-Chloro-3'-methyl-biphenyl-3-yl)-5-methyl-5,6-dihydro-2H-[1,4]oxazin-3-ylamine,
5-(4-Difluoromethoxy-3-methyl-phenyl)-5-(3-pyridin-3-yl-phenyl)-5,6-dihydro-2H-[1,4]oxazin-3-ylamine,
5-(4'-Fluoro-biphenyl-3-yl)-5-methyl-5,6-dihydro-2H-[1,4]oxazin-3-ylamine,
5-(4'-tert-Butyl-biphenyl-3-yl)-5-methyl-5,6-dihydro-2H-[1,4]oxazin-3-ylamine,
5-(5'-Chloro-2'-fluoro-3'-methyl-biphenyl-3-yl)-5-methyl-5,6-dihydro-2H-[1,4]oxazin-3-ylamine; compound with formic acid, and
5-(5'-Chloro-3'-trifluoromethyl-biphenyl-3-yl)-5-methyl-5,6-dihydro-2H-[1,4]oxazin-3-ylamine
or a pharmaceutically acceptable salt thereof.

16. The compound of claim 1, selected from the group consisting of
5-[3-(1H-Indol-5-yl)-phenyl]-5-methyl-5,6-dihydro-2H-[1,4]oxazin-3-ylamine,
5-[3-(2,2-Difluoro-benzo[1,3]dioxol-5-yl)-phenyl]-5-methyl-5,6-dihydro-2H-[1,4]oxazin-3-ylamine,
5-[3-(2,5-Dichloro-pyridin-3-yl)-phenyl]-5-methyl-5,6-dihydro-2H-[1,4]oxazin-3-ylamine,
5-[3-(2-Chloro-pyridin-4-yl)-phenyl]-5-methyl-5,6-dihydro-2H-[1,4]oxazin-3-ylamine,
5-[3-(3-Methoxy-prop-1-ynyl)-phenyl]-5-methyl-5,6-dihydro-2H-[1,4]oxazin-3-ylamine,
5-[3-(5-Chloro-1H-benzoimidazol-2-yl)-phenyl]-5-methyl-5,6-dihydro-2H-[1,4]oxazin-3-ylamine,
5-[3-(5-Chloro-pyridin-2-yl)-phenyl]-5-methyl-5,6-dihydro-2H-[1,4]oxazin-3-ylamine,
5-[3-(5-Chloro-pyridin-2-ylethynyl)-phenyl]-5-methyl-5,6-dihydro-2H-[1,4]oxazin-3-ylamine,
5-[3-(5-Chloro-pyridin-3-yl)-phenyl]-5-(4-difluoromethoxy-3-methyl-phenyl)-5,6-dihydro-2H-[1,4]oxazin-3-ylamine, and
5-[3-(5-Chloro-pyridin-3-yl)-phenyl]-5-(6-difluoromethoxy-pyridin-3-yl)-5,6-dihydro-2H-[1,4]oxazin-3-ylamine
or a pharmaceutically acceptable salt thereof.

17. The compound of claim 1, selected from the group consisting of
5-[3-(5-Chloro-pyridin-3-yl)-phenyl]-5-methyl-5,6-dihydro-2H-[1,4]oxazin-3-ylamine,
5-[3-(5-Methoxy-pyridin-3-yl)-phenyl]-5-methyl-5,6-dihydro-2H-[1,4]oxazin-3-ylamine,
5-[3-(6-Chloro-1H-indol-2-yl)-phenyl]-5-methyl-5,6-dihydro-2H-[1,4]oxazin-3-ylamine,
5-[3-(6-Chloro-benzooxazol-2-yl)-phenyl]-5-methyl-5,6-dihydro-2H-[1,4]oxazin-3-ylamine,
5-[3-(6-Chloro-pyridin-3-yl)-phenyl]-5-(4-difluoromethoxy-3-methyl-phenyl)-5,6-dihydro-2H-[1,4]oxazin-3-ylamine,
5-Methyl-5-(2',3',5'-trichloro-biphenyl-3-yl)-5,6-dihydro-2H-[1,4]oxazin-3-ylamine,
5-Methyl-5-(3-pyrimidin-5-yl-phenyl)-5,6-dihydro-2H-[1,4]oxazin-3-ylamine,
5-Methyl-5-(3-thiophen-3-yl-phenyl)-5,6-dihydro-2H-[1,4]oxazin-3-ylamine,
5-Methyl-5-(3'-trifluoromethoxy-biphenyl-3-yl)-5,6-dihydro-2H-[1,4]oxazin-3-ylamine, and
5-Methyl-5-[3-(1-methyl-1H-indazol-4-yl)-phenyl]-5,6-dihydro-2H-[1,4]oxazin-3-ylamine
or a pharmaceutically acceptable salt thereof.

18. The compound of claim 1, selected from the group consisting of
5-Difluoromethyl-5-(2-fluoro-5-pyrimidin-5-yl-phenyl)-5,6-dihydro-2H-[1,4]oxazin-3-ylamine,
5-[5-(5-Chloro-pyridin-3-yl)-2-fluoro-phenyl]-5-difluoromethyl-5,6-dihydro-2H-[1,4]oxazin-3-ylamine,
5-[3-(5-Chloro-benzooxazol-2-yl)-phenyl]-5-methyl-5,6-dihydro-2H-[1,4]oxazin-3-ylamine,
(RS)-5-[3-(5-Chloro-benzooxazol-2-yl)-phenyl]-5-methyl-5,6-dihydro-2H-[1,4]oxazin-3-ylamine hydrochloride,
5-Methyl-5-(3-phenylethynyl-phenyl)-5,6-dihydro-2H-[1,4]oxazin-3-ylamine,
5-Methyl-5-(3-thiophen-3-ylethynyl-phenyl)-5,6-dihydro-2H-[1,4]oxazin-3-ylamine,
5-(4',5'-Difluoro-3'-methoxy-biphenyl-3-yl)-5-methyl-5,6-dihydro-2H-[1,4]oxazin-3-ylamine formate,
5-(3',5'-Bis-trifluoromethyl-biphenyl-3-yl)-5-methyl-5,6-dihydro-2H-[1,4]oxazin-3-ylamine formate, 5-[4'-Fluoro-3'-(2,2,2-trifluoro-ethoxy)-biphenyl-3-yl]-5-methyl-5,6-dihydro-2H-[1,4]oxazin-3-ylamine formate, and 5-[3-(7-Methoxy-naphthalen-2-yl)-phenyl]-5-methyl-5,6-dihydro-2H-[1,4]oxazin-3-ylamine formate or a pharmaceutically acceptable salt thereof.

19. The compound of claim 1, selected from the group consisting of 5-(6-Difluoromethoxy-pyridin-3-yl)-5-[3-(5-methoxy-pyridin-3-yl)-phenyl]-5,6-dihydro-2H-[1,4]oxazin-3-ylamine, (R)-5-(3',5'-Dichloro-4-fluoro-biphenyl-3-yl)-5-methyl-5,6-dihydro-2H-[1,4]oxazin-3-ylamine,

[3'-(5-Amino-3-methyl-3,6-dihydro-2H-[1,4]oxazin-3-yl)-5-chloro-biphenyl-3-yl]-morpholin-4-yl-methanone,

[3'-(5-Amino-3-methyl-3,6-dihydro-2H-[1,4]oxazin-3-yl)-biphenyl-3-yl]-acetonitrile, 3'-(5-Amino-3-methyl-3,6-dihydro-2H-[1,4]oxazin-3-yl)-5-chloro-biphenyl-3-carboxylic acid amide, 3'-(5-Amino-3-methyl-3,6-dihydro-2H-[1,4]oxazin-3-yl)-biphenyl-3-carbonitrile, 5-(2',4'-Difluoro-biphenyl-3-yl)-5-methyl-5,6-dihydro-2H-[1,4]oxazin-3-ylamine, 5-(2',5'-Dichloro-biphenyl-3-yl)-5-methyl-5,6-dihydro-2H-[1,4]oxazin-3-ylamine, 5-(2'-Chloro-biphenyl-3-yl)-5-methyl-5,6-dihydro-2H-[1,4]oxazin-3-ylamine, and 5-(2-Fluoro-5-pyrimidin-5-yl-phenyl)-5-methyl-5,6-dihydro-2H-[1,4]oxazin-3-ylamine or a pharmaceutically acceptable salt thereof.

20. The compound of claim 1, selected from the group consisting of 5-(3-(2,6-Difluoropyridin-3-yl)phenyl)-5-methyl-5,6-dihydro-2H-1,4-oxazin-3-amine, 5-(3-(2-Dluoropyridin-3-yl)phenyl)-5-methyl-5,6-dihydro-2H-1,4-oxazin-3-amine, 5-(3-(5-Amino-3-methyl-3,6-dihydro-2H-1,4-oxazin-3-yl)phenyl)nicotinonitrile, 5-(3',5'-Dichloro-6-fluoro-biphenyl-3-yl)-5-methyl-5,6-dihydro-2H-[1,4]oxazin-3-ylamine, 5-(3',5'-Dichloro-biphenyl-3-yl)-5-methyl-5,6-dihydro-2H-[1,4]oxazin-3-ylamine, 5-(3',5'-Difluoro-biphenyl-3-yl)-5-methyl-5,6-dihydro-2H-[1,4]oxazin-3-ylamine, 5-(3'-Amino-biphenyl-3-yl)-5-methyl-5,6-dihydro-2H-[1,4]oxazin-3-ylamine, 5-(3-Benzo[1,3]dioxol-5-yl-phenyl)-5-methyl-5,6-dihydro-2H-[1,4]oxazin-3-ylamine, 5-(3'-Chloro-4'-fluoro-biphenyl-3-yl)-5-methyl-5,6-dihydro-2H-[1,4]oxazin-3-ylamine, and 5-(3'-Chloro-5'-methoxy-biphenyl-3-yl)-5-methyl-5,6-dihydro-2H-[1,4]oxazin-3-ylamine or a pharmaceutically acceptable salt thereof.

21. The compound of claim 1, selected from the group consisting of 5-(3'-Chloro-5'-methyl-biphenyl-3-yl)-5-methyl-5,6-dihydro-2H-[1,4]oxazin-3-ylamine, 5-(3'-Chloro-biphenyl-3-yl)-5-methyl-5,6-dihydro-2H-[1,4]oxazin-3-ylamine, 5-(3'-Difluoromethoxy-biphenyl-3-yl)-5-methyl-5,6-dihydro-2H-[1,4]oxazin-3-ylamine, 5-(3'-Ethoxy-biphenyl-3-yl)-5-methyl-5,6-dihydro-2H-[1,4]oxazin-3-ylamine, 5-(4'-Chloro-3'-methyl-biphenyl-3-yl)-5-methyl-5,6-dihydro-2H-[1,4]oxazin-3-ylamine, 5-(4-Difluoromethoxy-3-methyl-phenyl)-5-(3-pyridin-3-yl-phenyl)-5,6-dihydro-2H-[1,4]oxazin-3-ylamine, 5-(4'-Fluoro-biphenyl-3-yl)-5-methyl-5,6-dihydro-2H-[1,4]oxazin-3-ylamine, 5-(4'-tert-Butyl-biphenyl-3-yl)-5-methyl-5,6-dihydro-2H-[1,4]oxazin-3-ylamine, 5-(5'-Chloro-2'-fluoro-3'-methyl-biphenyl-3-yl)-5-methyl-5,6-dihydro-2H-[1,4]oxazin-3-ylamine formate, and 5-(5'-Chloro-3'-trifluoromethyl-biphenyl-3-yl)-5-methyl-5,6-dihydro-2H-[1,4]oxazin-3-ylamine or a pharmaceutically acceptable salt thereof.

22. The compound of claim 1, selected from the group consisting of

5-[3-(1H-Indol-5-yl)-phenyl]-5-methyl-5,6-dihydro-2H-[1,4]oxazin-3-ylamine,

5-[3-(2,2-Difluoro-benzo[1,3]dioxol-5-yl)-phenyl]-5-methyl-5,6-dihydro-2H-[1,4]oxazin-3-ylamine, 5-[3-(2,5-Dichloro-pyridin-3-yl)-phenyl]-5-methyl-5,6-dihydro-2H-[1,4]oxazin-3-ylamine, 5-[3-(2-Chloro-pyridin-4-yl)-phenyl]-5-methyl-5,6-dihydro-2H-[1,4]oxazin-3-ylamine, 5-[3-(3-Methoxy-prop-1-ynyl)-phenyl]-5-methyl-5,6-dihydro-2H-[1,4]oxazin-3-ylamine, 5-[3-(5-Chloro-1H-benzoimidazol-2-yl)-phenyl]-5-methyl-5,6-dihydro-2H-[1,4]oxazin-3-ylamine, 5-[3-(5-Chloro-pyridin-2-yl)-phenyl]-5-methyl-5,6-dihydro-2H-[1,4]oxazin-3-ylamine, 5-[3-(5-Chloro-pyridin-2-ylethynyl)-phenyl]-5-methyl-5,6-dihydro-2H-[1,4]oxazin-3-ylamine, 5-[3-(5-Chloro-pyridin-3-yl)-phenyl]-5-(4-difluoromethoxy-3-methyl-phenyl)-5,6-dihydro-2H-[1,4]oxazin-3-ylamine, and 5-[3-(5-Chloro-pyridin-3-yl)-phenyl]-5-(6-difluoromethoxy-pyridin-3-yl)-5,6-dihydro-2H-[1,4]oxazin-3-ylamine or a pharmaceutically acceptable salt thereof.

23. The compound of claim 1, selected from the group consisting of

5-[3-(5-Chloro-pyridin-3-yl)-phenyl]-5-methyl-5,6-dihydro-2H-[1,4]oxazin-3-ylamine, 5-[3-(5-Methoxy-pyridin-3-yl)-phenyl]-5-methyl-5,6-dihydro-2H-[1,4]oxazin-3-ylamine, 5-[3-(6-Chloro-1H-indol-2-yl)-phenyl]-5-methyl-5,6-dihydro-2H-[1,4]oxazin-3-ylamine, 5-[3-(6-Chloro-benzooxazol-2-yl)-phenyl]-5-methyl-5,6-dihydro-2H-[1,4]oxazin-3-ylamine, 5-[3-(6-Chloro-pyridin-3-yl)-phenyl]-5-(4-difluoromethoxy-3-methyl-phenyl)-5,6-dihydro-2H-[1,4]oxazin-3-ylamine, 5-Methyl-5-(2',3',5'-trichloro-biphenyl-3-yl)-5,6-dihydro-2H-[1,4]oxazin-3-ylamine, 5-Methyl-5-(3-pyrimidin-5-yl-phenyl)-5,6-dihydro-2H-[1,4]oxazin-3-ylamine, 5-Methyl-5-(3-thiophen-3-yl-phenyl)-5,6-dihydro-2H-[1,4]oxazin-3-ylamine, 5-Methyl-5-(3'-trifluoromethoxy-biphenyl-3-yl)-5,6-dihydro-2H-[1,4]oxazin-3-ylamine, and 5-Methyl-5-[3-(1-methyl-1H-indazol-4-yl)-phenyl]-5,6-dihydro-2H-[1,4]oxazin-3-ylamine, or a pharmaceutically acceptable salt thereof.

24. The compound of claim 1, selected from the group consisting of 5-(6-Difluoromethoxy-pyridin-3-yl)-5-[3-(5-methoxy-pyridin-3-yl)-phenyl]-5,6-dihydro-2H-[1,4]oxazin-3-ylamine hydrochloride, (R)-5-(3',5'-Dichloro-4-fluoro-biphenyl-3-yl)-5-methyl-5,6-dihydro-2H-[1,4]oxazin-3-ylamine formate,
5-(3-(2,6-difluoropyridin-3-yl)phenyl)-5-methyl-5,6-dihydro-2H-1,4-oxazin-3-amine trifluoroacetate,
5-(3-(2-fluoropyridin-3-yl)phenyl)-5-methyl-5,6-dihydro-2H-1,4-oxazin-3-amine trifluoroacetate,
5-(3-(5-amino-3-methyl-3,6-dihydro-2H-1,4-oxazin-3-yl)phenyl)nicotinonitrile trifluoroacetate,
5-(4-Difluoromethoxy-3-methyl-phenyl)-5-(3-pyridin-3-yl-phenyl)-5,6-dihydro-2H-[1,4]oxazin-3-ylamine hydrochloride,
5-[3-(5-Chloro-pyridin-2-ylethynyl)-phenyl]-5-methyl-5,6-dihydro-2H-[1,4]oxazin-3-ylamine,
5-[3-(5-Chloro-pyridin-3-yl)-phenyl]-5-(4-difluoromethoxy-3-methyl-phenyl)-5,6-dihydro-2H-[1,4]oxazin-3-ylamine hydrochloride,
5-[3-(5-Chloro-pyridin-3-yl)-phenyl]-5-(6-difluoromethoxy-pyridin-3-yl)-5,6-dihydro-2H-[1,4]oxazin-3-ylamine hydrochloride,
5-[3-(5-Chloro-pyridin-3-yl)-phenyl]-5-methyl-5,6-dihydro-2H-[1,4]oxazin-3-ylamine, and
5-[3-(6-Chloro-benzooxazol-2-yl)-phenyl]-5-methyl-5,6-dihydro-2H-[1,4]oxazin-3-ylamine hydrochloride
or a pharmaceutically acceptable salt thereof.

25. A pharmaceutical composition comprising a therapeutically effective amount of a compound of formula I

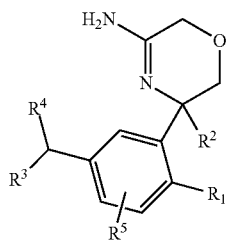

I wherein
$R^1$ is selected from the group consisting of
iv) hydrogen,
v) halogen, and
vi) $C_{1-6}$-alkyl;
$R^2$ is selected from the group consisting of
vii) hydrogen,
viii) $C_{1-6}$-alkyl,
ix) heteroaryl,
x) heteroaryl substituted by 1-4 substituents individually selected from halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl,
xi) aryl, and
xii) aryl substituted by 1-4 substituents individually selected from halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl;
$R^3$ and $R^4$ together with the C to which they are attached form a group selected from the group consisting of
xi) aryl,
xii) aryl substituted by 1-4 substituents individually selected from acetamidyl, amino, amido, —C(O)-heterocyclyl, cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl,
xiii) heteroaryl,
xiv) heteroaryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl and $C_{1-6}$-alkyl,
xv) $C_{2-6}$-alkynyl,
xvi) $C_{2-6}$-alkynyl substituted by 1-5 substituents individually selected from aryl, cyano, halogen-aryl, halogen, halogen-heteroaryl, heteroaryl, ydroxyl, $C_{1-6}$-alkyl, $C_{1-6}$-alkyl-aryl, $C_{1-6}$-alkyl-heteroaryl and $C_{1-6}$-alkoxy,
xvii) $C_{3-6}$-cycloalkyl,
xviii) $C_{3-6}$-cycloalkyl substituted by 1-4 substituents individually selected from cyano, cyano-$C_{1-6}$-alkyl, halogen, halogen-$C_{1-6}$-alkoxy, halogen-$C_{1-6}$-alkyl, ydroxyl, $C_{1-6}$-alkoxy, $C_{1-6}$-alkoxy-$C_{1-6}$-alkyl and $C_{1-6}$-alkyl,
xix) heterocyclyl, and
xx) heterocyclyl substituted by 1-4 substituents individually selected from halogen, halogen-$C_{1-6}$-alkoxy, halogen-$C_{1-6}$-alkyl, ydroxyl, $C_{1-6}$-alkoxy, $C_{1-6}$-alkoxy-$C_{1-6}$-alkyl and $C_{1-6}$-alkyl;
$R^5$ is selected from the group consisting of
iv) hydrogen,
v) halogen, and
vi) $C_{1-6}$-alkyl;
or a pharmaceutically acceptable salt thereof and a pharmaceutically acceptable carrier and/or a pharmaceutically acceptable auxiliary substance.

* * * * *